(12) United States Patent
Alsberg et al.

(10) Patent No.: US 11,273,236 B2
(45) Date of Patent: Mar. 15, 2022

(54) ENGINEERED TISSUE CONSTRUCTS

(71) Applicants: Case Western Reserve University, Cleveland, OH (US); Worcester Polytechnic Institute, Worcester, MA (US)

(72) Inventors: Eben Alsberg, Cleveland, OH (US); Anna D. Dikina, Mentor, OH (US); Marsha W. Rolle, Worcester, MA (US); Hannah A. Strobel, Marlborough, MA (US)

(73) Assignees: CASE WESTERN RESERVE UNIVERSITY, Cleveland, OH (US); WORCESTER POLYTECHNIC INSTITUTE, Worcester, MA (US)

( * ) Notice: Subject to any disclaimer, the term of this patent is extended or adjusted under 35 U.S.C. 154(b) by 109 days.

(21) Appl. No.: 15/698,429

(22) Filed: Sep. 7, 2017

(65) Prior Publication Data
US 2018/0064851 A1    Mar. 8, 2018

Related U.S. Application Data

(63) Continuation-in-part of application No. 15/258,666, filed on Sep. 7, 2016.
(Continued)

(51) Int. Cl.
*A61L 27/38* (2006.01)
*A61K 35/42* (2015.01)
(Continued)

(52) U.S. Cl.
CPC .......... *A61L 27/3817* (2013.01); *A61K 35/28* (2013.01); *A61K 35/32* (2013.01);
(Continued)

(58) Field of Classification Search
None
See application file for complete search history.

(56) References Cited

U.S. PATENT DOCUMENTS 6,886,568 B2 * 5/2005 Frondoza ............. A61K 9/0019
128/898
8,388,948 B2    3/2013 Basu et al.
(Continued)

FOREIGN PATENT DOCUMENTS

WO    90/10454 A1    9/1990

OTHER PUBLICATIONS

Schrobback et al., J. Orthop. Res. 29: 539-546 (2011).*
(Continued)

*Primary Examiner* — Erin M. Bowers
(74) *Attorney, Agent, or Firm* — Tarolli, Sundheim, Covell & Tummino LLP

(57) ABSTRACT

A modular engineered tissue construct includes a plurality of fused self-assembled, scaffold-free, high-density cell aggregates. At least one cell aggregate includes a plurality of cells and a plurality of biocompatible and biodegradable nanoparticles and/or microparticles that are incorporated within the cell aggregates. The nanoparticles and/or microparticles acting as a bulking agent within the cell aggregate to increase the cell aggregate size and/or thickness and improve the mechanical properties of the cell aggregate as well as to deliver bioactive agents.

11 Claims, 34 Drawing Sheets

Related U.S. Application Data

(60) Provisional application No. 62/384,400, filed on Sep. 7, 2016.

(51) Int. Cl.

| | | |
|---|---|---|
| *A61L 27/58* | (2006.01) | |
| *A61K 35/32* | (2015.01) | |
| *A61K 35/44* | (2015.01) | |
| *A61L 27/54* | (2006.01) | |
| *A61K 35/28* | (2015.01) | |
| *C12N 5/071* | (2010.01) | |
| *C12N 5/077* | (2010.01) | |
| *C12M 1/12* | (2006.01) | |
| *C12M 3/00* | (2006.01) | |

(52) U.S. Cl.
CPC ............ *A61K 35/42* (2013.01); *A61K 35/44* (2013.01); *A61L 27/3804* (2013.01); *A61L 27/3839* (2013.01); *A61L 27/3886* (2013.01); *A61L 27/54* (2013.01); *A61L 27/58* (2013.01); *C12N 5/0655* (2013.01); *C12N 5/0697* (2013.01); *A61L 2300/414* (2013.01); *A61L 2300/62* (2013.01); *A61L 2400/12* (2013.01); *A61L 2430/02* (2013.01); *C12M 21/08* (2013.01); *C12M 25/14* (2013.01); *C12N 2533/30* (2013.01)

(56) References Cited

U.S. PATENT DOCUMENTS

| | | | |
|---|---|---|---|
| 8,507,266 B2 | 8/2013 | Welter et al. | |
| 9,370,606 B2 | 6/2016 | Nakamura et al. | |
| 2002/0025308 A1* | 2/2002 | Costantino ............ | A61P 19/04 424/93.21 |
| 2016/0279868 A1 | 9/2016 | Burdick et al. | |
| 2017/0327813 A1 | 11/2017 | Cattolico et al. | |

OTHER PUBLICATIONS

Kojima et al., FASEB J. 17: 823-828 (2003).*
Eben Alsberg; U.S. Appl. No. 16/107,756, filed Aug. 21, 2018; NonFinal Office Action; dated Aug. 26, 2020; 16 pgs.
First Named Inventor: Eben Alsberg; U.S. Appl. No. 16/107,774, filed Aug. 21, 2018; NonFinal Office Action; dated Sep. 17, 2020; 16 pgs.
First Named Inventor: Eben Alsberg; U.S. Appl. No. 16/726,375, filed Dec. 24, 2019 NonFinal Office Action; dated Oct. 5, 2020.
Applicant: Case Western Reserve University; PCT International Application No. PCT/US19/26678; International Filing Date: Apr. 9, 2019; PCT International Search Report and Written Opinion; Authorized Officer: Lee W. Young; Date of Completion: Jun. 11, 2019; 11 pgs.
Applicant: Case Western Reserve University, et al.; European Patent Application No. 17879074.7, Filing Date: Dec. 11, 2017; Communication pursuant to Article 94(3) EPC; dated Jul. 20, 2020; 10 pgs.
Chelsea S. Bahney, et al., "Stem Cell-Derived Endochondral Cartilage Stimulates Bone Healing by Tissue Transformation", Journal of Bone and Mineral Research, vol. 29, No. 5, Apr. 22, 2014, pp. 1269-1282.
Chelsea S. Bahney, et al., "The Multifaceted Role of the Vasculature in Endochondral Fracture Repair", Frontiers in Endocrinology, vol. 6, Feb. 5, 2015 (Feb. 5, 2015), p. 4.
Dazai S, et al., "Leukemia inhibitory factor enhances bone formation in calvarial bone defect", The Journal of Craniofacial Surgery, Nov. 2000, vol. 11, No. 6, Nov. 2000, pp. 513-520.
Guihard P, et al., "Induction of osteogenesis in mesenchymal stem cells by activated monocytes/macrophages depends on Oncostatin M signaling", vol. 50, May 2012.
Italian Patent Office, Document No. 102011902009885A1, (Bionest Ltd), Jul. 1, 2013 (Jul. 1, 2013).
L. Yang, et al., "Hypertrophic chondrocytes can become osteoblasts and osteocytes in endochondral bone formation", Proceedings of the National Academy of Sciences, vol. 111, No. 33, Aug. 19, 2014, pp. 12097-12102.
Rachelle W. Johnson, et al., "Glycoprotein130 (Gp130)/interleukin-6 (IL-6) signalling in osteoclasts promotes bone formation in periosteal and trabecular bone", Bone, vol. 81, Aug. 7, 2015, pp. 343-351.
Rozen, et al., "Fracture repair: Modulation of fracture-callus and mechanical properties by sequential application of IL-6 following PTH 1-34 or PTH 28-48, IL-6 following PTH 1-34 or PTH 28-48", Bone, Pergamon Press., Oxford, GB, vol. 41, No. 3, Aug. 8, 2007, pp. 437-445.
Xin Zhou, et al., "Chondrocytes Transdifferentiate into Osteoblasts in Endochondral Bone during Development, Postnatal Growth and Fracture Healing in Mice", PLOS Genetics, vol. 10, No. 12, Dec. 4, 2014.

* cited by examiner

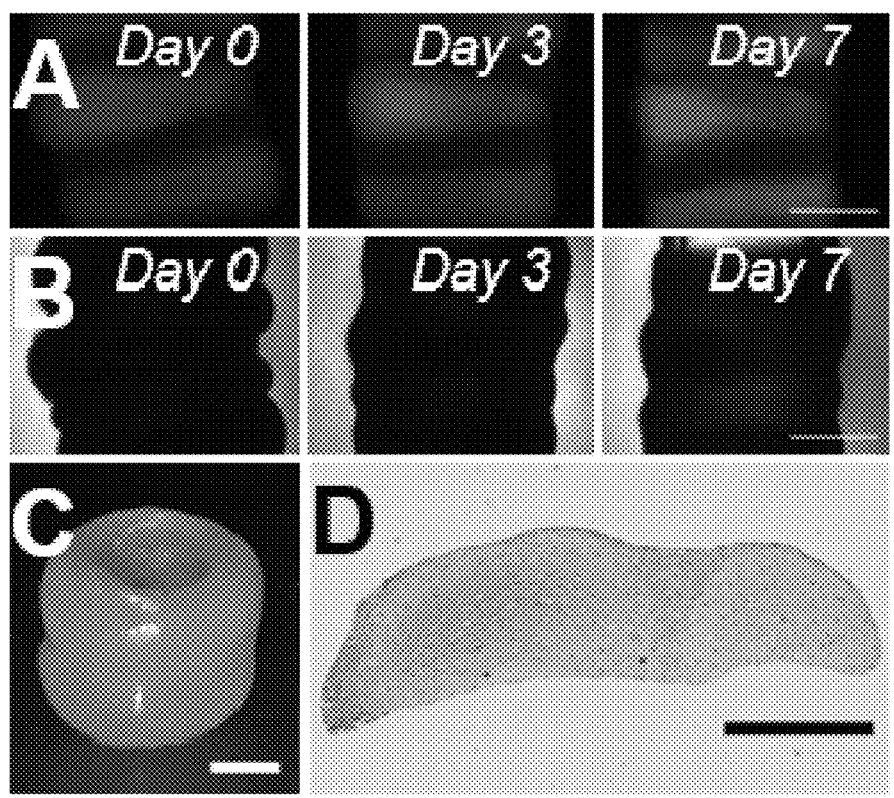
Figs. 3A-D
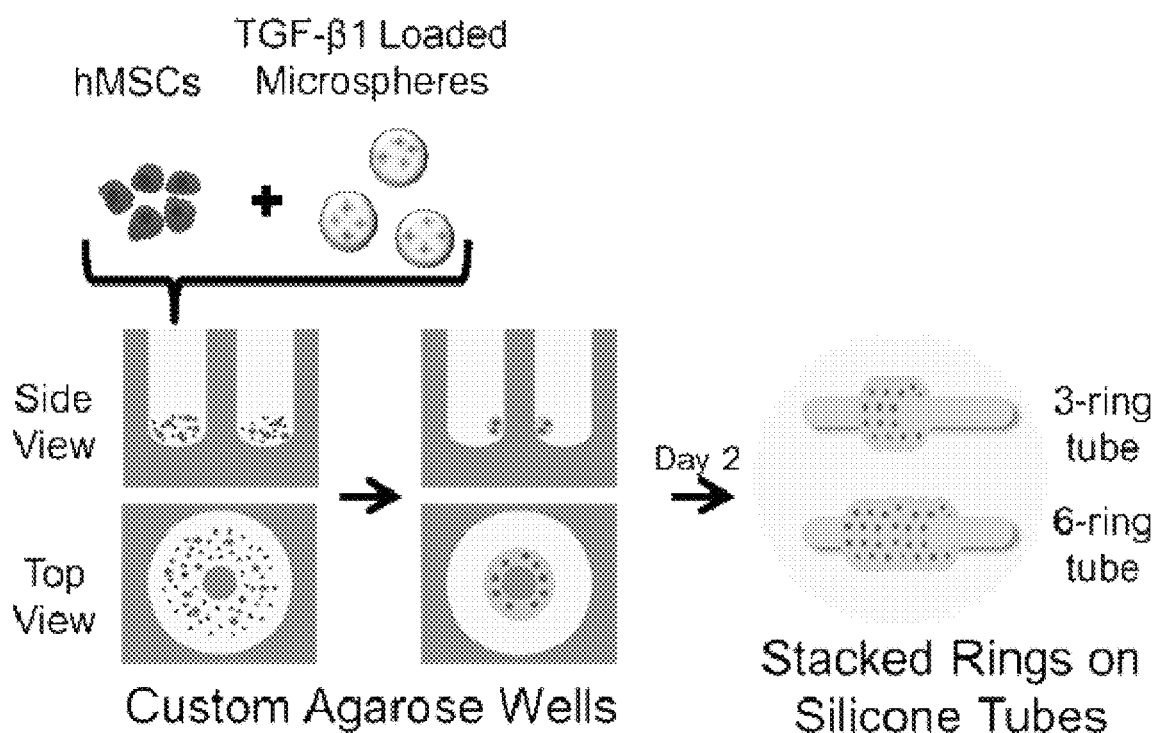
Fig. 4

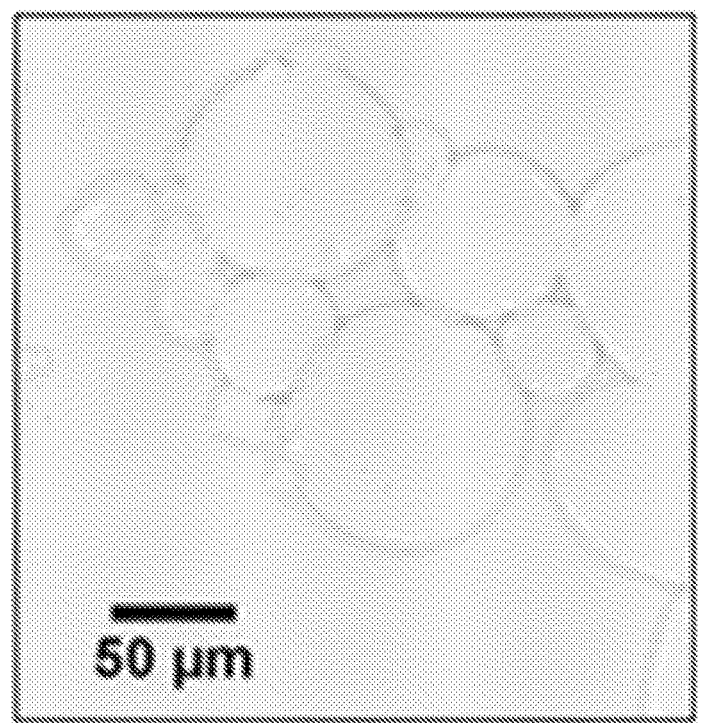
Fig. 5
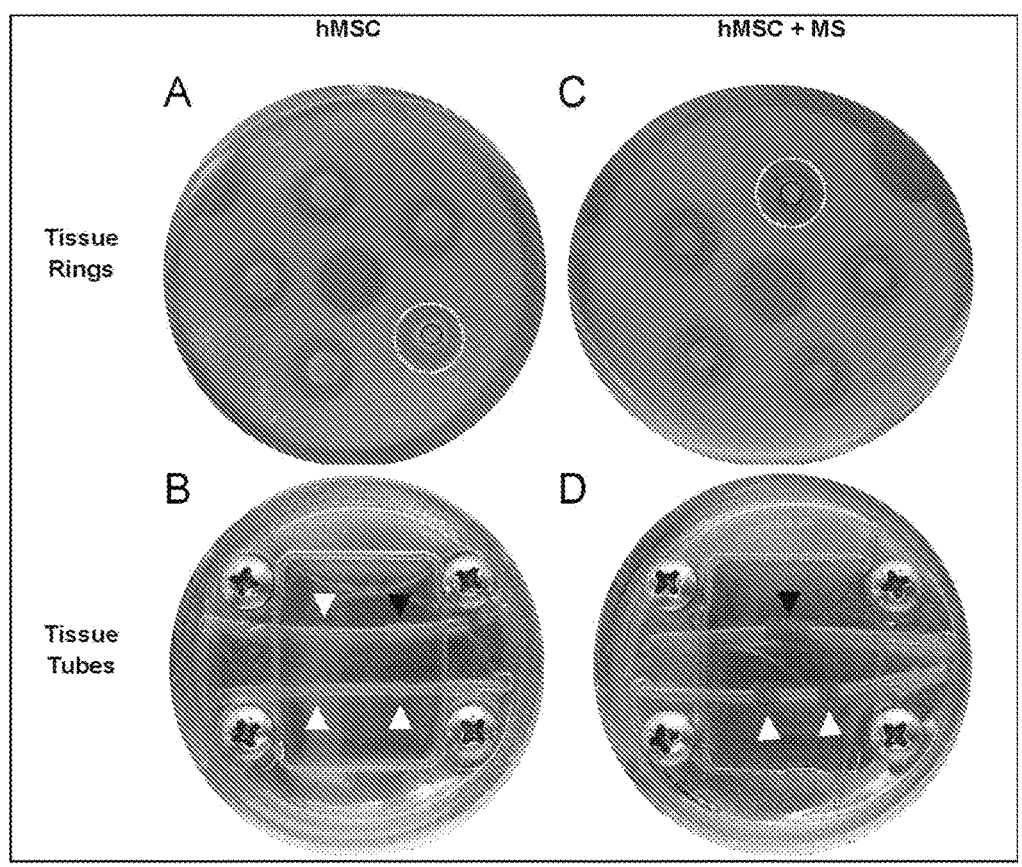
Figs. 6A-D

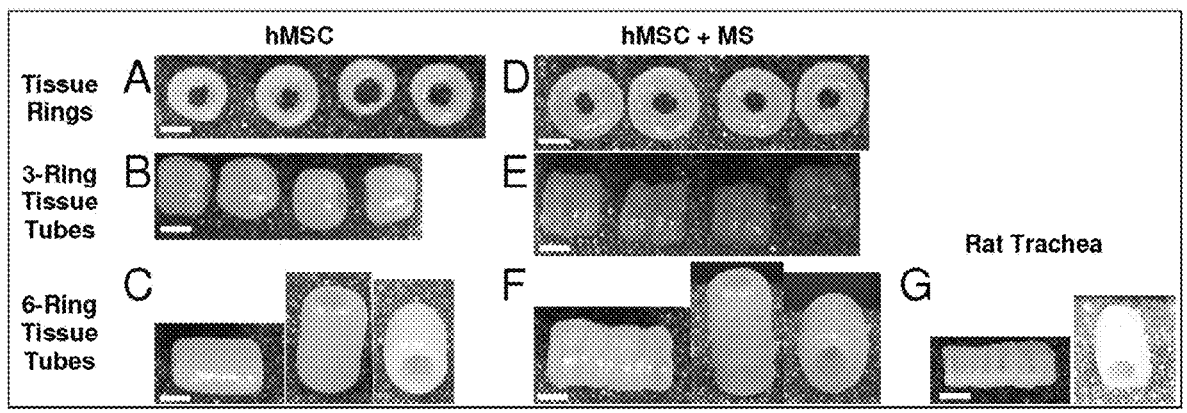
Figs. 7A-G
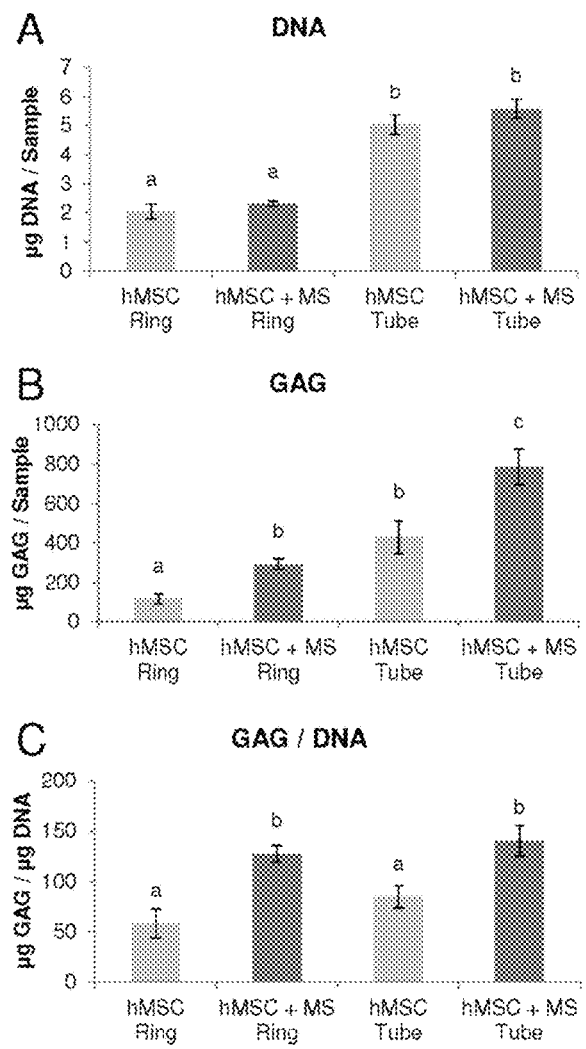
Figs. 8A-C

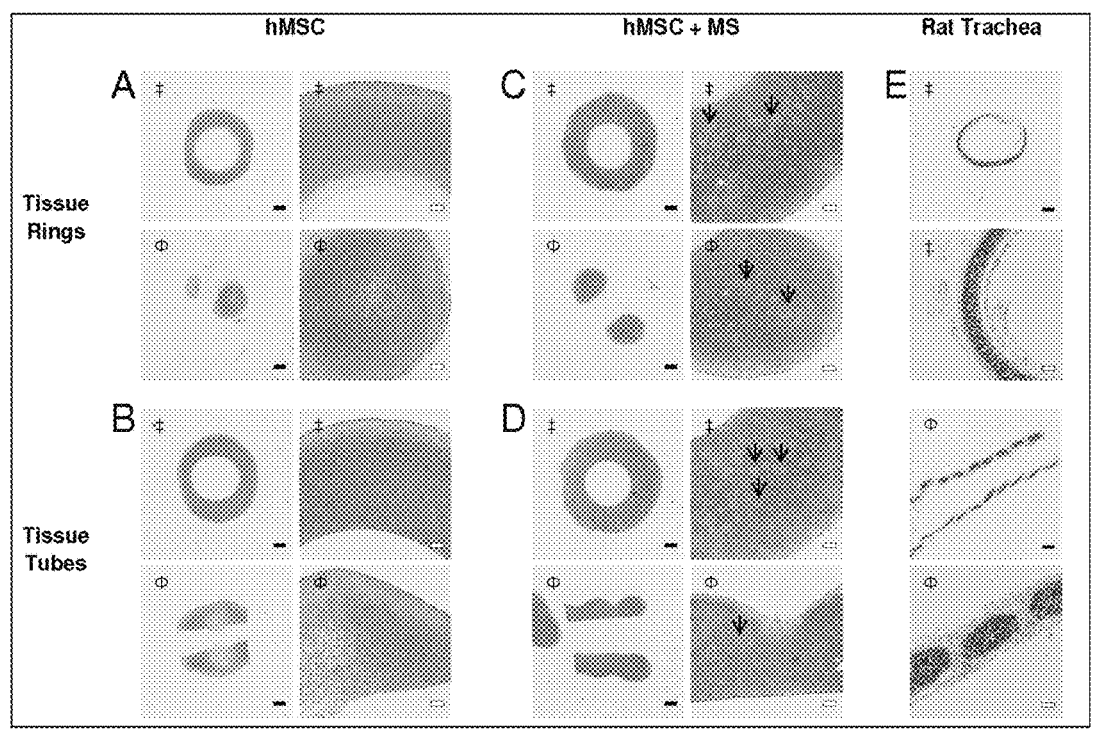
Figs. 9A-E
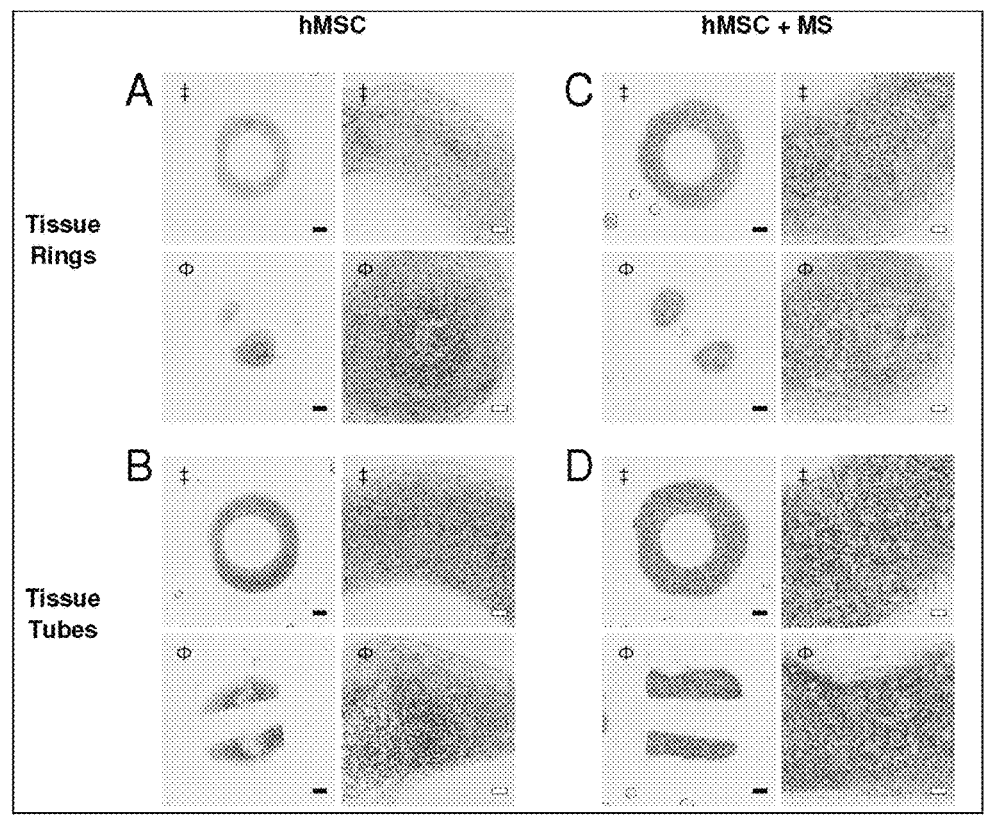
Figs. 10A-D

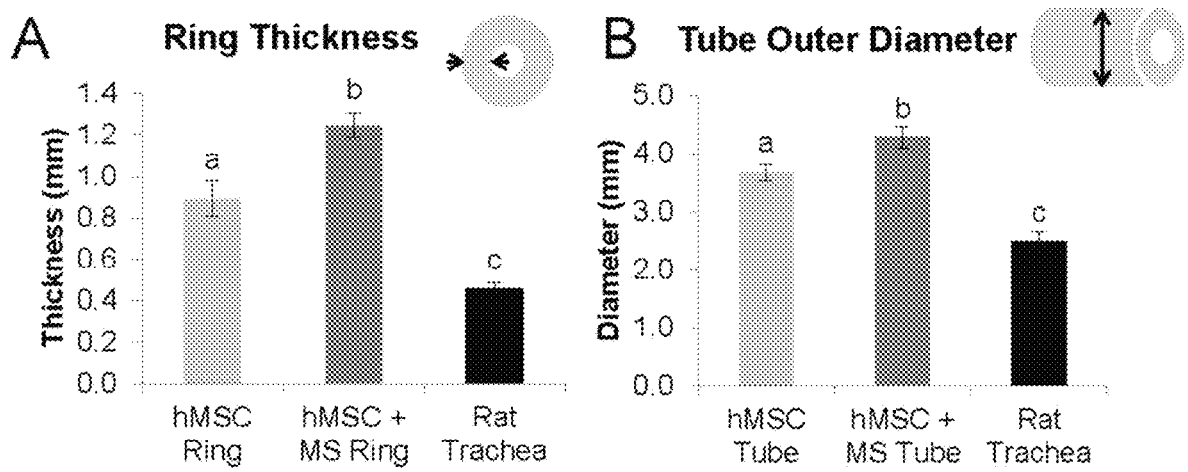
Figs. 11A-B
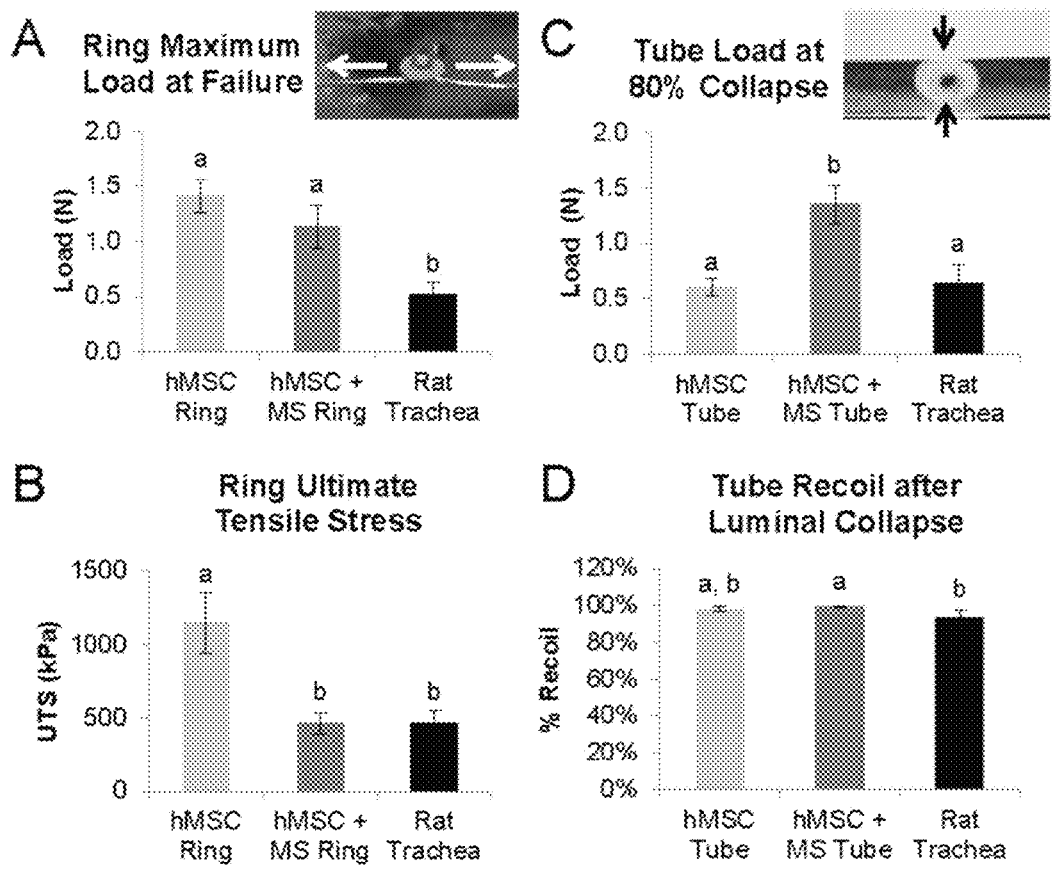
Figs. 12A-D

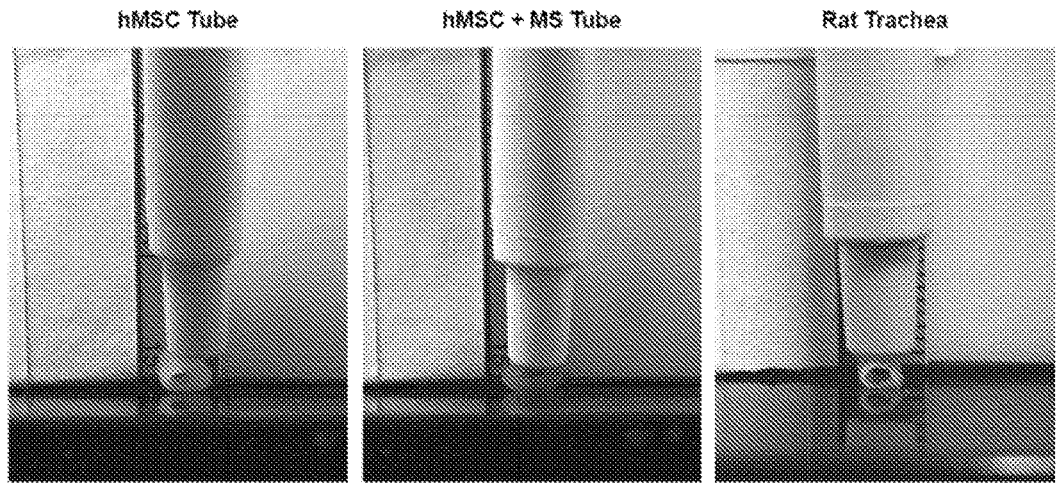
Fig. 13
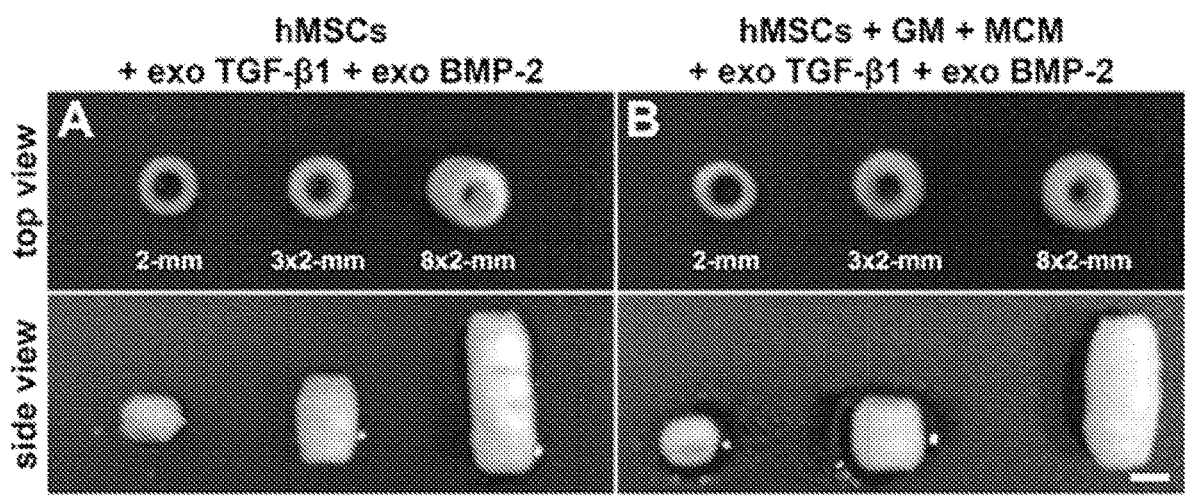
Figs. 14A-B

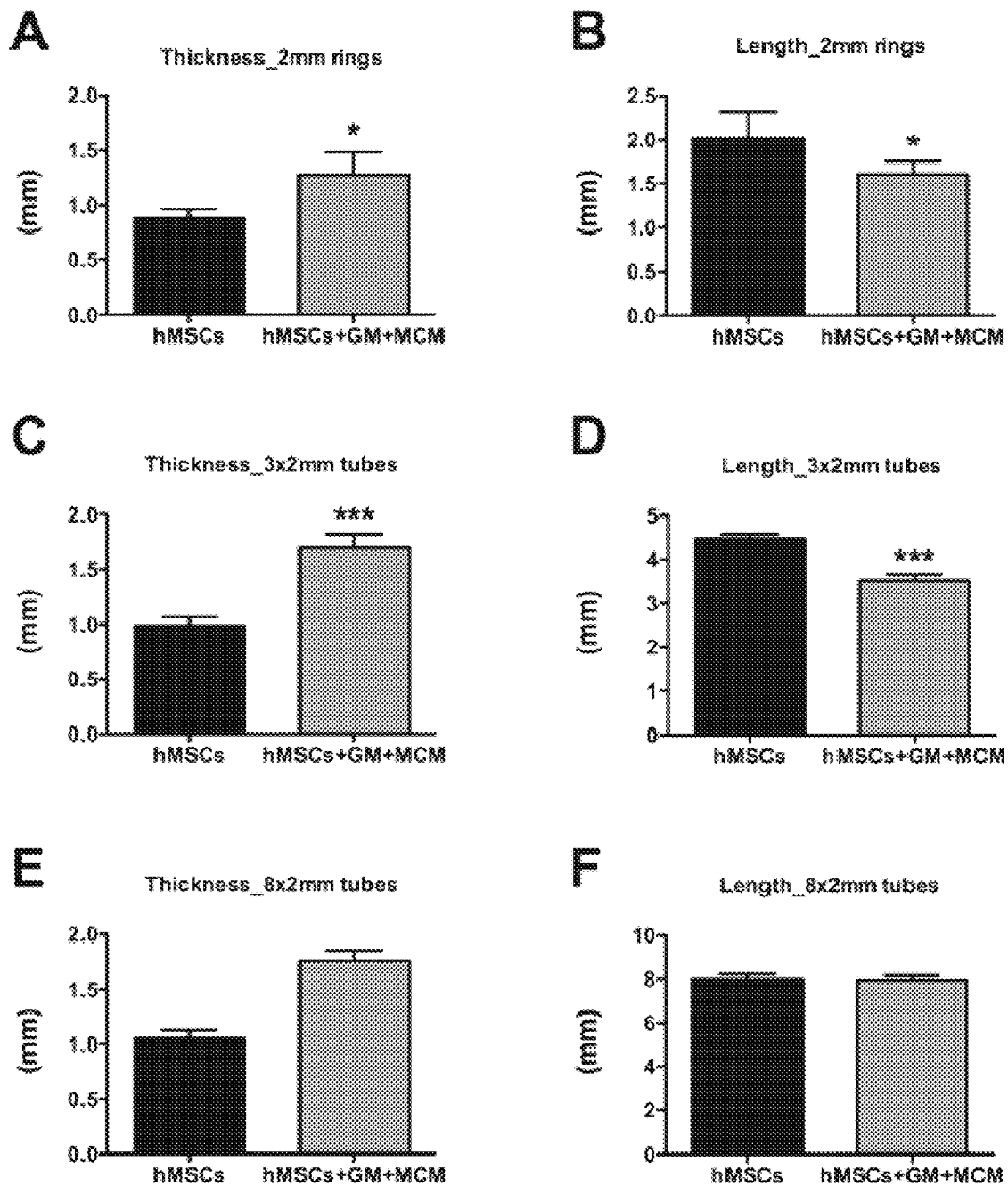
Figs. 15A-F

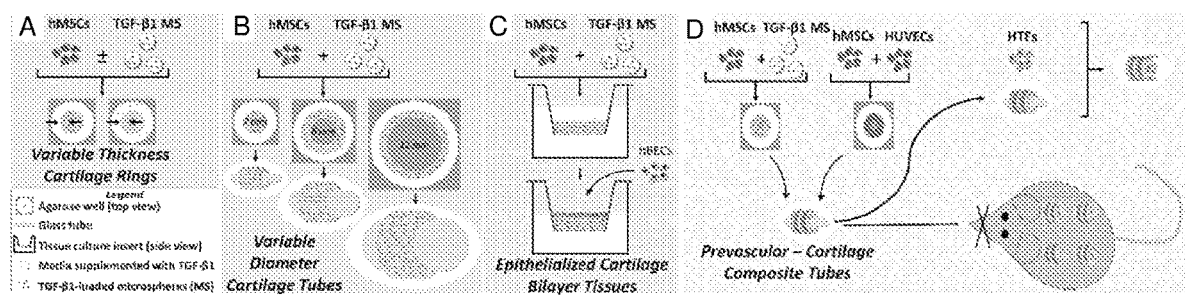
Figs. 16A-D

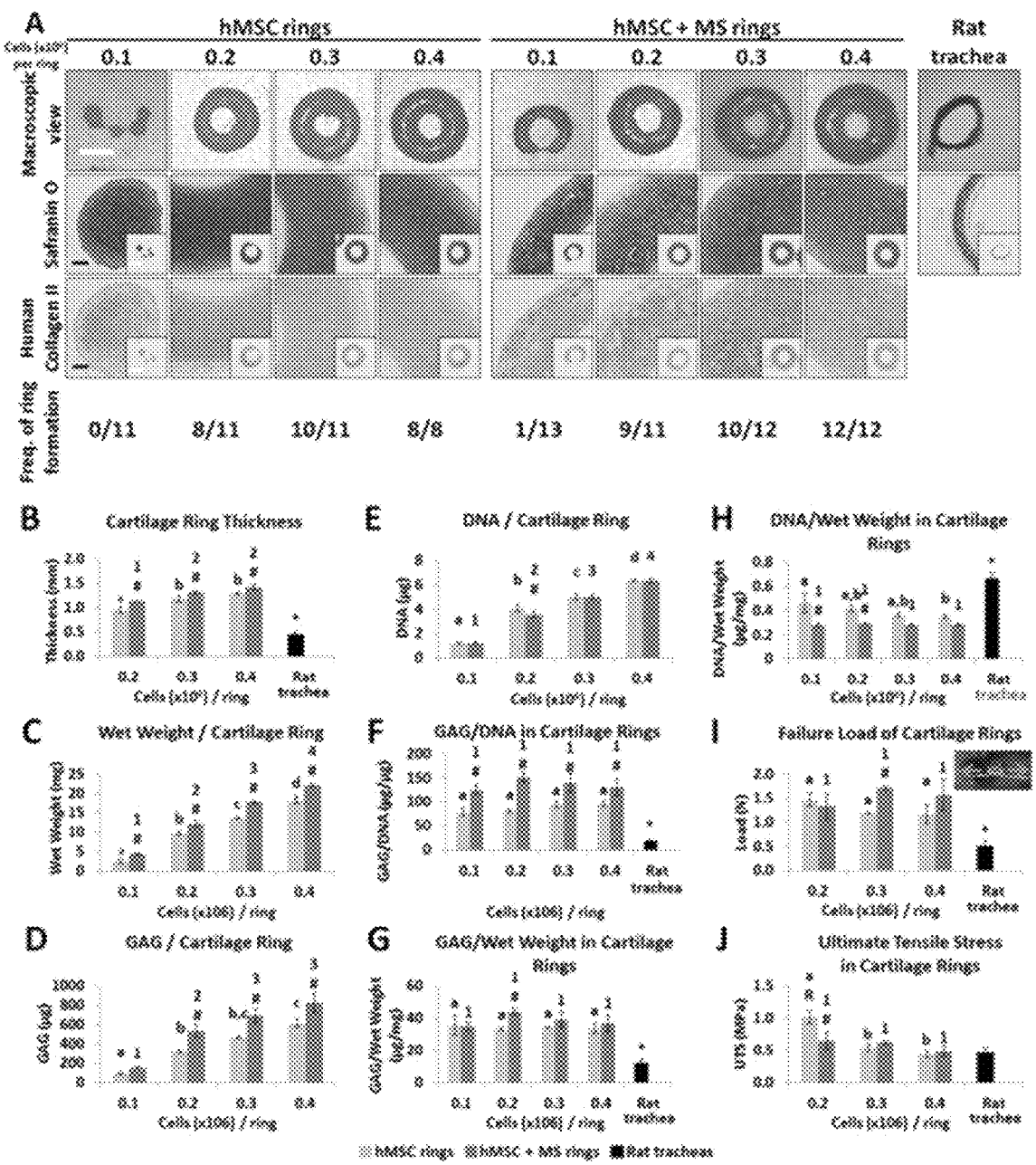
Figs. 17A-J

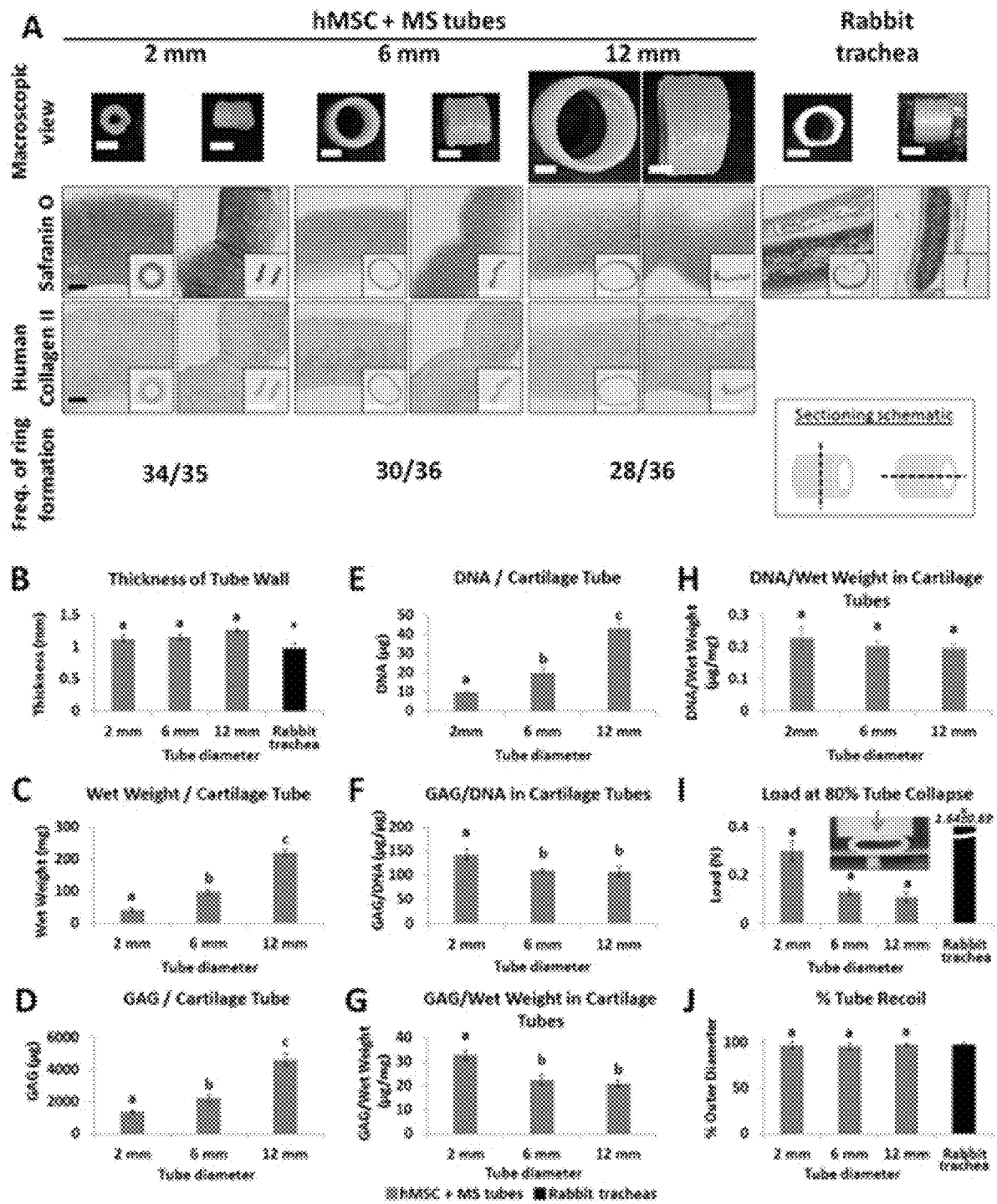
Figs. 18A-J

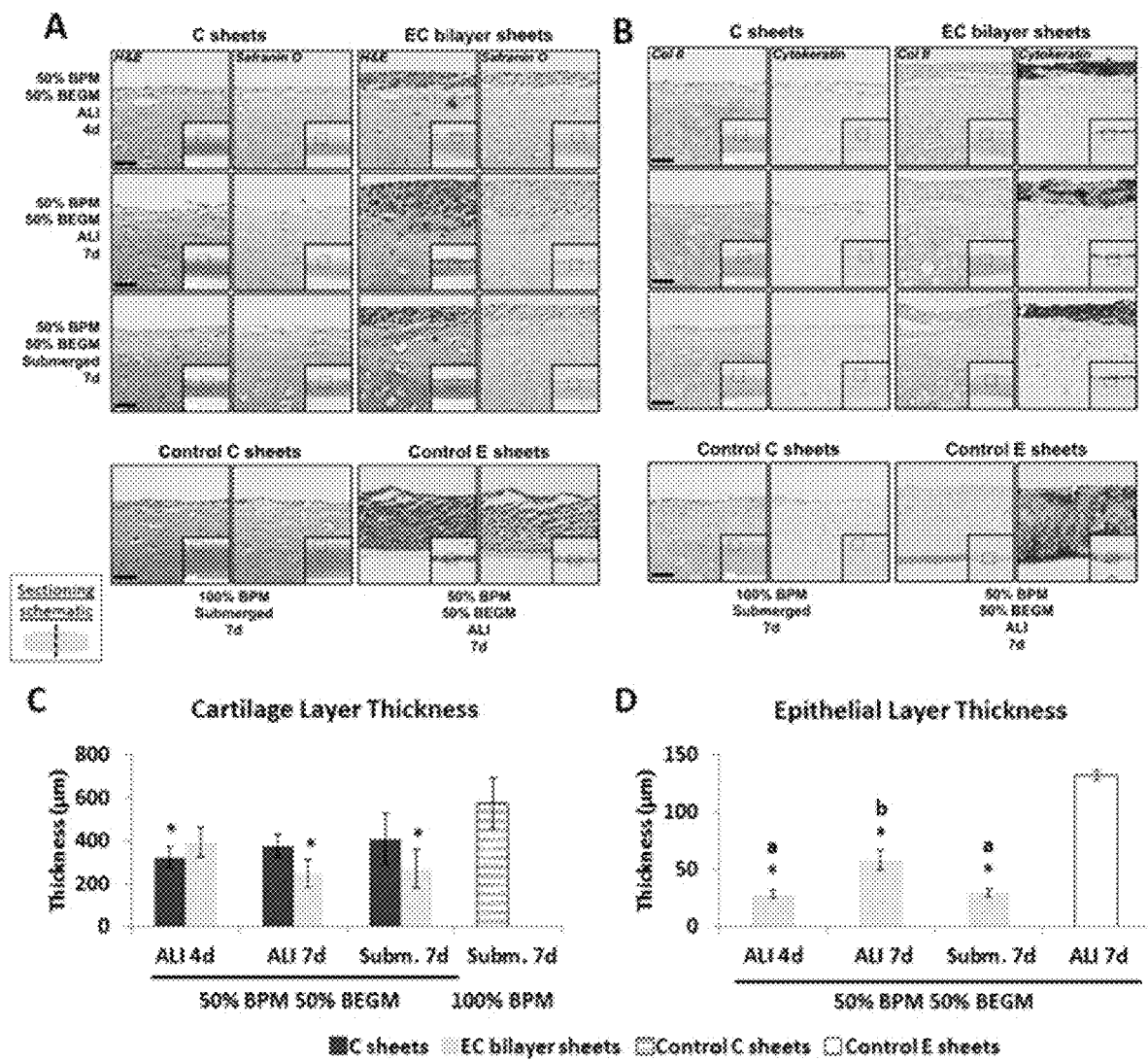
Figs. 19A-D

Figs. 21A-F

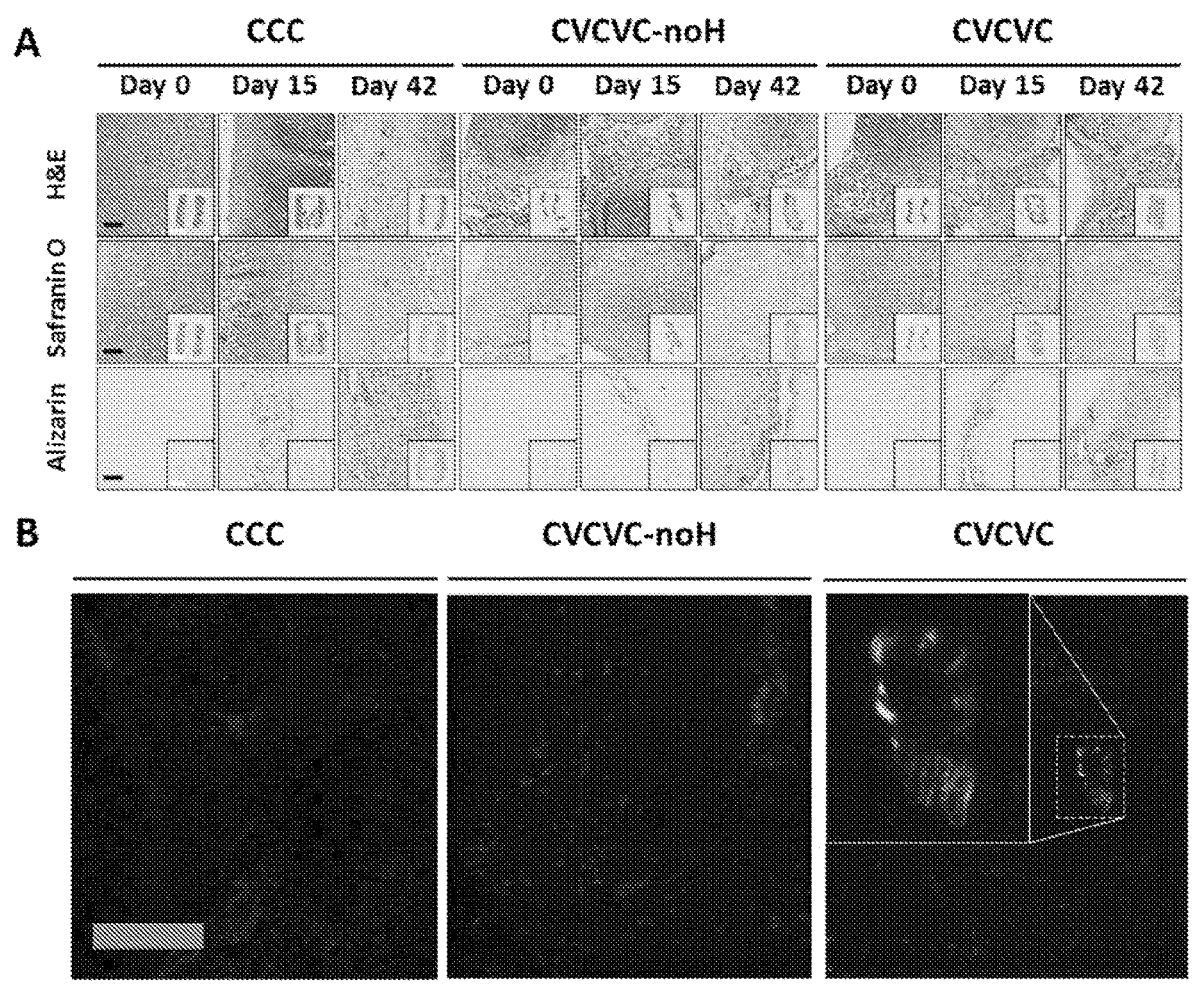
Figs. 23A-B

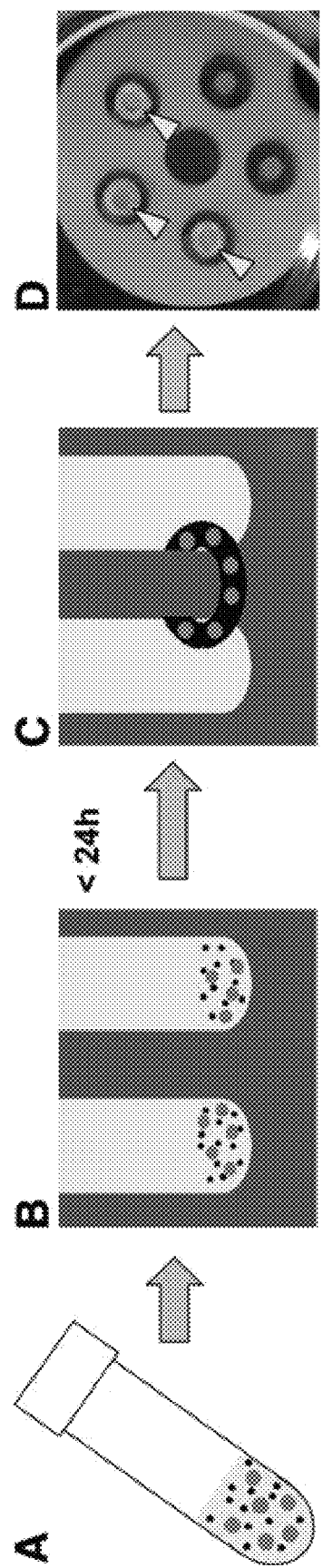
Figs. 24A-D

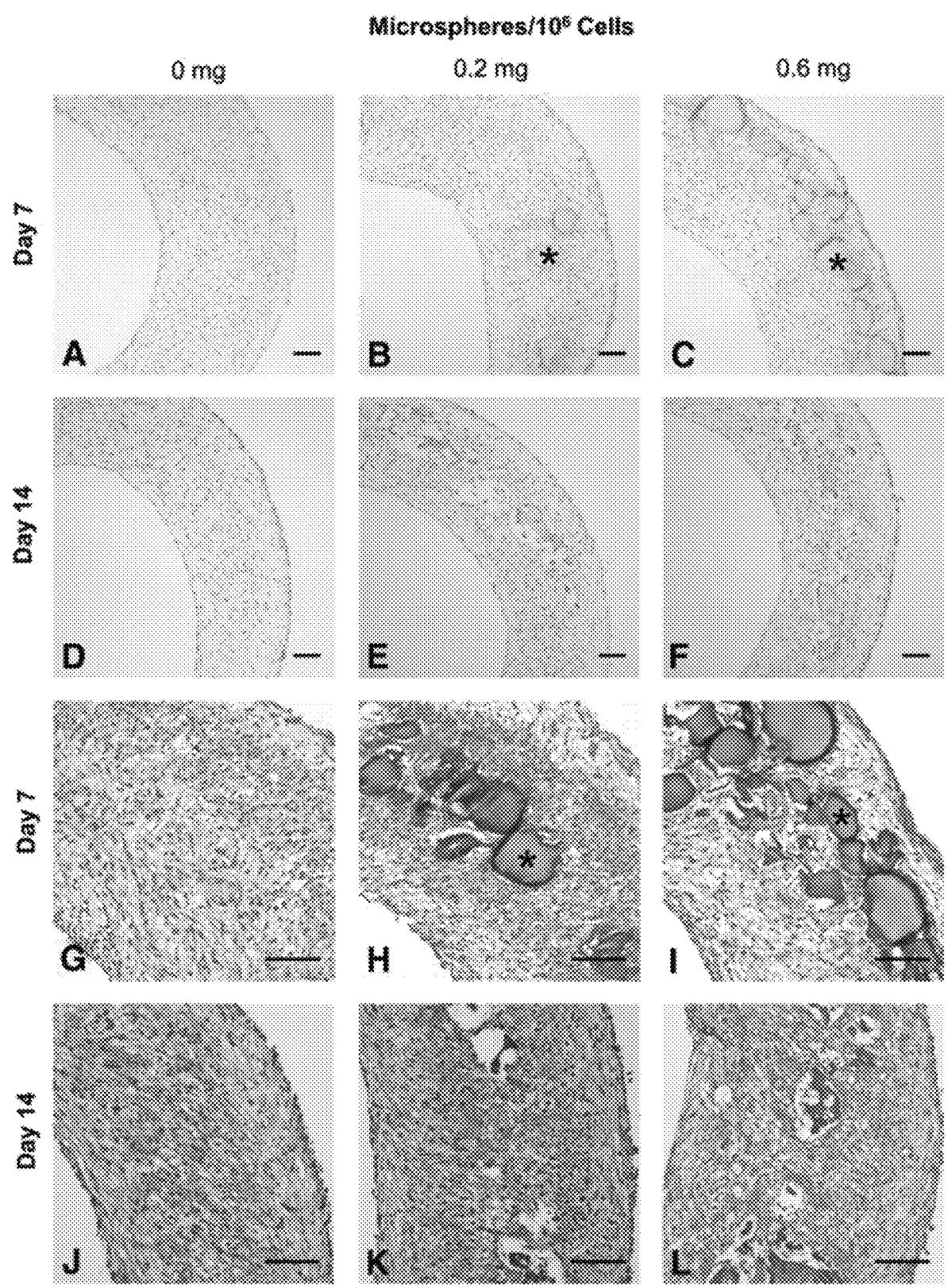
Figs. 25A-L

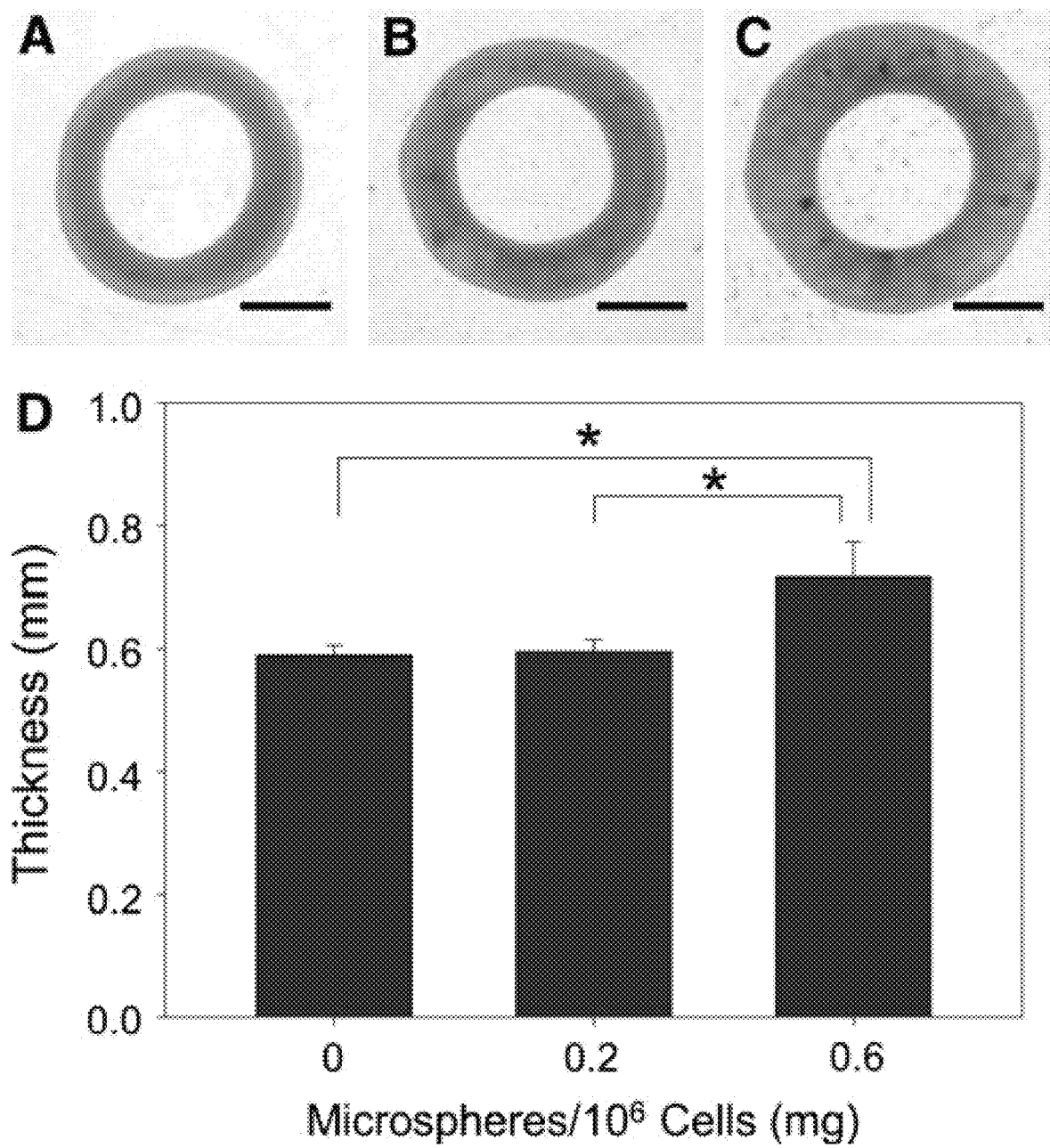
Figs. 26A-D

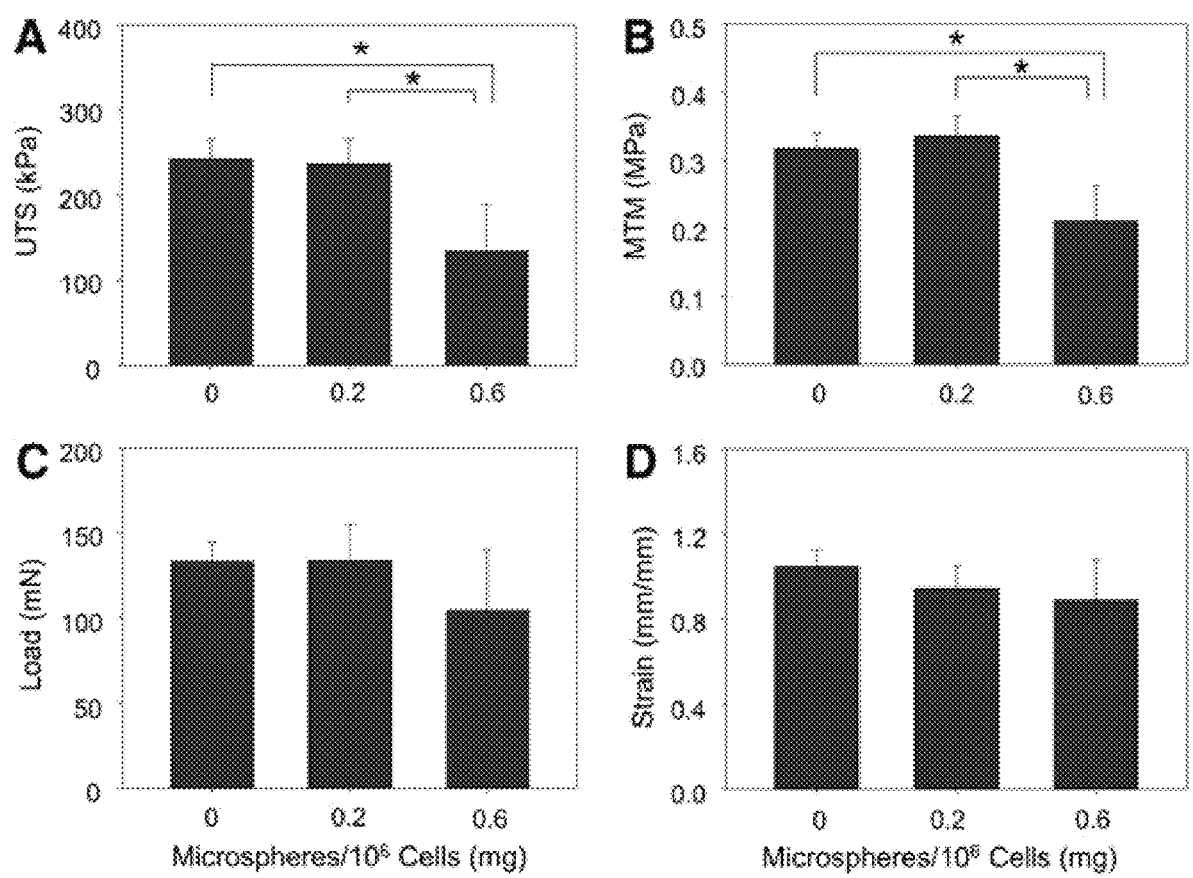
Figs. 27A-D

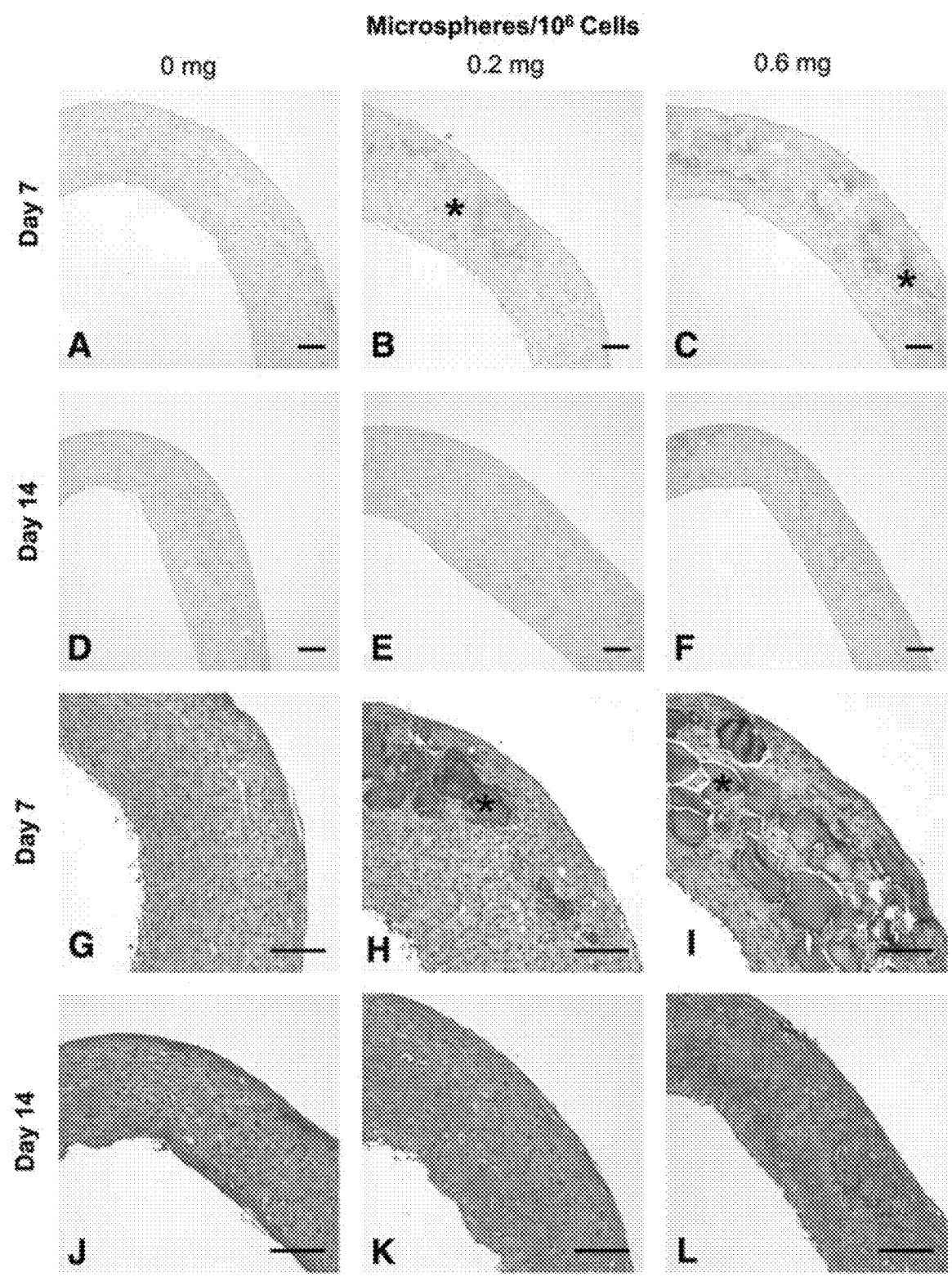
Figs. 28A-L

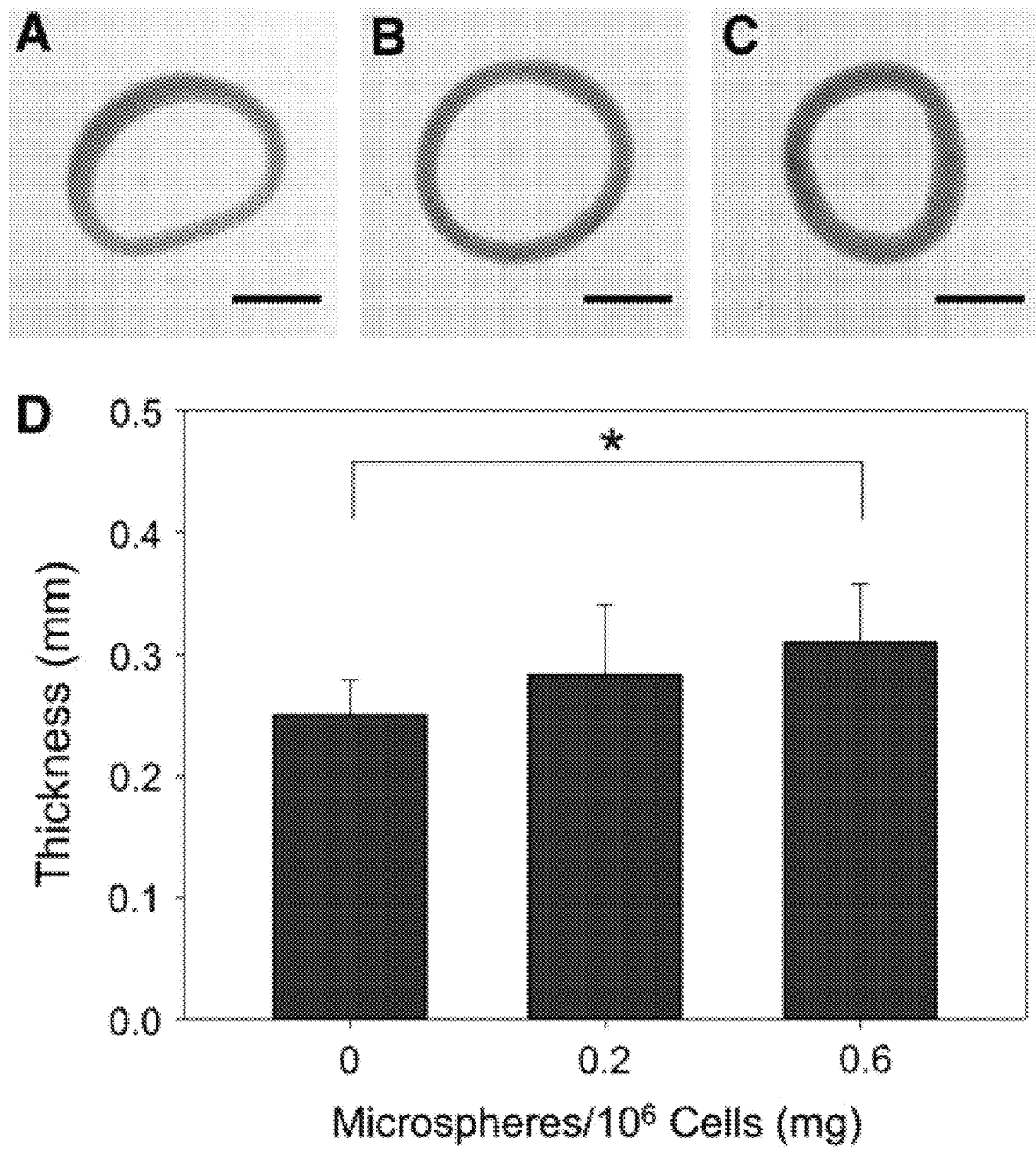
Figs. 29A-D

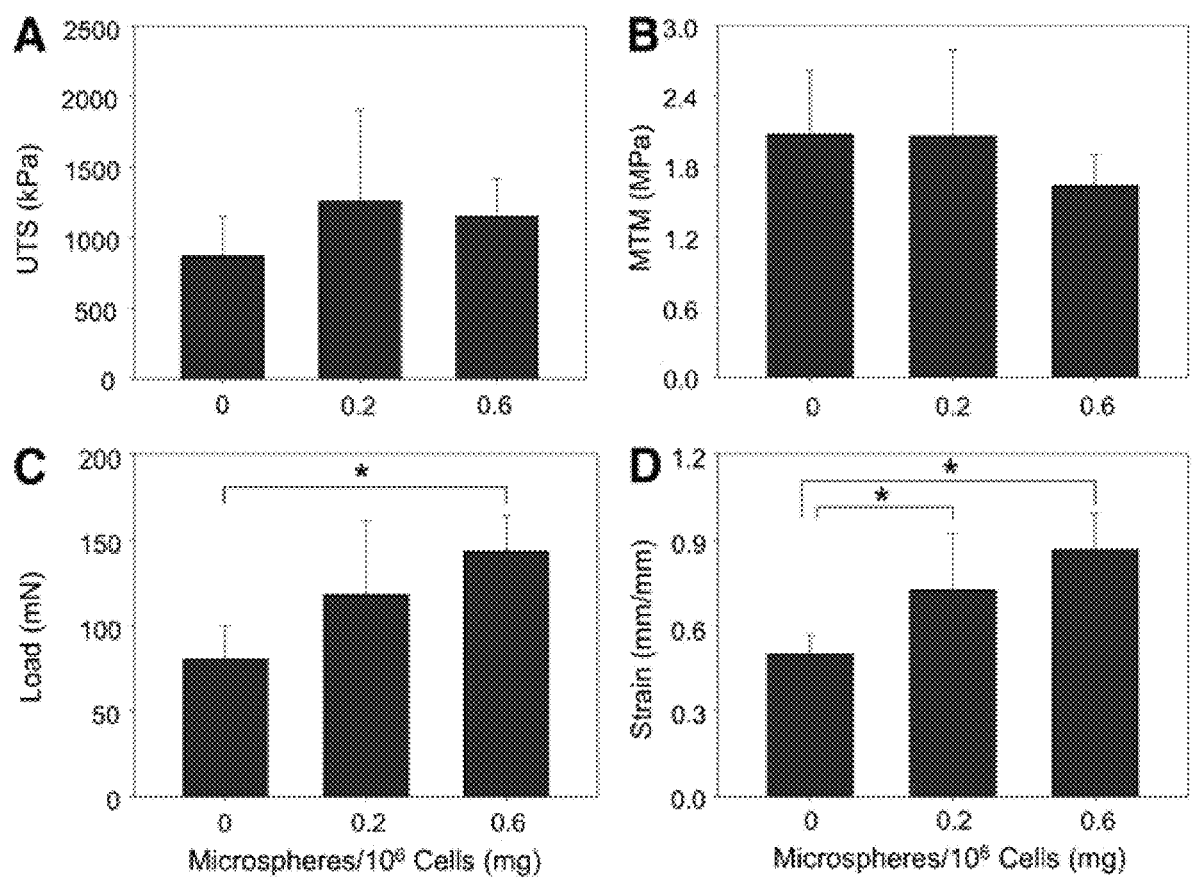
Figs. 30A-D

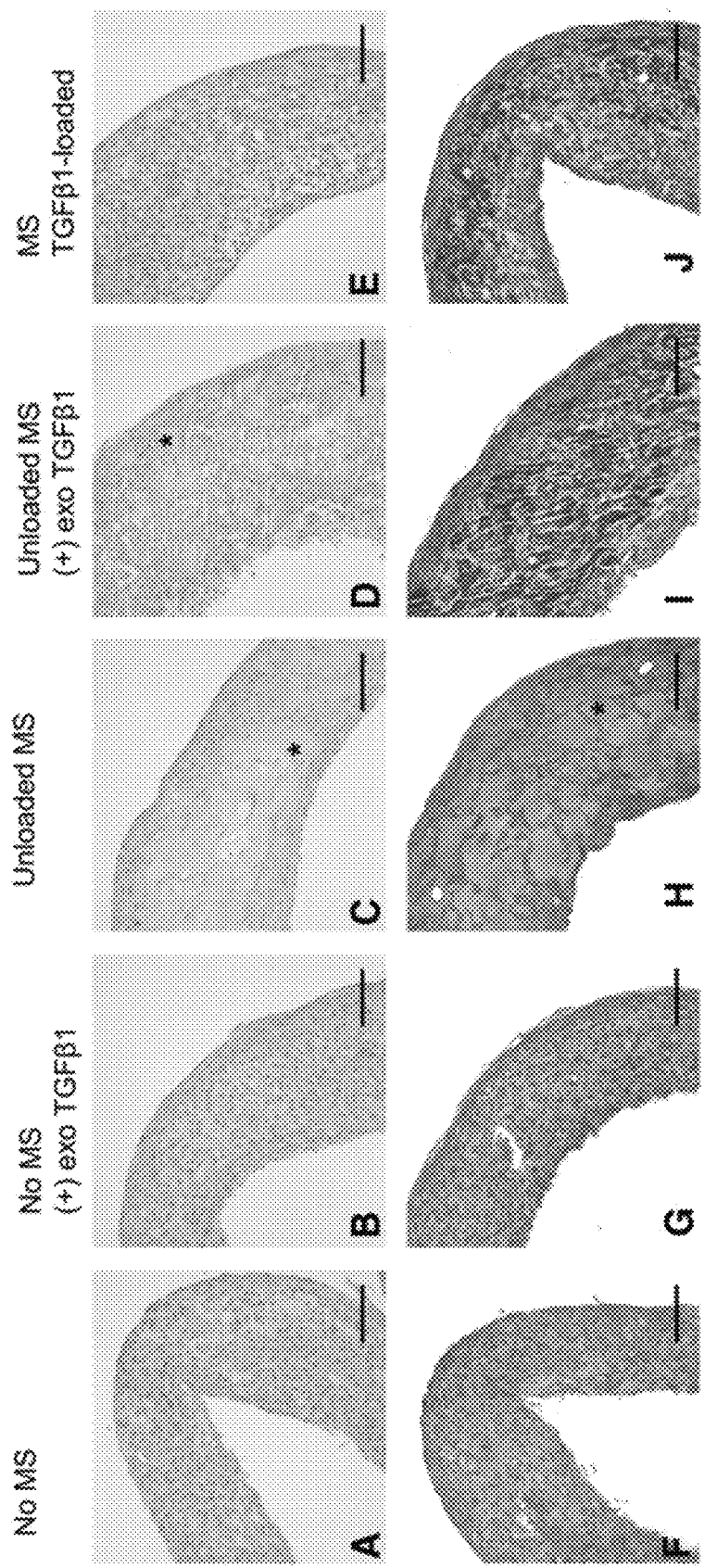
Figs. 31A-J

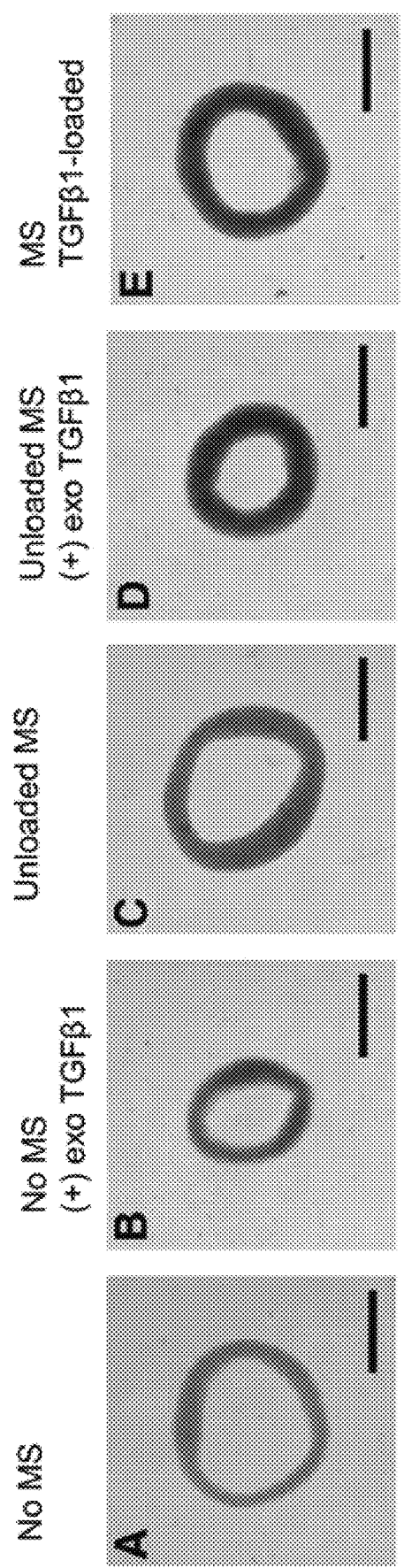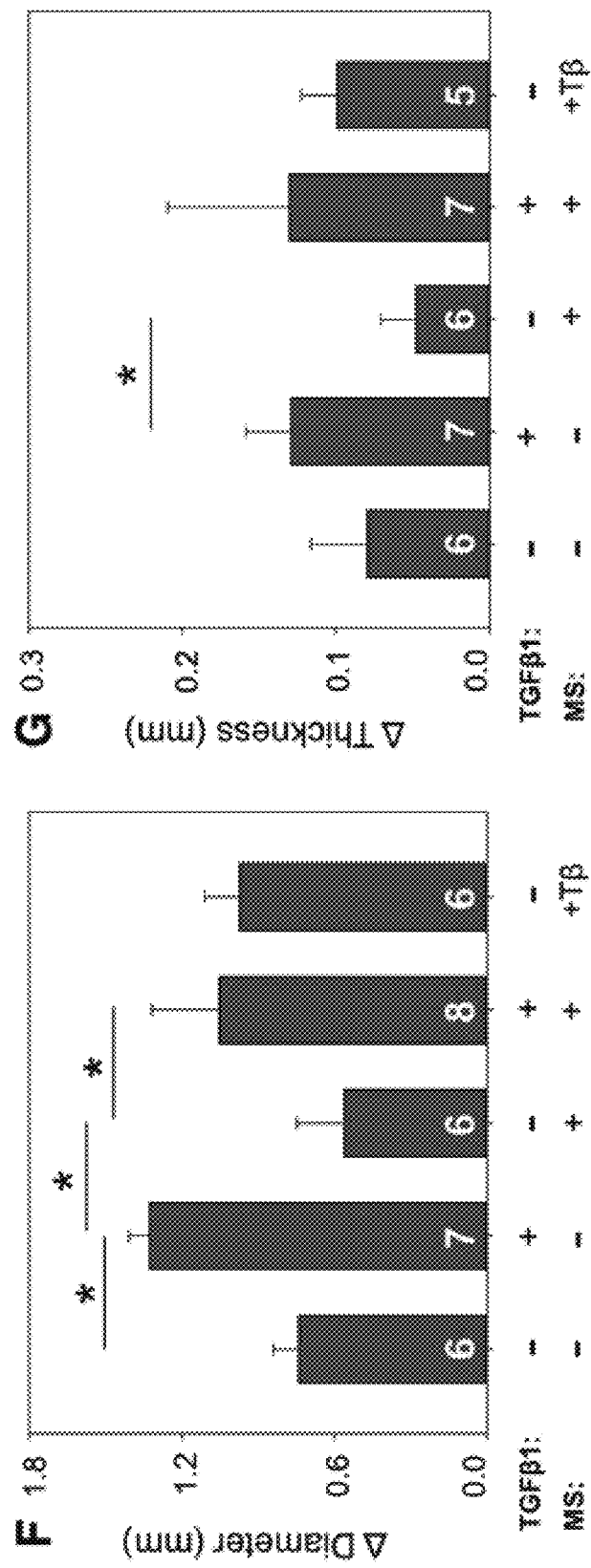
Figs. 32A-G

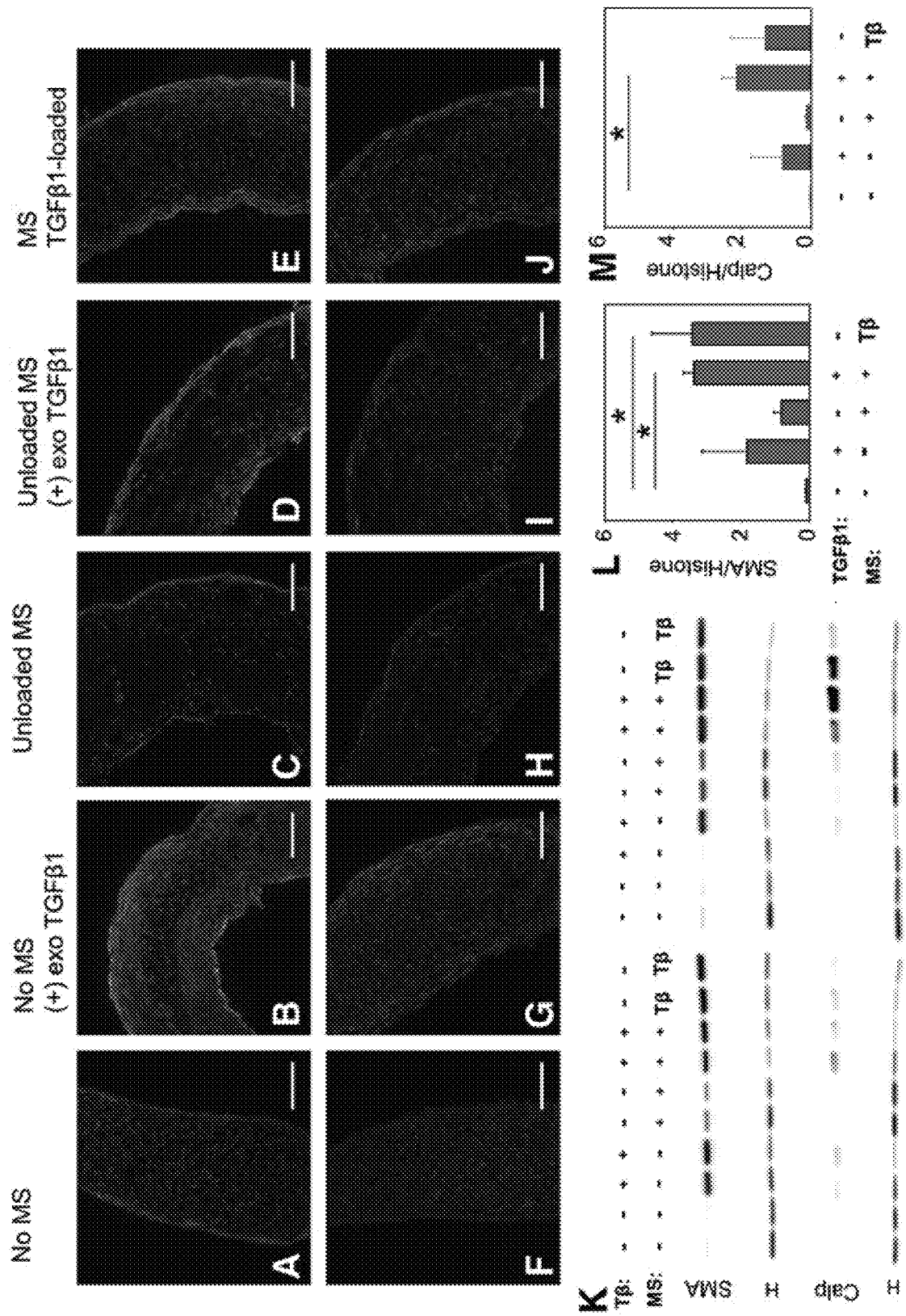
Figs. 33A-M

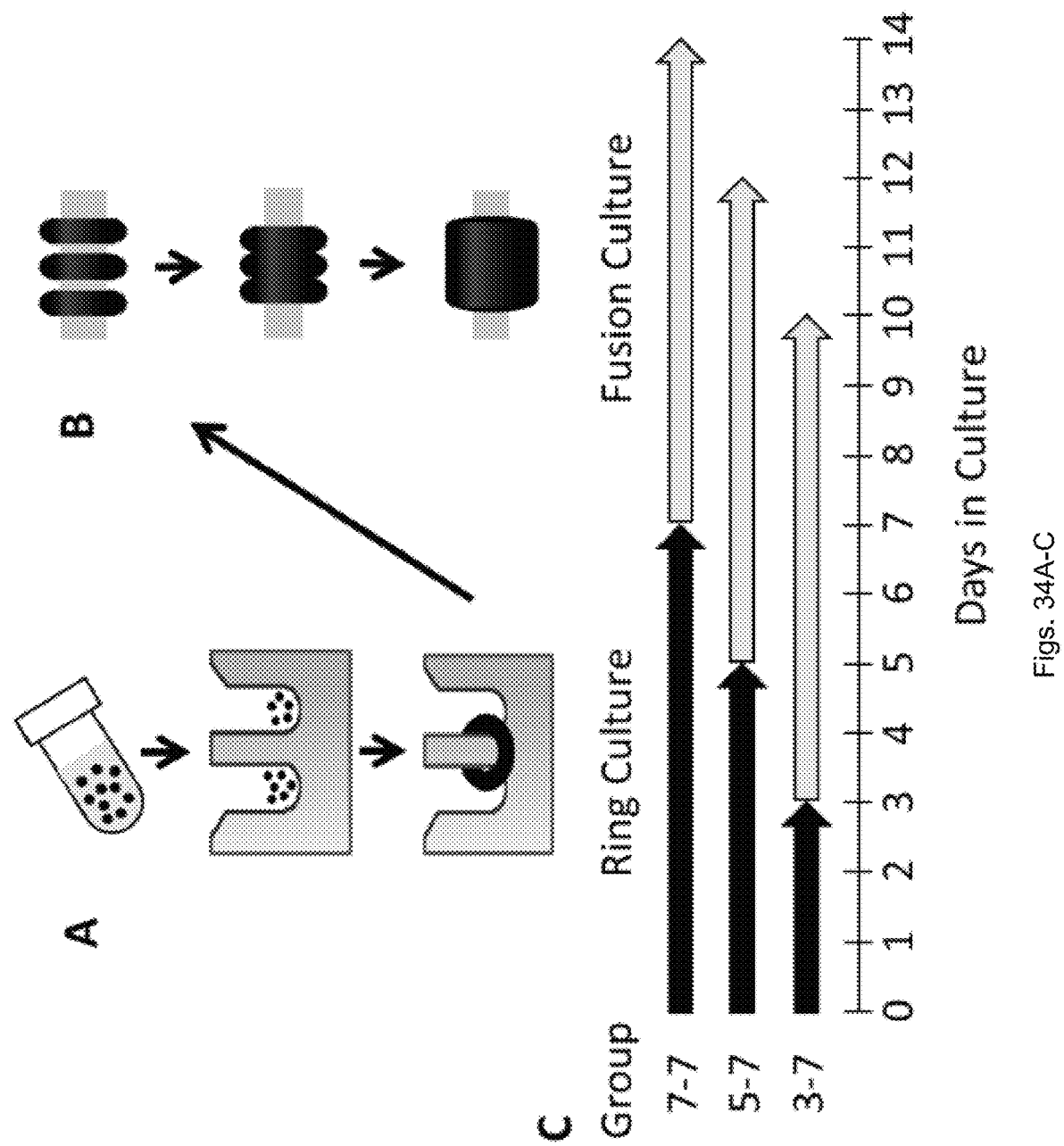
Figs. 34A-C

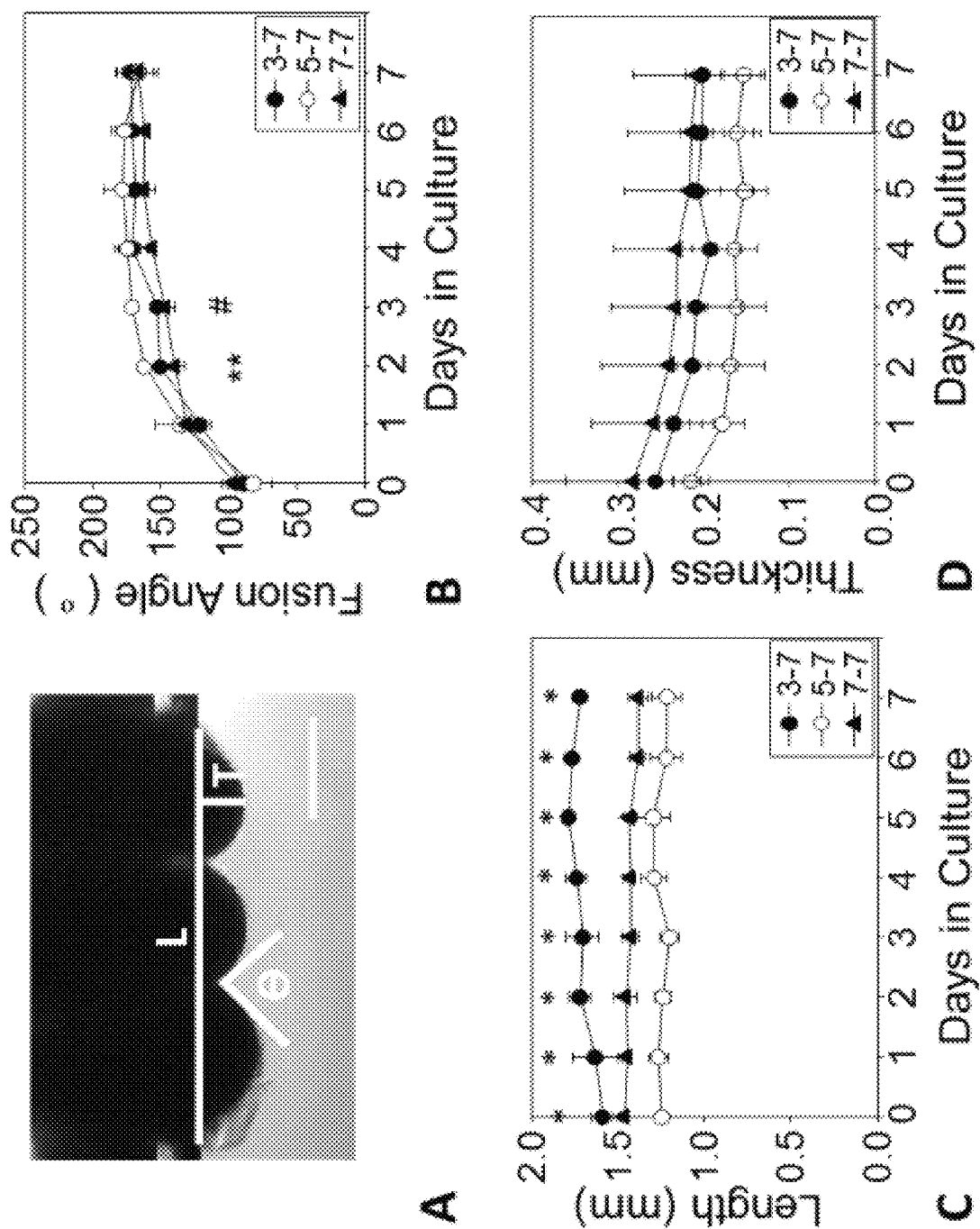
Figs. 36A-D

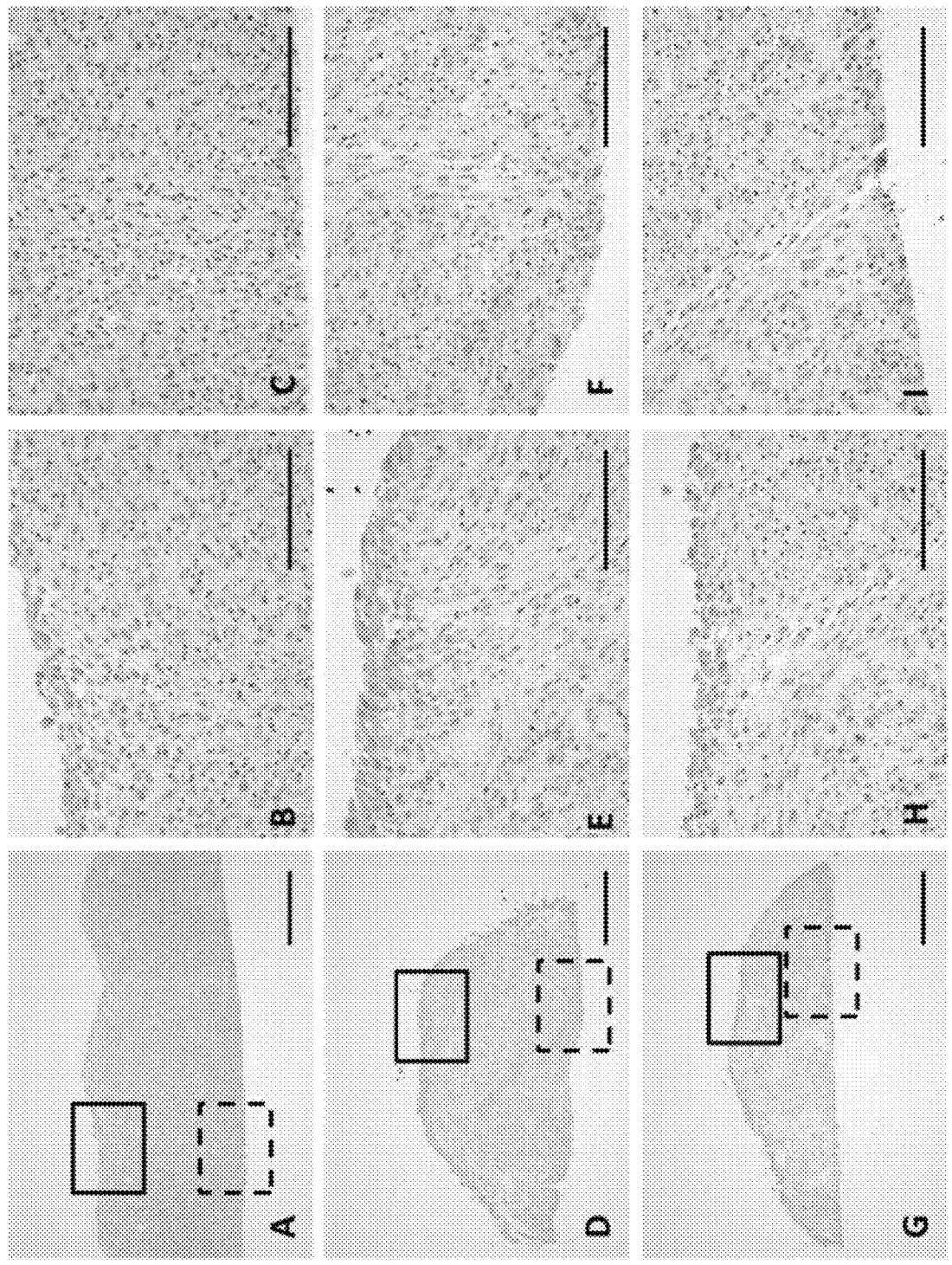
Figs. 37A-I

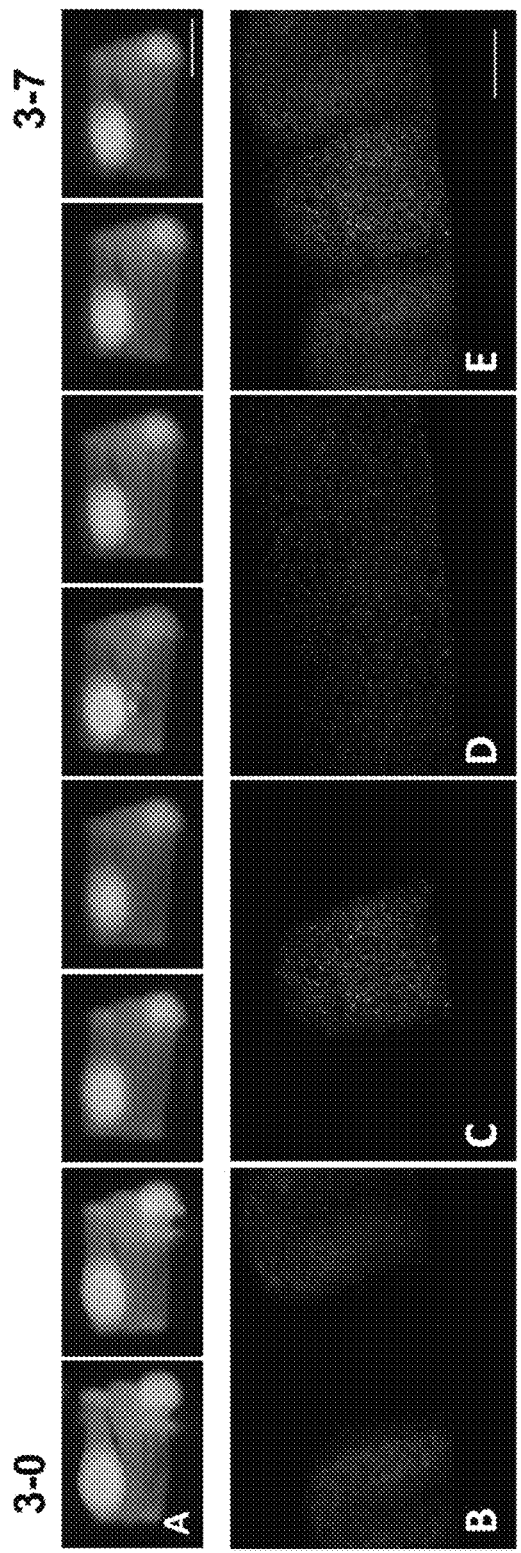
Figs. 38A-E
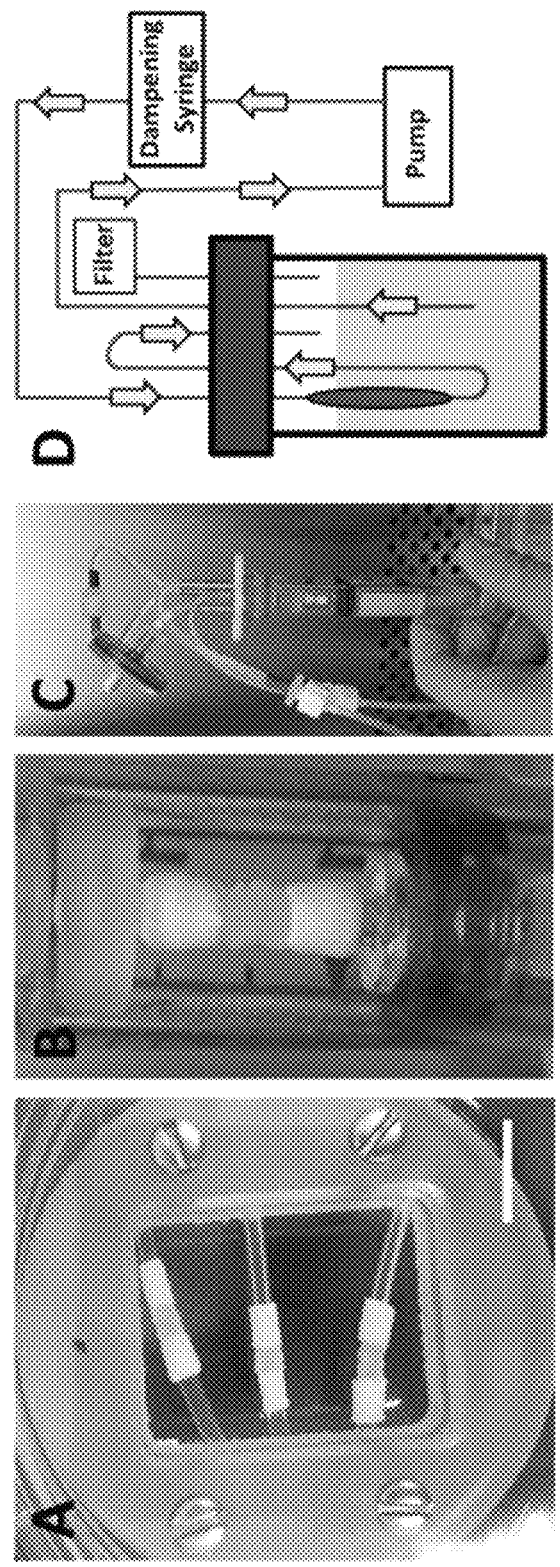
Figs. 39A-D

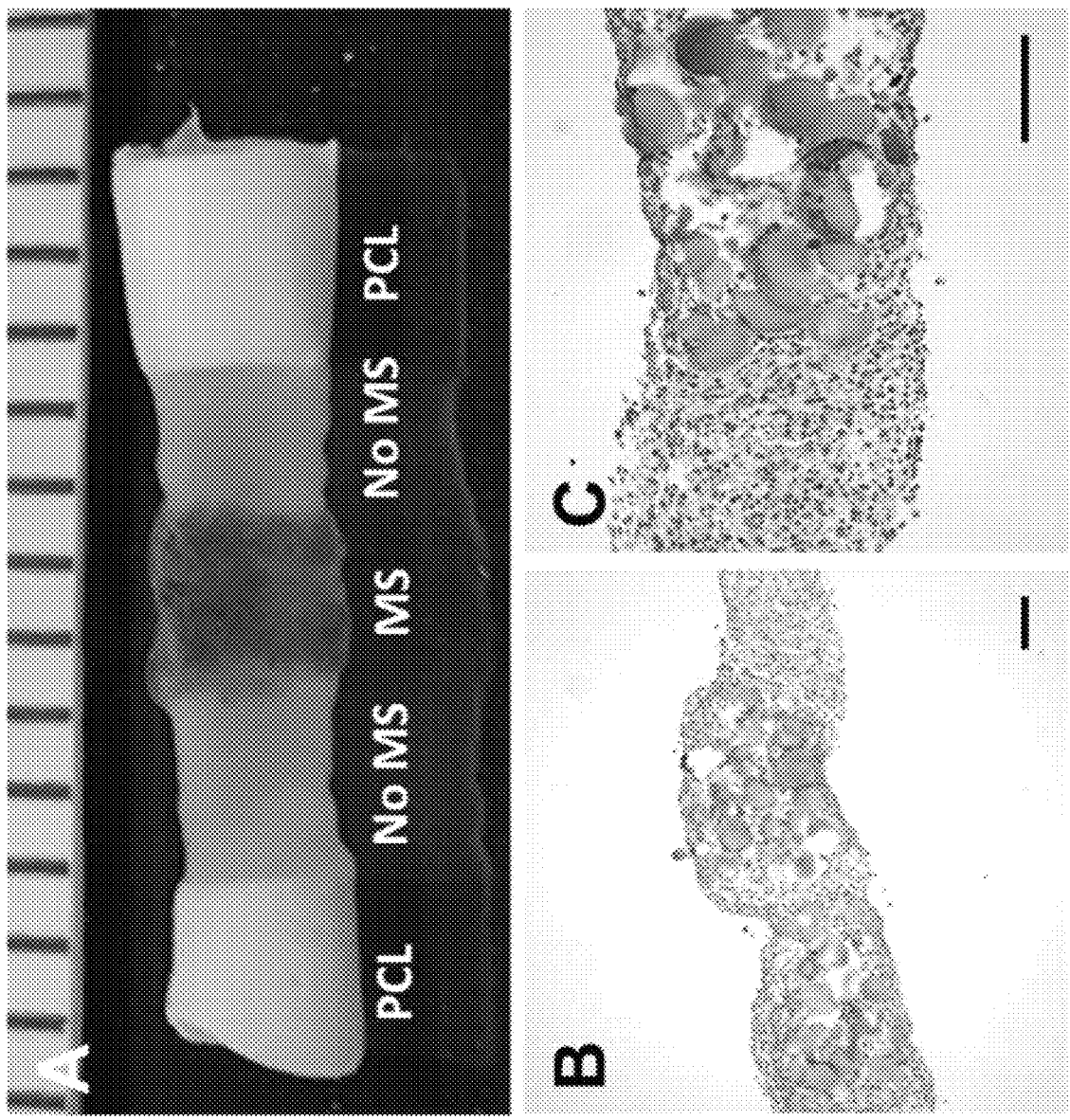
Figs. 40A-C

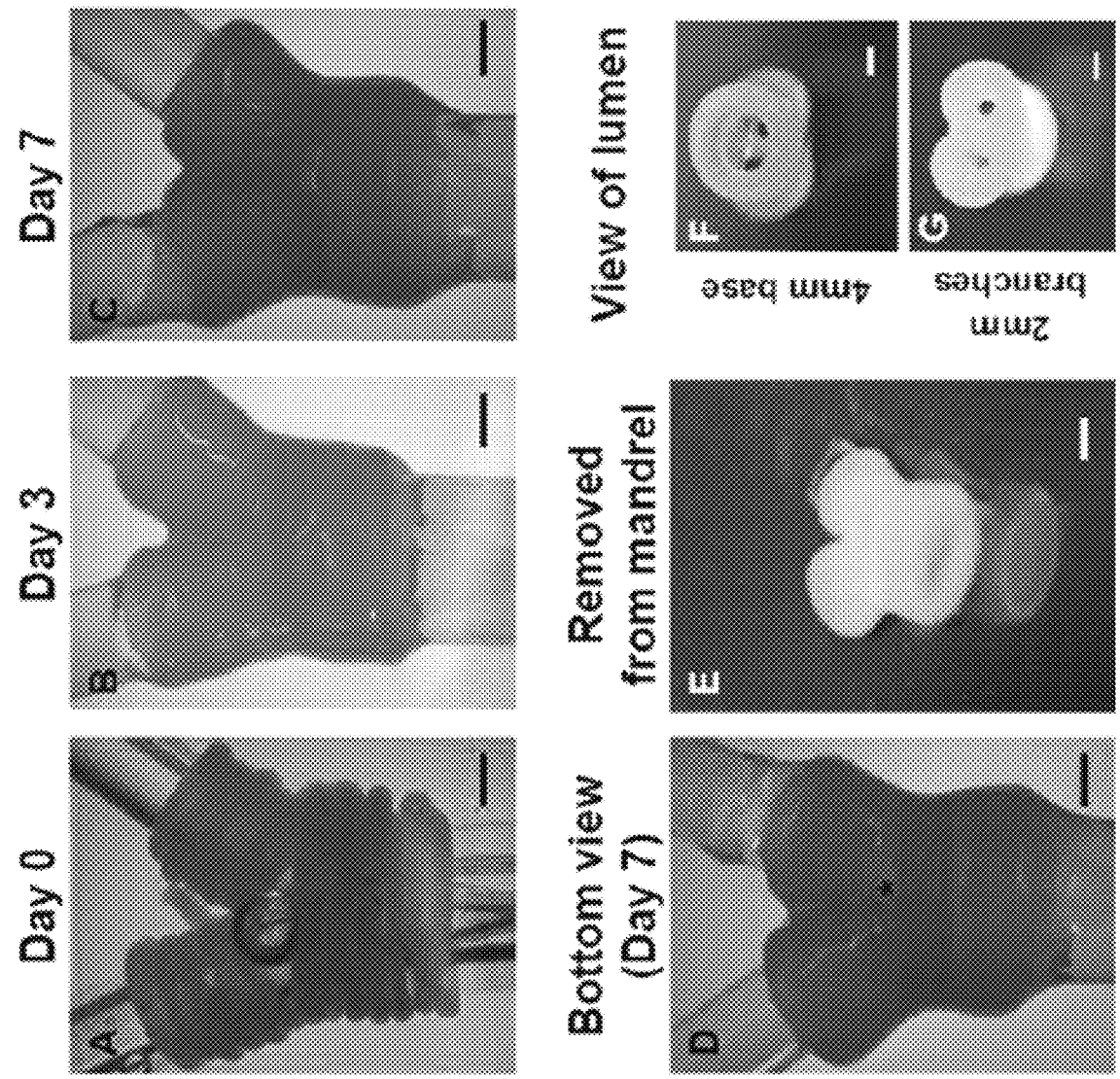
Figs. 41A-G

ENGINEERED TISSUE CONSTRUCTS

RELATED APPLICATION

This application is a Continuation-in-Part of U.S. Ser. No. 15/258,666, filed Sep. 7, 2016. This application also claims priority to U.S. Provisional Application Ser. No. 62/384,400, filed Sep. 7, 2016, the subject matter of which are incorporated herein by reference in their entirety.

GOVERNMENT FUNDING

This invention was made with government support under Grant Nos. R01AR063194, T32AR007505, awarded by The National Institutes of Health, and DGE1144804 awarded by the National Science Foundation. The United States government has certain rights to the invention.

TECHNICAL FIELD

The present application relates to engineered tissue constructs, and systems and methods of forming the engineered tissue constructs.

BACKGROUND

Narrowing or collapse of the trachea is a life threatening condition because stenosis or malacia can prohibit sufficient air transport to the lungs. The most common cause of adult tracheal stenosis is trauma due to prolonged intubation or tracheostomy, but other causes include perichondritis, chondritis, tumor, burns and external trauma. Typically, if the affected portion is less than half the entire length of the trachea in adults or one third in children, the diseased region can be resected and the healthy ends anastomosed during tracheal reconstruction surgery. While short, resectable stenoses are far more common, there are limited treatments available for lengthy tracheal occlusions. Short-term solutions for patients with long segment stenosis include stents, T-tubes, laser surgery and airway dilation. However, a major drawback to these is the need for repetitive treatment: periodic stent and tube replacement due to granuloma formation or additional laser surgery and dilation due to scarring and restenosis. As a result, biomaterial and tissue engineering approaches have been pursued to develop tracheal substitutes. A functional tracheal replacement must first and foremost maintain airway patency during normal breathing. Normally, healthy tracheal cartilage supports the open windpipe. Acellular tracheal prostheses are made of rigid materials and tissue engineered cell-laden technologies are typically cartilaginous structures that are designed to mimic the trachea. A variety of tracheal replacement strategies have been explored, including cell-free artificial prostheses, autografts, native or decellularized allografts which are often seeded with the recipient's cells, and autologous de novo tissue engineered constructs. Despite the broad range of approaches, each has shortcomings. Acellular tracheal prostheses often result in tissue granulation, implant migration, progressive scar tissue formation and restenosis. Autografts and allografts have limited availability, poor mechanical properties, and undergo remodeling upon implantation, often leading to collapse, scarring, and airway occlusion. Allogeneic donor tissue also carries a risk of disease transmission and immunogenicity; recipients of native tissues must be immunosuppressed and extra care must be taken to remove antigens from decellularized tissues. Tissue engineered constructs comprised of autologous cells in scaffolds circumvent immune response issues, but the structural, physical and biochemical properties of the scaffold must be carefully designed to guide cell behavior and neotissue formation. It is also challenging to tune the scaffold degradation rate to match that of cell proliferation and new extracellular matrix (ECM) production, and biomaterial degradation byproducts may hinder tissue healing.

SUMMARY

Embodiments described herein relate to engineered tissue constructs with defined shapes, such as engineered tissue rings, systems and methods of forming modular engineered tissue constructs and to the use of modular engineered tissue constructs in modular tissue assembly systems for tissue repair and bio-artificial tissue engineering applications, such as engineered trachea constructs and engineered vascular constructs. The engineered tissue constructs can include self-assembled, scaffold-free, cell aggregates that are formed by culturing a plurality of cells and nanoparticles and/or microparticles in wells with defined shapes, e.g., rings, disks, or blocks, of a cell culture apparatus or bioreactor. In some embodiments, the self-assembled, cell aggregate can include a population or plurality of cells and plurality of nanoparticles and/or microparticles that are incorporated within the cell aggregate. The nanoparticles and/or microparticles can act as a bulking agent within the cell aggregate to increase the cell aggregate size and/or thickness. Incorporation of the nanoparticles and/or microparticles in the cell aggregate can also improve the mechanical properties of the cell aggregate formed from the cells and nanoparticles and/or microparticles allowing the cell aggregate to be readily manipulated and formed into engineered tissue constructs.

In some embodiments, the nanoparticles and/or microparticles can include at least one bioactive agent that is differentially and/or controllably released by the nanoparticles and/or microparticles. In some embodiments, the bioactive agent can be physically associated with the nanoparticles and/or microparticles and spatially and/or temporally released with a defined release profile from the nanoparticles and/or microparticles.

The engineered tissue constructs can be used in a tissue assembly system to engineer human tissue containing, for example, engineered cartilaginous, vascular, prevascular, muscular, and bone segments. The tissue assembly system can permit fusion of engineered tissue constructs having different properties together to generate modular constructs with multiple types of tissues in a spatially-controlled pattern. Culture of heterogeneous engineered tissue constructs in a hollow organ bioreactor can permit further modification of the constructs, including, for example, epithelialization, of a surface of the construct.

BRIEF DESCRIPTION OF THE DRAWINGS

FIGS. 3(A-D) illustrate images of heterogenous cartilage tube with cartilaginous and non-cartilaginous portions. Chondrogenesis was induced in hMSC rings for (A-B) 5 days or (C-D) 12 days. SMC rings were cultured for (A-B) 10 days or (C-D) 5 days. Alternating hMSC and SMC rings were fused into (A-B) 10-ring tubes over 7 days or (C-D) 4-ring tubes over 8 days. (A) Fluorescence (hMSC labeled with red cell tracker dye) and (B) brightfield images of hMSC-SMC tubes. (C) hMSC-SMC tube after 8 days of fusing. (D) Cross-section of hMSC-SMC tube stained with Safranin 0/Fast Green for GAG (lumen is on bottom). Scale bars: white=1 mm, black=500 µm.

FIG. 4 is a schematic of tissue ring and tube assembly processes. A suspension of MSCs with growth factor loaded microspheres ("hMSC+MS") was seeded in custom agarose wells and cultured in basal pellet media. Cell only tissues ("hMSC"), which did not contain microspheres, were seeded and cultured in basal pellet media supplemented with TGF-β1. On day 2 of culture, rings (tan) were removed from the culture wells using tweezers and were stacked on silicone tubes (gray) to form 3- and 6-ring tubes.

FIG. 5 illustrates a light photomicrograph of crosslinked gelatin microspheres.

FIGS. 6(A-D) illustrate macroscopic images of cartilage tissue rings and tubes in culture. Tissue rings were formed by seeding a suspension of (A) hMSCs or (C) hMSCs with microspheres in custom designed agarose annular wells (white dotted outline) with 2 mm posts (black dotted outline). (B, D) On Day 2, some of the rings were stacked on silicone tubes, which were clamped in a custom designed holder, to form 3-ring (white arrow) or 6-ring (black arrow) tissue tubes. MS=Microspheres.

FIGS. 7(A-G) illustrate gross macroscopic pictures of (A-C) hMSC-only cartilage rings and tubes, (D-F) microsphere-containing rings and tubes, and (G) native rat trachea. (A, B, D, E) Rings and 3-ring tubes are shown in replicates. (C, F, G). A representative hMSC or hMSC+MS 6-ring tube and a rat trachea are presented from multiple perspectives. MS=Microspheres. Scale bar is 2 mm.

FIGS. 8(A-C) illustrate (A) DNA content, (B) GAG content, and (C) GAG normalized to DNA in harvested rings and 3-ring cartilage tubes. MS=Microspheres. Groups that do not share the same letter are significantly different (p<0.01).

FIGS. 9(A-E) illustrate photomicrographs of Safranin O/Fast Green stained tissue engineered (A, C) cartilage rings and (B, D) cartilage tubes composed of (A, B) hMSCs-only and (C, D) hMSCs+MS, and (E) rat trachea in axial and vertical planes. Remnant gelatin microspheres (black arrows) are visible in hMSC+MS tissues. MS=Microspheres; F=axial plane; z=vertical plane; black scale bars=500 mm; white scale bars=100 mm.

FIGS. 10(A-D) illustrate photomicrographs of Collagen Type II/Fast Green stained tissue engineered (A, C) cartilage rings and (B, D) cartilage tubes composed of (A, B) hMSCs-only (A, B) and (C, D) hMSCs+MS in axial and vertical planes. Type II collagen rich tissues are red. MS=Microspheres; F=axial plane; z=vertical plane; black scale bars=500 mm; white scale bars=100 mm.

FIGS. 11(A-B) illustrate ring thicknesses (A) and tube outer diameters (B) measured in cartilage tissue engineered rings and tubes, and rat tracheas. MS=Microspheres. Groups that do not share a letter are significantly different (p<0.05).

FIGS. 12(A-D) illustrate mechanical analysis of tissue engineered cartilage rings and tubes, and rat tracheas. (A) Ring maximum load at failure and (B) ultimate tensile stress during uniaxial testing (A, inset); (C) tube load at 80% collapse and (D) % recoil after luminal collapse (C, inset). MS=Microspheres. Groups that do not share the same letter are significantly different (p<0.05).

FIG. 13 is an image showing repeated manual compression and release of a representative hMSC tube, hMSC+MS Tube and a section of a rat trachea. MS=Microspheres.

FIGS. 14(A-B) illustrate images showing gross morphology of hMSC rings and tubes. Representative rings (2-mm) and tubes (3×2-mm and 8×2-mm) of A) hMSCs alone or B) hMSCs+GM+MCM cultured for 5 weeks in chondrogenic+exogenous TGF-β1 (2 weeks; 10 ng/ml) and osteogenic+BMP-2 (3 weeks; 100 ng/ml) induction media. Scale bar=2 mm.

FIGS. 15(A-F) illustrate graphs showing the thickness and length analyses of hMSC osteogenic or bone rings and tubes generated using the methods described herein. A, B) 2-mm rings (N=4), C,D) 3×2-mm tubes (N=2), E,F) 8×2-mm tubes (N=1). hMSCs alone or hMSCs+GM+MCM cultured for 5 weeks in chondrogenic+exogenous TGF-β1 (2 weeks; 10 ng/ml) and osteogenic+BMP-2 (3 weeks; 100 ng/ml) induction media.

FIGS. 16(A-D) are a schematic overview of the cartilage (A-B), epithelial-cartilage (C) and prevascular-cartilage and tri-tissue (D) engineering components aimed toward the generation of a multi-tissue tracheal construct for airway repair.

FIGS. 17(A-J) illustrate an analysis of tissue engineered cartilage rings formed with different cell numbers. (A) Macroscopic images of rings were acquired, GAGs were stained with Safranin 0, immunohistochemistry was performed for human type II collagen and the frequency of tissue engineered cartilage ring formation with varied cell number were reported compared to rat trachea. Black scale bars are 200 µm; white scale bars are 2 mm. Images in a single row are the same magnification. (B) Ring thickness was measured in tissue engineered hMSC (light gray) and hMSC+MS (dark gray) cartilage rings (N=3) and compared to rat tracheal segments (black, N=4). (C) Construct wet weight, (D) GAG content, (E) DNA content, (F) GAG normalized to DNA, (G) GAG normalized to tissue wet weight and (H) DNA normalized to tissue wet weight were acquired from cartilage rings (N=3-4) and, for (F), (G) and (H), rat tracheal segments (N=4). (I) Failure load during pull-to-failure uniaxial testing (pictured in I, inset) and (J) ultimate tensile strength (UTS; load normalized by area) were measured in engineered rings (N=3) and compared to rat tracheal segments (black, N=4). MS=microspheres. a,b,c,d: hMSC groups without common letter differ (p<0.05); 1, 2, 3, 4: hMSC+MS groups without common number differ (p<0.05); #: significantly different than hMSC group (p<0.05); *: rat trachea is significantly different compared to all other groups (p<0.05); R: significantly different than rat trachea (p<0.05). Data shown as mean±SD.

FIGS. 18(A-J) illustrate macroscopic and histological images, and biochemical and mechanical analysis of cartilage tubes of 2, 6 and 12 mm inner diameters and the frequency of formation of tissue engineered rings used to make cartilage tubes. (A) Macroscopic images of tubes were acquired, GAGs were stained with Safranin O (pink/red), immunohistochemistry was performed for human type II collagen and the frequency of ring formation of 2, 6 and 12 mm inner diameter cartilage tubes was recorded. Tissue tubes were cut to show transverse and longitudinal sections. Black scale bars are 200 µm; white scale bars are 4 mm. Images without scale bars in a single row are the same magnification. (B) Tube wall thickness was measured in 5-ring engineered cartilage tubes (gray, N=3) and compared to rabbit tracheal segments (black, N=6). (C) Construct wet weight, (D) GAG content, (E) DNA content, (F) GAG normalized to DNA, (G) GAG normalized to tissue wet weight and (H) DNA normalized to tissue wet weight were acquired from tissue engineered 2-ring cartilage tubes (N=4-5). (I) Load required to collapse 80% of the 5-ring engineered tube lumen diameter and (J) tube recoil after luminal compression (I inset) were measured (N=3) and compared to rabbit tracheal segments (black, N=6). MS=microspheres. a,b,c: hMSC+MS groups without common letter differ ($p<0.05$); *: rabbit trachea is significantly different compared to all other groups ($p<0.05$). MS=microspheres. Data shown as mean±SD.

FIGS. 19(A-D) illustrate histologic staining and thickness measurements of epithelialized cartilage sheets and controls. Epithelial-cartilage bilayer sheets and controls were stained with (A) Hematoxylin & Eosin, Safranin O for GAG and (B) anti-type II collagen and anti-cytokeratin (red) for epithelial cells. ALI=sheets cultured at air liquid interface for 4 or 7 days; submerged=sheets cultured submerged in media for 7 days. BPM=chondrogenic basal pellet media; BEGM=bronchial epithelial growth media. Black scale bars are 40 µm; white scale bars are 200 µm. Images without scale bars in a single row are the same magnification. (C) Cartilage layer thickness and (D) epithelial layer thickness were measured from histological images of cartilage (C) sheets (dark gray and patterned (control)), epithelial (E) sheets (white (control)) and epithelial-cartilage (EC) bilayers (light gray) (N=3). ALI=sheets cultured at air liquid interface for 4 or 7 days; Subm.=sheets cultured submerged in media for 7 days. BPM=chondrogenic basal pellet media; BEGM=bronchial epithelial growth media. *: significantly different compared to control cartilage sheets in (C) and control epithelial sheets in (D) ($p<0.05$); a,b,c: Bilayer sheets without common letter differ ($p<0.05$). Data shown as mean±SD.

FIGS. 23(A-B) illustrates histologic staining of tracheal tubes implanted subcutaneously in mice. Three types of tubes (CCC, CVCVC-noH and CVCVC) were implanted subcutaneously in mice for 0, 15 or 42 days. (A) Longitudinal sections were stained with H&E, Safranin O with a Fast Green counterstain and alizarin red S. (B) Tissue sections from day 42 samples were counterstained with DAPI and visualized for fluorescent FITC-UEA-1 perfusion staining. Inset in (B) CVCVC group is 3× magnification of image.

FIGS. 24(A-D) is a schematic of microsphere incorporation within self-assembled tissue rings. (A) Gelatin microspheres (purple circles) were mixed in suspension with SMCs (black dots) at 0, 0.2, or 0.6 mg/$10^6$ cells. (B) Cells and microspheres were seeded into agarose molds. (C) Cells aggregate to form self-assembled rings with incorporated microspheres. (D) Photograph of an agarose mold with aggregated human SMC-microsphere rings. Arrowheads point to rings on agarose posts. SMC, smooth muscle cell.

FIGS. 25(A-L) illustrate gelatin microsphere incorporation within rings. SMC rings were seeded with 0, 0.2, or 0.6 mg/$10^6$ cells and cultured for 7 or 14 days in growth medium before harvesting for histological analysis. Hematoxylin and eosin (A-F) and Picrosirius Red/Fast Green stain [(G-L)]. Example microspheres marked with asterisks. Scale=100 mm.

FIGS. 26(A-D) illustrate the effects of microsphere incorporation on thickness of rings cultured in growth medium. Images of rings seeded with (A) 0, (B) 0.2, or (C) 0.6 mg/$10^6$ cells and cultured in growth medium for 14 days and (D) their average wall thicknesses. Scale=1 mm, n=6, *$p<0.05$. Values are mean–SD. SD, standard deviation.

FIGS. 27(A-D) illustrate mechanical properties of 14-dayold rings cultured in growth medium. Mean values for (A) UTS, (B) MTM, (C) failure load, and (D) failure strain were calculated for each ring sample. n=6, *$p<0.05$. Values are mean–SD. UTS, ultimate tensile stress; MTM, maximum tangent modulus.

FIGS. 28(A-L) illustrate microsphere incorporation in rings cultured in differentiation medium. Rings were seeded with 0, 0.2, or 0.6 mg/106 cells, harvested at 7 or 14 days, and stained with (A-F) hematoxylin and eosin and (G-L) Picrosirius Red/Fast Green stain (red=collagen, green=counterstain). Example microspheres marked with asterisks. Scale=100 mm.

FIGS. 29(A-D) illustrate the effects of microsphere incorporation on thickness of rings cultured in differentiation medium. Images of rings seeded with (A) 0, (B) 0.2, or (C) 0.6 mg/$10^6$ cells and cultured for 14 days and (D) their average wall thicknesses. Scale=1 mm; n=8 for the 0 mg group; n=9 for the 0.2 and 0.6 mg/$10^6$ cells groups, *$p<0.05$. Values are mean–SD.

FIGS. 30(A-D) illustrate mechanical properties of 14-day old rings with incorporated microspheres cultured in differentiation medium. Mean values for (A) UTS, (B) MTM, (C) failure load, and (D) failure strain were calculated from stress-strain curves for each ring sample. n=6, *$p<0.05$. Values are mean–SD.

FIGS. 31(A-J) illustrate microsphere incorporation in TGF-b1-treated rings. (A, F) Control (untreated) rings. (B, G) Rings without microspheres cultured with exogenous TGF-b1 (10 ng/mL). Rings with unloaded microspheres are (C, H) untreated or (D, I) treated with exogenous TGF-β1. (E, J) Rings with TGF-b1-loaded microspheres but without exogenous TGF-β1. (A-E) Hematoxylin and eosin stain and (F-J) Picrosirius Red/Fast Green stain, (F-J; red=collagen, green=counterstain). Example microspheres marked with asterisks. Scale=100 mm. TGF-β1, transforming growth factor beta 1.

FIGS. 32(A-G) illustrate the effect of TGF-b1 treatment on ring morphology. (A) Untreated control ring with no microspheres. (B) Ring treated with 10 ng/mL exogenous (exo) TGF-β1. (C, D) Ring with unloaded gelatin microspheres either (C) untreated or (D) treated with exogenous TGF-β1. (E) Ring with TGF-b1-loaded microspheres. Change in (F) inner diameter and (G) ring thickness after removal from agarose posts. Scale=1 mm, *p<0.05. Values are mean–SD, sample size for each group shown on bars.

FIGS. 33(A-M) illustrate smooth muscle contractile protein expression in rings treated with TGF-β1. (A, F) Control (untreated) rings. (B, G) Rings without microspheres cultured with exogenous TGF-β1 (10 ng/mL). Rings with unloaded microspheres (C, H) untreated or (D, I) treated with exogenous TGF-β1. (E, J), Rings with TGF-β1-loaded microspheres. Rings were stained for either (A-E) smooth muscle alpha actin or (F-J) calponin. Scale=100 mm. Corresponding western blots are shown below (K), with histone (H) loading control shown below each protein. Densitometry analysis is shown of smooth muscle alpha actin (L) and calponin (M) normalized to histone. Lanes are marked as with or without exogenous TGF-β1 (Tb) and with or without microspheres (MS). Loaded MS are marked as with Tb. N=4, *p<0.05 (one-way analysis of variance on ranks, Dunn's post hoc analysis).

FIGS. 34(A-C) are a schematic of tube fabrication process, and tissue tube culture experimental groups for the ring pre-culture duration experiment. Rings are formed by seeding SMCs into a ring-shaped agarose mold, where cells aggregate around 2 mm diameter posts and form rings in less than 24 hrs (A). Rings are then removed from molds and threaded onto silicone tubing, where they are pushed together and cultured for 7 additional days to allow fusion (B). To test the effects of varying ring culture duration, rings were cultured for 3, 5, or 7 days ("ring culture"), followed by 7 days of fusion culture for all groups (C). Groups are labeled as: days in ring culture—days in fusion culture (ex. Group 3-7=3 days in ring culture followed by 7 days in fusion culture). Black dots=SMCs.

FIGS. 36(A-D) illustrate fusion kinetics of human SMC rings. Three human SMC rings threaded onto silicone tubing mandrels (A). The angle between rings (e), length (L), and thickness (T) were measured for each sample on each day of culture (A). Fusion angles (B), tube length (C) and thickness (D) as a function of time for tubes fabricated from rings cultured for 3 (3-7), 5 (5-7) or 7 (7-7) days prior to 7 days as tubes. N=3 tubes per group. Data points are mean±SD. #p<0.05 for 5-7 vs 3-7 and 7-7, ** p<0.05 for 5-7 vs 7-7, * p<0.05 for all groups. Scale=0.5 mm.

FIGS. 37(A-I) illustrate a histological assessment of human SMC tubes. Low magnification longitudinal sections of H&E-stained tissue tubes after 7 days in fusion culture (A, D, G). Higher magnification views show one fusion point at the outer surfaces (solid box; B, E, H) and the inner surfaces (dashed box; C, F, I) of the tissue tubes. Lumen on bottom, scale bars=250 μm (low magnification) or 100 μm (high magnification). Images representative from n=3 samples/group.

FIGS. 38(A-E) illustrate spatial position of rings during fusion. Human aortic SMCs were pre-loaded with red or green CellTracker dye prior to ring seeding. Rings with alternating dyes were then stacked and allowed to fuse for 7 days (A). Tubes were then sectioned and stained with Hoechst dye. Red=CellTracker Red (B), green=CellTracker Green (C), and blue=nuclei (D). Merged image shown in (E). Lumen on bottom. Scale=1 mm (A) or 100 μm (B-E). Images representative from n=3 samples.

FIGS. 39(A-D) illustrate PCL cannulation cuff module incorporation for bioreactor culture. Electrospun PCL cuffs were threaded onto silicone tubing and pushed into contact with cell rings at each end of the tube. Tubes were cultured for 4 days (A) to achieve ring fusion, then mounted onto the cannulas in the chamber of a custom luminal flow bioreactor (B). Image of bioreactor with SMC tube is shown in (C), and a schematic of the medium flow loop is shown in (D). Scale=1 cm.

FIGS. 40(A-C) illustrate human SMC tube with spatial heterogeneity. Human aortic SMC rings were either loaded with gelatin microspheres and red CellTracker dye, or without microspheres or dye. Rings with microspheres were placed in the central region of the tube, between outer regions without microspheres. Gross photograph of fused tissue tube shown in (A). PCL cuffs on either end prevent rings from sliding apart after threading onto silicone tubing (prior to fusion), and reinforce the tube ends to aid in handling and cannulation. H&E stain in (B) and (C) shows a section of the vessel wall, where rings appear well-fused, and microspheres maintain their spatial position in the center. Scale in mm (A) or 100 μm (B, C). Images representative of 2 samples.

FIGS. 41(A-G) illustrate fabrication of branched structures. To fabricate branched tubes, the beveled ends of two pieces of 2 mm tubing were placed in a 4 mm base (A). Rings of 2 or 4 mm inner diameters are then threaded over the tubing, where they are allowed to fuse (A). Images of tubes at 0 (B), 3 (C), and 7 (D) days of fusion show near complete fusion by day 3. * in (D) shows a small gap on the underside of the construct. The tube maintained its branched shape after silicone tubing was removed (E-G). Scale=1 mm.

DETAILED DESCRIPTION

Figure 1:
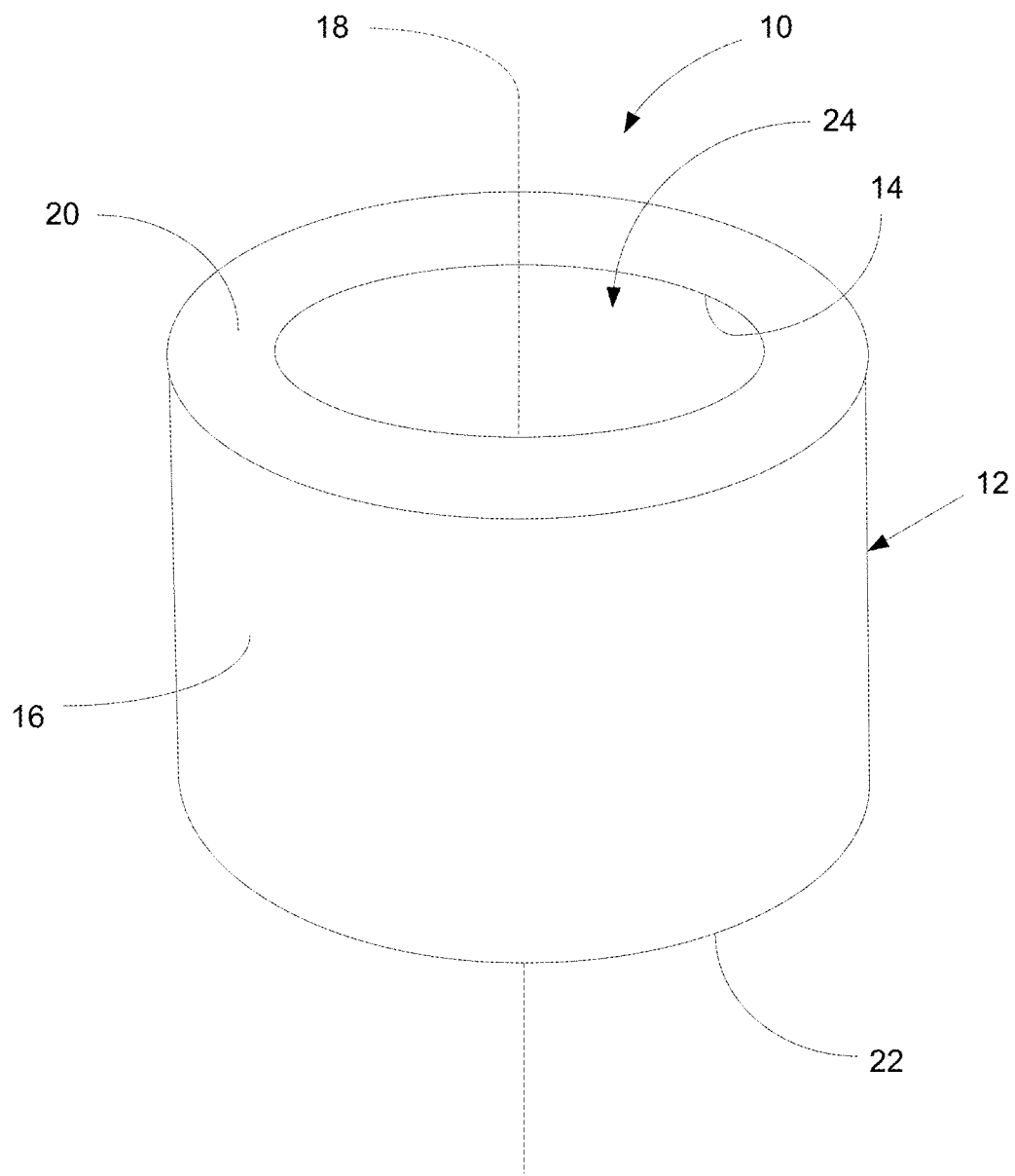
FIG. 1 is a schematic illustration of forming an engineered tissue construct in accordance with an embodiment.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

As used herein, the term "autologous" refers to cells or tissues that are obtained from a donor and then re-implanted into the same donor.

As used herein, the term "allogeneic" refers to cells or tissues that are obtained from a donor of one species and then used in a recipient of the same species.

In the context of the present invention, the term "bioactive agent" can refer to any agent capable of promoting tissue formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

As used herein, the terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

As used herein, the term "carrier material" can refer to a material capable of transporting, releasing, and/or complexing at least one bioactive agent.

As used herein, the term "cartilage" refers to a specialized type of dense connective tissue consisting of cells embedded in a matrix. There are several kinds of cartilage. Translucent cartilage having a homogeneous matrix containing collagenous fibers is found in articular cartilage, in costal cartilages, in the septum of the nose, in larynx and trachea. Articular cartilage is hyaline cartilage covering the articular surfaces of bones. Auricular cartilage is cartilage derived from the auricle of the ear. Costal cartilage connects the true ribs and the sternum. Fibrous cartilage contains collagen fibers. Yellow cartilage is a network of elastic fibers holding cartilage cells, which is primarily found in the epiglottis, the external ear, and the auditory tube. Cartilage is tissue made up of extracellular matrix primarily comprised of the organic compounds collagen, hyaluronic acid (a proteoglycan), and chondrocyte cells, which are responsible for cartilage production. Collagen, hyaluronic acid, and water entrapped within these organic matrix elements yield the unique elastic properties and strength of cartilage.

As used herein, the term "chondrogenic cell" refers to any cell which, when exposed to appropriate stimuli, may differentiate and/or become capable of producing and secreting components characteristic of cartilage tissue.

As used herein, the term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

As used herein, the term "macromer" can refer to any natural polymer or oligomer.

As used herein, the term "polynucleotide" can refer to oligonucleotides, nucleotides, or to a fragment of any of these, to DNA or RNA (e.g., mRNA, rRNA, siRNA, miRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

As used herein, the term "mature chondrocyte" refers to a differentiated cell involved in cartilage formation and repair. Mature chondrocytes can include cells that are capable of expressing biochemical markers characteristic of mature chondrocytes, including, but not limited to, collagen type II, chondroitin sulfate, keratin sulfate, and characteristic morphologic markers including, but not limited to, rounded morphology observed in culture and in vitro generation of tissue or matrices with properties of cartilage.

As used herein, the term "immature chondrocyte" refers to any cell type capable of developing into a mature chondrocyte, such as a differentiated or undifferentiated chondrocyte as well as mesenchymal stem cells that can potentially differentiate into a chondrocyte Immature chondrocytes can include cells that are capable of expressing biochemical and cellular markers characteristic of immature chondrocytes, including, but not limited to, type I collagen, cathepsin B, modifications of the cytoskeleton, and formation of abundant secretory vesicles.

As used herein, the term "tracheal cartilage defect" refers to any tracheal defect of, or injury to, the trachea. Tracheal cartilage defects may be caused by a variety of factors including, but not limited to, stenosis caused by implanted prosthetic devices, penetrating or blunt trauma, and tumors. Additionally, tracheal cartilage defects may be caused by congenital defects ranging from the complete absence of the trachea to an incomplete or malformed trachea.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

As used herein, the term "aggregate" can refer to a group or cluster comprising at least two or more cells (e.g., progenitor and/or differentiated cells).

As used herein, the term "population" can refer to a collection of cells, such as a collection of progenitor and/or differentiated cells.

As used herein, the term "differentiated" as it relates to the cells of the present invention can refer to cells that have developed to a point where they are programmed to develop into a specific type of cell and/or lineage of cells. Similarly, "non-differentiated" or "undifferentiated" as it relates to the cells of the present invention can refer to progenitor cells, i.e., cells having the capacity to develop into various types of cells within a specified lineage or in different lineages.

Embodiments described herein relate to engineered tissue constructs, such as engineered tissue rings, sheets, and disks, systems and methods of forming modular engineered tissue constructs and to the use of modular engineered tissue constructs in modular tissue assembly systems for tissue repair and bio-artificial tissue engineering applications, such as engineered trachea constructs, engineered bone constructs, engineered vascular constructs. The engineered tissue constructs can include self-assembled, scaffold-free, cell aggregates with defined shapes, e.g., rings, disks, or blocks, that are formed by culturing a plurality of cells and nanoparticles and/or microparticles in wells with defined shapes, e.g., rings, disks, or blocks, of a cell culture apparatus or bioreactor. In some embodiments, the self-assembled, cell aggregate can include a population or plurality of cells and plurality of nanoparticles and/or microparticles that are incorporated within the cell aggregate. The nanoparticles and/or microparticles can act as a bulking agent within the cell aggregate to increase the cell aggregate size and/or thickness. Incorporation of the nanoparticles and/or microparticles in the cell aggregate can also improve the mechanical properties of the cell aggregate formed from the cells and nanoparticles and/or microparticles allowing the cell aggregate to be readily manipulated and formed into engineered tissue constructs, such as cartilage rings, bone implants, and/or vascular rings. The nanoparticles and/or microparticles can also include at least one bioactive agent that is differentially and/or controllably released by the nanoparticles and/or microparticles.

The engineered tissue constructs can be used in a modular tissue assembly system to engineer human tissue containing, for example, engineered cartilaginous, bone, and/or vascular segments. The tissue assembly system can permit fusion of self-assembled, scaffold-free, cell aggregates with defined shapes together to generate modular tissue constructs with multiple types of tissues in a spatially-controlled pattern. Culture of the self-assembled, scaffold-free, cell aggregates with defined shapes together in a hollow organ bioreactor can permit further modification of the constructs, including, for example, epithelialization of a surface of the construct.

Advantageously, the tissue assembly system can provide modular control over macroscopic tissue assembly by integration of individual shaped tissue modules of different cell types, permit controlled spatial and temporal presentation of bioactive agents to cells in the constructs, and produce constructs of various sizes and geometries using customizable wells. In one example, engineered trachea constructs can be formed from engineered cartilage rings and perivascular rings and be used to rapidly fill a tracheal defect in vivo. The engineered trachea constructs can avoid tissue granulation, implant migration and restenosis seen in acellular tracheal prostheses, overcome challenges regarding polymer degradation rates and byproducts presented by some scaffold-based approaches, as well as increase cell-cell interactions to help recapitulate de novo tissue formation by eliminating the need for a scaffold. In some embodiments, the engineered trachea constructs can utilize cells that are all of human origin and have the potential for autologous application, circumventing immune issues, potential disease transmission and the need for donor tissue.

FIG. 1 is a schematic illustration of an example of an engineered tissue construct with a defined shape in accordance with an embodiment of the application. The engineered tissue construct 10 has a ring-shape and includes an engineered tissue wall 12 with an inner annular surface 14 and outer annular surface 16 that extend along an axis 18 between a first end 20 and a second end 22 of the tissue wall 12. The outer annular surface 16 defines an outer surface of the engineered tissue ring 10, and the inner annular surface 14 defines an inner lumen 24 of the cartilage ring 10.

The outer annular surface 16 can be substantially parallel to the inner annular surface 14 to provide the tissue wall 12 and engineered tissue ring 10 with a substantially uniform thickness. The thickness of the tissue wall 12 as well as the diameter and length of the tissue ring 10 can be readily tailored and/or engineered for particular bioengineering applications. For example, the diameter of the tissue ring 10 can be at least about 0.1 mm, about 0.5 mm, about 2 mm, about 3 mm, about 4 mm, about 5 mm, about 6 mm, about 7 mm, about 8 mm, about 9 mm, about 10 mm, about 11 mm, about 12 mm about 13 mm, about 14 mm, about 15 mm, about 20 mm, about 30 mm, about 40 mm, about 50 mm, about 75 mm about, about 100 mm or more. The length of the tissue ring can be about 0.1 mm, about 0.5 mm, about 2 mm, about 3 mm, about 4 mm, about 5 mm, about 6 mm, about 7 mm, about 8 mm, about 9 mm, about 10 mm, about 11 mm, about 12 mm about 13 mm, about 14 mm, about 15 mm, about 20 mm, about 30 mm, about 40 mm, about 50 mm, about 75 mm about, about 100 mm or more. The thickness of the tissue ring can be about 0.1 mm, about 0.5 mm, about 2 mm, about 3 mm, about 4 mm, about 5 mm, about 6 mm, about 7 mm, about 8 mm, about 9 mm, about 10 mm, about 11 mm, about 12 mm about 13 mm, about 14 mm, about 15 mm, about 20 mm, or more.

While the outer surface and the inner surface 12 and 14 are depicted as being substantially circular, the outer surface and inner surface 12 and 14 can have other geometries including ellipsoid, toroid, frustoconical, and/or other polygonal geometries. As discussed below, the geometry of the inner surface and the outer surface 12 and 14 of the engineered tissue ring 10 can be defined by the dimensions of the well used to form the engineered tissue ring 10.

It will be appreciated that the engineered tissue construct can have other shapes besides annular or ring shapes. These other shapes can include, for example, disc shapes, wedge shapes, ellipsoid shapes, and other polygonal shapes. The constructs can also include various cavities, holes, and/or lumens. As discussed below, the specific shape of the engineered tissue construct can be defined by the shape of the well used to culture and form the engineered tissue construct.

The engineered tissue ring includes a self-assembled, scaffold-free high density cell aggregate that is formed by culturing a plurality of cells and nanoparticles and/or microparticles in an annular well of a cell culture apparatus or bioreactor. By high density cell aggregates, it is meant the cell aggregate has a cell density of at least about $1\times10^5$ cells/ml in cell growth medium, for example, at least about $1\times10^6$ cells/ml, at least about $1\times10^7$ cells/ml, at least about $1\times10^8$ cells/ml, at least about $1\times10^9$ cell/ml, or at least about $1\times10^{10}$ cell/ml in cell growth medium.

By scaffold-free, it is meant the cells are not seeded in a natural or artificial continuous polymer matrix scaffold that defines the area or volume or at least a portion of the area or volume of the cell aggregate. A scaffold-free cell aggregate as used herein is meant to distinguish the cell aggregate from engineered tissue constructs in which the cells are seeded or embedded into a continuous polymer matrix or scaffold, such as a hydrogel, that encompasses the cells. In contrast, a scaffold-free cell aggregate can include discrete or regions of polymer or matrix materials that are intermixed with the cells and can be in the form of nanoparticles and/or microparticles.

By self-assembled, it is meant that the cells can aggregate or assemble spontaneously or by themselves and without mechanical manipulation while in culture into cell aggregates having defined shapes. Such assembly can be caused by cell-cell interactions, interactions with the particles, or formation of a self-secreted extracellular matrix that can bind to or permit the adhesion of cells in the aggregate.

In some embodiments, the self-assembled, scaffold-free, high density cell aggregate can include a population of cells and a plurality of nanoparticles and/or microparticles that are dispersed with the cells within the cell aggregate. The cell aggregate can also include extracellular matrix material that is secreted by the cells and adheres or binds the cells and nanoparticles and/or microparticles. In some embodiments, the extracellular matrix can include collagen; proteoglycan; glycoprotein; glycosaminoglycan (GAG); as well as other extracellular matrix proteins.

The cells used to form the cell aggregate can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to mixing with the nanoparticles and/or microparticles. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

In some embodiments, the cell can be an undifferentiated or substantially differentiated progenitor cell, such as mesenchymal stem cells, immature chondrocytes, or mature chondrocytes, human umbilical vein, endothelial cells (hUVEC), smooth muscle cells, and mixtures thereof. In other embodiments, the progenitor cell can be an adult stem cell, such as a mesenchymal stem cell. The stem cells can be isolated from animal or human tissues. The stem cell used for the production of the engineered cartilage ring can be autologous or allogeneic. In the embodiments described herein, the stem cell can isolated from, but not limited to, tendon/ligament tissue, bone morrow, adipose tissue or dental pulp. The cell aggregate can include at least about 50%, at least about 60%, at least about 70%, at least about 80% cells based on the total volume of the cell aggregate.

In other embodiments, the cell aggregates can include homogenous or heterogenous populations of the undifferentiated, substantially differentiated, and/or differentiated cells. The cell aggregate can also include defined regions with a first population of cells and other regions with a second population of cells to provide spatial and/or focal region of heterogeneity within the cell aggregate.

The nanoparticles and/or microparticles dispersed with the cells can act as a bulking agent within the cell aggregate to increase the cell aggregate size (e.g., thickness). Incorporation of the nanoparticles and/or microparticles in the cell aggregate can also improve the mechanical properties (e.g., compressive equilibrium modulus and tensile strength) of the cell aggregate and enable more uniform extracellular matrix deposition compared to cell aggregates without the nanoparticles and/or microparticles. This allows the tissue rings formed from the cell aggregate to be readily manipulated and formed into tissue implants, such as trachea implants or vascular implants with defined architectures. The nanoparticles and/or microparticles can also potentially enhance cell function, such as differentiation, and/or enhance or accelerate tissue formation.

The nanoparticles and/or microparticles that are dispersed in the cell aggregate can be formed from a biocompatible and biodegradable material that is capable of improving properties of the cell aggregate and which upon degradation is substantially non-toxic. The microparticles can have a diameter less than 1 mm and typically between about 1 nm and about 200 µm, e.g., about 20 µm to about 100 µm. The nanoparticles and/or microparticles can include nanospheres, nanocapsules, microspheres, and microcapsules, and may have an approximately spherical geometry and be of fairly uniform size. The size and shape of the nanoparticles and/or microparticles dispersed in the cell aggregate can vary to adjust the mechanical properties of the cell aggregate and tissue construct formed from the cell aggregate. In some embodiments, the nanoparticles and/or microparticles dispersed in the cell aggregate can have substantially uniform diameters; while in other embodiments, the diameters of the dispersed nanoparticles and/or microparticles can vary.

The nanoparticles and/or microparticles can include nanospheres and/or microspheres that have a homogeneous composition as well as nanocapsules and/or microcapsules, which include a core composition (e.g., a bioactive agent) distinct from a surrounding shell. For the purposes of the present invention, for the purposes of the present invention, the terms "nanosphere," "nanoparticle," and "nanocapsule" may be used interchangeably, and the terms "microsphere," "microparticle," and "microcapsule" may be used interchangeably.

In some embodiments, the nanoparticles and/or microparticles can be formed from a biocompatible and biodegradable polymer. Examples of biocompatible, biodegradable polymers include natural polymers, such as collagen, fibrin, gelatin, glycosaminoglycans (GAG), poly (hyaluronic acid), poly(sodium alginate), alginate, hyaluronan, and agarose. Other examples of biocompatible, biodegradable polymers are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide) s, biodegradable polyurethanes, and blends and/or copolymers thereof.

Still other examples of materials that may be used to form nanoparticles and/or microparticles can include chitosan, poly(ethylene oxide), poly (lactic acid), poly(acrylic acid), poly(vinyl alcohol), poly(urethane), poly(N-isopropyl acrylamide), poly(vinyl pyrrolidone) (PVP), poly (methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly(glycolide), poly(lactide-co-glycolide), poly(amide), poly(hydroxylacid), poly(sulfone), poly(amine), poly(saccharide), poly(HEMA), poly(anhydride), polyhydroxybutyrate (PHB), copolymers thereof, and blends thereof.

In some embodiments, the biocompatible and biodegradable polymer is a biodegradable hydrogel, such as gelatin. The biodegradable hydrogel can include a plurality of natural macromers that can be cross-linked using a cross-linking agent to provide a plurality of cross-links. Various sugar derivatives, such as glyoxal, D-ribose, or genipin can be used to cross-link the hydrogel. Other cross-linking agents, such as glutaraldehyde, can also be used. Concentrations of the crosslinking agent as well as time and temperature used for crosslinking can be varied to obtain the optimal results The number or percentage of cross-links linking the macromers can be varied to control the mechanical properties, swelling ratios, and degradation profiles of the hydrogel and nanoparticles and/or microparticles. The percentage of cross-links can be varied between about 1% and about 70% by weight, and, for example, between about 20% and about 75% by weight. By increasing the percentage of cross-links, for example, the degradation rate of the biodegradable hydrogel can be decreased. Additionally, the compressive stiffness of the biodegradable hydrogel can be increased by increasing the percentage of cross-links. Further, the swelling behavior of the biodegradable hydrogel can be increased by decreasing the percentage of cross-links. It should also be appreciated that the macromer scaffold can be in either a hydrated or lyophilized state to enhance the addition of bioactive agents.

The nanoparticles and/or microparticles can also be modified to enhance cell function, such as differentiation, and/or enhance or accelerate tissue formation as promote cell adhesion. For example, the nanoparticles and/or microparticles can include at least one attachment molecule to facilitate attachment of at least one cell thereto. The attachment molecule can include a polypeptide or small molecule, for example, and may be chemically immobilized onto nanoparticles and/or microparticles to facilitate cell attachment. Examples of attachment molecules can include fibronectin or a portion thereof, collagen or a portion thereof, polypeptides or proteins containing a peptide attachment sequence (e.g., arginine-glycine-aspartate sequence) (or other attachment sequence), enzymatically degradable peptide linkages, cell adhesion ligands, growth factors, degradable amino acid sequences, and/or protein-sequestering peptide sequences. In one example, an attachment molecule can include a peptide having the amino acid sequence of SEQ ID NO: 1 that is chemically immobilized onto the nanoparticles and/or microparticles to facilitate cell attachment.

The nanoparticles and/or microparticles can also be formed from inorganic materials, such as calcium phosphate materials including mineralite, carbonated nano-apatite, calcium phosphate based mineralite, tri-calcium phosphate, octa-calcium phosphate, calcium deficient apatite, amorphous calcium phosphate, hydroxyapatite, substitute apatite, carbonated apatite-like minerals, highly substituted carbonated apatites or a mixture thereof. Calcium phosphate nanoparticles and/or microparticles can have an average particle size of between about 1 nm and about 200 µm. It will be appreciated that smaller or larger calcium phosphate nanoparticles and/or microparticles may be used. The calcium phosphate nanoparticles and/or microparticles can have a generally spherical morphology and be of a substantially uniform size or, alternatively, may be irregular in morphology. Calcium phosphate nanoparticles and/or microparticles may be complexed with surface modifying agents to provide a threshold surface energy sufficient to bind material (e.g., bioactive agents) to the surface of the microparticle without denaturing the material. Non-limiting examples of surface modifying agents can include basic or modified sugars, such as cellobiose, carbohydrates, carbohydrate derivatives, macromolecules with carbohydrate-like components characterized by an abundance of —OH side groups and polyethylene glycol.

In some embodiments, the nanoparticles and/or microparticles can include at least one, two, three, or more bioactive agent(s) that is capable of modulating a function and/or characteristic of a cell. For example, the bioactive agent may be capable of modulating a function and/or characteristic of a cell that is dispersed with the nanoparticles and/or microparticles. Alternatively or additionally, the bioactive agent may be capable of modulating a function and/or characteristic of an endogenous cell surrounding a tissue construct formed of the cell aggregate implanted in a tissue defect.

In some embodiments, the at least one bioactive agent can include, for example, polynucleotides and/or polypeptides encoding or comprising, for example, transcription factors, differentiation factors, growth factors, and combinations thereof. The at least one bioactive agent can also include any agent capable of promoting cartilage, bone, or tissue formation. Examples of bioactive agents include various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF, HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparin sulfate, polynucleotides, DNA fragments, DNA plasmids, MMPs, TIMPs, interfering RNA molecules, such as siRNAs, miRNAs, DNA encoding for an shRNA of interest, oligonucleotides, proteoglycans, glycoproteins, and glycosaminoglycans.

It will be appreciated at least one or more bioactive agent can be incorporated on or within at least one microparticle. The at least one microparticle can differentially or controllably release the at least one bioactive agent or be taken up (e.g., via endocytosis) by at least one cell to modulate the function and/or characteristic of the cell, such as to promote cartilage formation. The at least one bioactive agent may be at least partially coated on the surface of the at least one microparticle. Alternatively, the at least one bioactive agent may be dispersed, incorporated, and/or impregnated within the microparticle. For example, a bioactive agent comprising a DNA plasmid (e.g., a plasmid encoding BMP-2) can be coated onto the surface of the microparticle. After forming the nanoparticles and/or microparticles with the bioactive agent, the nanoparticles and/or microparticles can be coated with DNA or protein to prevent nanoparticle aggregation and/or promote cellular uptake. It will be appreciated that one or more of the same or different bioactive agents can be incorporated on or within the at least one nanoparticles and/or microparticles.

In some embodiments, a bioactive agent can comprise an interfering RNA or miRNA molecule incorporated on or within at least one microparticle dispersed on or within the cell aggregate. The interfering RNA or miRNA molecule can include any RNA molecule that is capable of silencing an mRNA and thereby reducing or inhibiting expression of a polypeptide encoded by the target mRNA. Alternatively, the interfering RNA molecule can include a DNA molecule encoding for a shRNA of interest. For example, the interfering RNA molecule can comprise a short interfering RNA (siRNA) or microRNA molecule capable of silencing a target mRNA that encodes any one or combination of the polypeptides or proteins described above. The at least one microparticle can differentially or controllably release the at least one interfering RNA molecule or be taken up (e.g., via endocytosis) by at least one cell to modulate a function and/or characteristic of the cell.

The type, distribution, size, and/or crosslinking of the nanoparticles and/or microparticles can also be modified or configured to differentially, controllably, spatially, and/or temporally release at least one bioactive agent in the cell aggregate. In some embodiments, individual nanoparticles and/or microparticles can be formed of different materials or components, such as different polymers having different molecular weights or cross-linking. Moreover, the nanoparticles and/or microparticles can be formed into particular shapes or form to facilitate release of one or more bioactive agents according to a specific temoral release profile. Alternatively, one or more materials or agents can be added to the nanoparticles and/or microparticles to facilitate differential and/or controlled release of one or more bioactive agents according to a temporal release profile. For example, during formation of the nanoparticles and/or microparticles, the concentration of bioactive molecules incorporated into the nanoparticles and/or microparticles can be increased or decreased to increase or decrease the concentration of the bioactive molecules upon release from the nanoparticles and/or microparticles.

In some embodiments, the cell aggregate can include a plurality of first nanoparticles and/or microparticles that can include or release one or more first bioactive agent(s) and a plurality of second nanoparticles and/or microparticles that can include or release one or more second bioactive agent(s). The one or more first bioactive agents and the one or more second bioactive agents may comprise the same or different agents. The one or more first bioactive agents and the one or more second bioactive agents can be differentially, sequentially, and/or controllably released from the first nanoparticles and/or microparticles and second nanoparticles and/or microparticles to modulate a different function and/or characteristic of a cell. It will be appreciated that the one or more first bioactive agents can have a release profile that is the same or different from the release profile of the one or more second bioactive agents from the first nanoparticles and/or microparticles and the second nanoparticles and/or microparticles. Additionally, it will be appreciated that the first nanoparticles and/or microparticles can degrade or diffuse before the degradation or diffusion of the second nanoparticles and/or microparticles or allow for an increased rate of release or diffusion of the one or more first bioactive agents compared to the release of the one or more second bioactive agents. The first and second nanoparticles and/or microparticles may be dispersed uniformly on or within the cell aggregate or, alternatively, dispersed such that different densities of the first nanoparticles and/or microparticles and second nanoparticles and/or microparticles are localized on or within different portions of the cell aggregate. Alternatively, the nanoparticles and/or microparticles can be dispersed at different densities and/or regions of the cell aggregate to provide regions of spatial and/or focal heterogeneity within the cell aggregate.

In some embodiments, the self-assembled, scaffold-free cell aggregate can be formed by combining the nanoparticles and/or microparticles with the cells and then suspending the cells and the nanoparticles and/or microparticles in a culture medium. The nanoparticles and/or microparticles can be formed, for example, from a hydrogel, such as gelatin, that is cross-linked with a cross-linking agent, (e.g., genipin). In some instances, the nanoparticles and/or microparticles can have a diameter of about 20 um to about 100 um and a degree of crosslinking of about 20% to about 70%. The nanoparticles and/or microparticles can also include a growth factor, such as TGFB1, that can be loaded in the nanoparticles and/or microparticles and controllably released from the nanoparticles and/or microparticles. Cell aggregates incorporated with fast degrading nanoparticles and/or microparticles containing TGF-β1 produced significantly more GAG and GAG per DNA.

Figure 2:
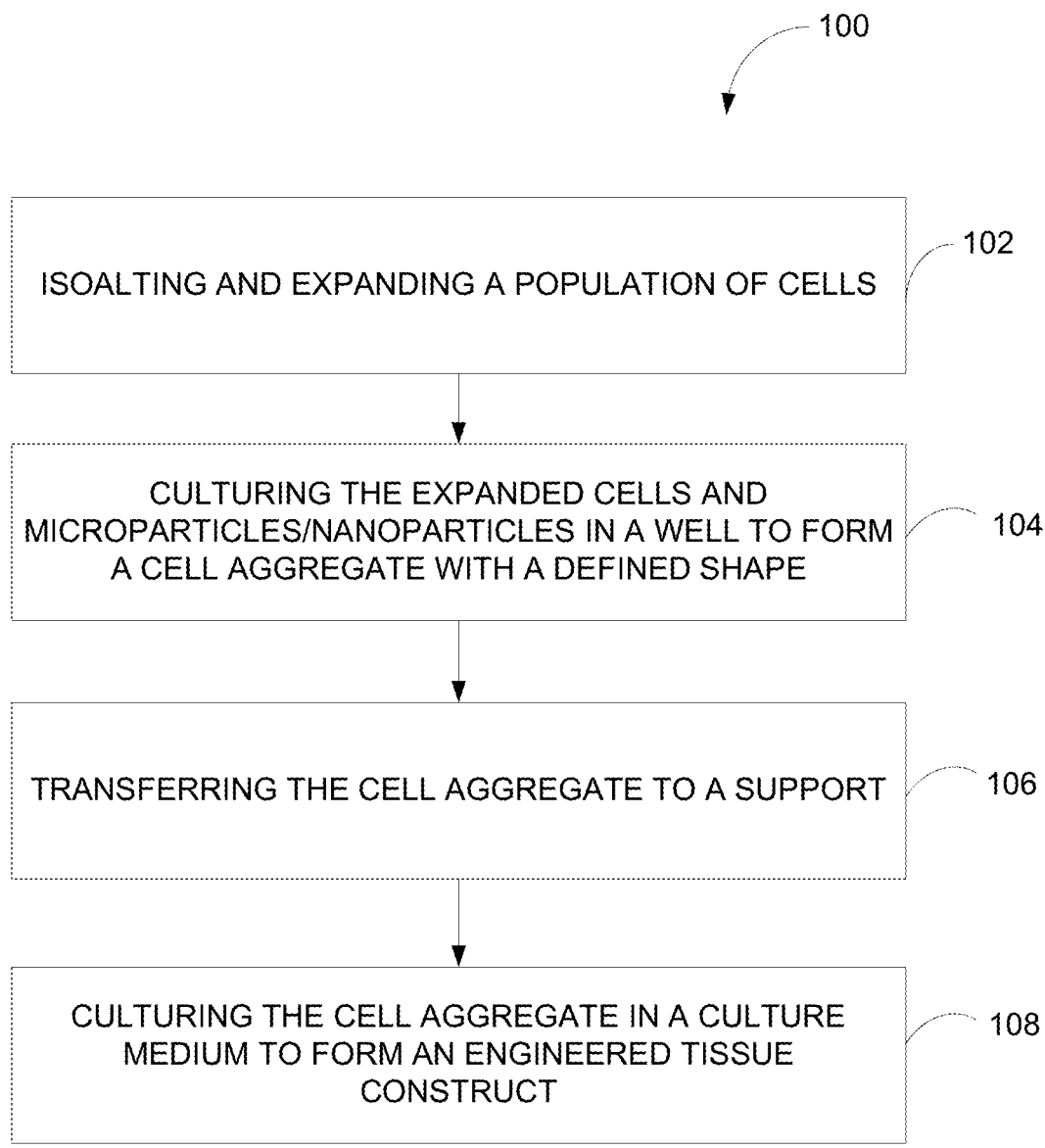
FIG. 2 is a flow diagram showing a method of forming an engineered tissue construct.

FIG. 2 is a schematic illustration of a method 100 of forming an engineered tissue construct that includes at least one self-assembled cell aggregate. In the method, at step 102, a population of cells can be isolated and expanded.

The cells can include any totipotent stem cell, pluripotent stem cell, or multipotent stem cell, and/or differentiated cell. Progenitor cells can include autologous cells; however, it will be appreciated that xenogeneic, allogeneic, or syngeneic cells may also be used. The progenitor cells employed may be primary cells, expanded cells or cell lines, and may be dividing or non-dividing cells. The cells can be derived from any desired source. For example, the cells may be derived from primary tissue explants and preparations thereof, cell lines (including transformed cells) that have been passaged once (P1), twice (P2), or even more times, or host cells (e.g., human hosts). Any known method may be employed to harvest cells for use in the present invention. For example, mesenchymal stem cells, which can differentiate into a variety of mesenchymal or connective tissues (e.g., adipose tissue, osseous tissue, cartilaginous tissue, elastic tissue, and fibrous connective tissues), can be isolated according to the techniques disclosed in U.S. Pat. No. 5,486,359 to Caplan et al. and U.S. Pat. No. 5,226,914 to Caplan et al., the entireties of which are hereby incorporated by reference. In one example, the population of cells can comprise a population of human mesenchymal stem cells.

The cells used to form the cell aggregate can include a mixture of different populations of cells or different phenotypes of cells to modulate the properties of the engineered tissue ring. For example, the cell aggregate that forms the cartilage ring can include mixture of chondrogenic cells, such as mesenchymal stem cells, vascular progenitor cells, such as human umbilical vein endothelial cells, and/or smooth muscle cells.

In one example, the population of cells can comprise a population of chondrogenic cells, such as human mesenchymal stem cells. Chondrogenic cells may be isolated directly from pre-existing cartilage tissue such as hyaline cartilage, elastic cartilage, or fibrocartilage. More specifically, chondrogenic cells may be isolated from articular cartilage (from either weight-bearing or non-weight-bearing joints), costal cartilage, nasal cartilage, auricular cartilage, tracheal cartilage, epiglottic cartilage, thyroid cartilage, arytenoid cartilage, and/or cricoid cartilage. Alternatively, chondrogenic cells may be isolated from bone marrow or an established cell line.

Chondrogenic cells may be allogeneic, autologous, or a combination thereof, and may be obtained from various biological sources. Biological sources may include, for example, both human and non-human organisms. Non-human organisms contemplated by the present invention include primates, livestock animals (e.g., sheep, pigs, cows, horses, donkeys), laboratory test animals (e.g., mice, hamsters, rabbits, rats, guinea pigs), domestic companion animals (e.g., dogs, cats), birds (e.g., chicken, geese, ducks, and other poultry birds, game birds, emus, ostriches), captive wild or tamed animals (e.g., foxes, kangaroos, dingoes), reptiles and fish.

After obtaining a tissue biopsy of auricular cartilage, for example, the chondrogenic cells may be released by contacting the tissue biopsy with at least one agent capable of dissociating the chondrogenic cells. Examples of agents that can be used include trypsin and collagenase enzymes. For example, a tissue biopsy may be sequentially digested in about 0.25% trypsin/EDTA for about 30 minutes, about 0.1% testicular hyaluronidase for about 15 minutes, and about 0.1% collagenase type II for about 24 hours. The digestion may be carried out at about 37° C. in about a 20 ml volume. Any undigested tissue and/or debris can be removed by filtering the cell suspension using a Nitex 70 μm sterile filter followed by centrifugation. The viability of the cells can be assessed by Trypan Blue dye exclusion test. By digesting the tissue biopsy, a population of chondrogenic cells comprising mature chondrocytes, immature chondrocytes, or a combination thereof, may be successfully isolated from the tissue biopsy.

The isolated population of cells may next be expanded in a conditioned growth media effective to promote expansion of the cells. For example, once the chondrogenic cells have been isolated from the tissue biopsy, they may be proliferated ex vivo in monolayer culture using conventional techniques well known in the art. Briefly, the chondrogenic cells may be passaged after the cells have proliferated to such a density that they contact one another on the surface of a cell culture plate. During the passaging step, the cells may be released from the substratum. This may be performed by routinely pouring a solution containing a proteolytic enzyme, such as trypsin, onto the monolayer. The proteolytic enzyme hydrolyzes proteins which anchor the cells on the substratum and, as a result, the cells may be released from the surface of the substratum.

After isolation and expansion of the cells, the cells can be provided in a culture medium and mixed with nanoparticles and/or microparticles. In some embodiments, the culture medium can also include bioactive agents that promote tissue formation. The nanoparticles and/or microparticles may be dispersed with cells in the suspension in a substantially uniform manner. The culture medium can promote self-assembly of cell aggregates comprising the cells and nanoparticles and/or microparticles. In example, the culture medium can include chemically defined basal pellet medium (BPM) and an amount of TGF-β1 effective to stimulate cell growth and aggregation.

At step 104, the suspension can then be provided in a well, vessel, and/or chamber of a culture apparatus with a defined shape, geometry, and/or architecture. The shape of the well can define the shape of the self-assembled cell aggregate and engineered tissue construct. In one example, the well of the culture apparatus can have an annular shape and include an annular post. An outer surface of the annular post can be used to define an inner surface of a tissue ring so formed. The well of the culture apparatus can be formed from a biocompatible material, such as agarose, that promotes self-assembly of the cell aggregates. In one example, the agarose well can be formed by molding agarose with negative molds of machined or 3-D printed polydimethylsiloxane (PDMS).

The density at which the cells are seeded into the wells of the culture vessel can be, for example, about $1 \times 10^5$ cells/mL to about $100 \times 10^6$ cells/mL.

The cells and nanoparticles and/or microparticles can be cultured at a temperature and atmosphere effective to promote formation of a self-assembled cell aggregate that has a shape defined by the well. For example, the cells may be cultured at a temperature of about 37° C. in an atmosphere of about 5% carbon dioxide at an about 90% to about 95% humidity. The oxygen percentage can be varied from about 1% to about 21%. Typically, the cells can be cultured for about 1 day to about 3 or more weeks.

Following self-assembly of the cell aggregate, at step 106, one or more of the self assembled cell aggregates can be transferred from the well onto a support. In one example, where the self-assembled cell aggregate is in the shape of a ring, the ring-shaped self-assembled cell aggregate can be transferred onto a cylindrical support or tube such that the support extends through a lumen of the ring-shaped cell aggregate(s). The support can be made of a biocompatible material, such as silicone and have a diameter and shape substantially the same or similar to the diameter of the lumen of the ring-shaped cell aggregate(s).

At step 108, the cell aggregate(s) positioned on the support can then be provided in a cell differentiation medium, such as a chondrogenic induction medium, in a cell culture vessel and cultured under conditions designed to promote cell differentiation, e.g., cartilage formation. The cells can be cultured at about 37° C. in about a 5% carbon dioxide atmosphere at about 90% to about 95% humidity. The oxygen percentage can be varied from about 1% to about 21%. Cell differentiation medium, can be changed daily or as needed and/or replaced with other cell culture medium, such as osteogenic induction to promote bone formation. Other cell culture mediums can also be used, such as angiogenic medium or vasculogenic medium. The cell aggregate(s) can be cultured for a duration of time effective to promote tissue formation, for example, from about 1 week to about 4 or more weeks.

During culturing, bioactive agent(s), such as TGF-β1 and/or BMP-2, can be released from the nanoparticles and/or microparticles via diffusion and/or as the nanoparticles and/or microparticles begin to degrade. Controlled release of the bioactive agent from the particles may be dependent on the size and composition of the nanoparticles and/or microparticles, as well as the composition of the medium in which the aggregate is immersed. For example, the release rate of the bioactive agent(s) can be selectively controlled by changing the degree or percent of crosslinking of the polymers used to form the nanoparticles and/or microparticles, the size of the nanoparticles and/or microparticles, and the amount of bioactive agent that is loaded into the nanoparticles and/or microparticles.

It will be appreciated that other bioactive agents can also be added to the medium to enhance or stimulate cell growth. Examples of other bioactive agents include growth factors, such as transforming growth factor-β (TGF-β) (e.g., TGF-β1 or TGF-β3), platelet-derived growth factor, insulin-like growth factor, acid fibroblast growth factor, basic fibroblast growth factor, epidermal growth factor, hepatocytic growth factor, keratinocyte growth factor, and bone morphogenic protein. It will also be appreciated that other agents, such as cytokines, hormones (e.g., parathyroid hormone, parathyroid hormone-related protein, hydrocortisone, thyroxine, insulin), fatty acids (e.g., Omega-3 fatty acids such as α18:3 linolenate), and/or vitamins (e.g., vitamin D), may also be added or removed from the serum-free medium to promote cell growth. Additionally, the engineered constructs can be mechanically stimulated to enhance or stimulate cell growth.

The inclusion of the nanoparticles and/or microparticles in the cell aggregate can allow for substantially more uniform spatial delivery of the bioactive agent throughout the interior of the aggregate. The substantially uniform distribution of the nanoparticles and/or microparticles and relatively uniform release of the bioactive agent in the cell aggregate is advantageous for several reasons, including, but not limited to: (1) rapidly inducing uniform cell differentiation; (2) providing control over the spatial and temporal presentation of bioactive agents; (3) allowing for the use of lower concentrations of bioactive agents as compared to systems employing exogenously-supplied growth factors; (4) enhancing the spatial distribution of extracellular matrix that is formed between the cells; and (5) enhancing the amount of extracellular matrix produced in the cell aggregate. These enhanced properties allows and/or provides for the formation of larger, more mechanically robust tissue constructs.

It will be appreciated that the cell aggregate can further include other nanoparticles and/or microparticles, such as second, third, fourth, or more nanoparticles that include other (e.g., second, third, fourth, or more) bioactive agents. The other bioactive agents may be the same or different type of agent (described above). The other nanoparticles and/or microparticles can differentially, sequentially, and/or controllably release the different bioactive agents to modulate the same or different function and/or characteristics of at least one cell in the aggregate. The bioactive agents can have the same or different release profiles from the first nanoparticles and/or microparticles.

As a result of culturing the cell aggregates with the nanoparticles and/or microparticles, a mechanically robust engineered tissue construct with a defined shape can be formed that can be readily shaped, transferred, and/or manipulated to form the tissue construct. In one example, an engineered tissue ring formed from mesenchymal stem cells can have a glycosaminoglycan (GAG) content that can be substantially equal or similar to the GAG content of native cartilage.

In some embodiments, multiple self-assembled cell aggregates can be fused together to form a modular engineered tissue construct. For example, multiple self-assembled cell aggregates having substantially same composition can be positioned or stacked on a support such that portions of the self-assembled cell-aggregates abut one another on the support. The stacked self-assembled cell-aggregates can be cultured in the culture medium and upon culturing can fuse together to form a continuous substantially homogenous modular engineered tissue construct. After culturing, the continuous substantially homogenous modular engineered tissue construct can be removed from the culture vessel.

In one example, as shown in FIG. 4, multiple ring-shaped cell aggregates having similar shapes formed in an annular well can be positioned or stacked on a support such that adjacent ring-shaped cell-aggregates abut one another on the support. The stacked ring-shaped cell-aggregates can be cultured in a chondrogenic medium and upon culturing can fuse together to form a continuous substantially homogenous engineered tissue tube.

In other embodiments, a heterogenous modular engineered tissue construct can be formed that includes defined regions or portions (e.g., rings) of differing or similar cell aggregate materials. The differing regions or portions of the heterogenous modular engineered tissue construct can be provided or formed with or without nanoparticles and/or microparticles and can have similar or different properties to vary the properties of the tissue construct for particular tissue engineering applications.

In some embodiments, a heterogenous modular tissue construct can be formed by fusing self-assembled cell aggregates formed from different mixtures of cells with or without nanoparticles and/or microparticles. For instance, a first mixture of cells with or without nanopaticles and/or microparticles can be seeded into wells of a culture chamber to form first self-assembled cell aggregates. A second mixture of cells with or without nanoparticles and/or microparticles different than the first mixture can be seeded in the same or separate wells of a culture chamber to form second self-assembled cell aggregates. The first mixture of nanopaticles and/or microparticles and cells can include different type, concentration, amount, and/or distribution, of cells, nanoparticles and/or microparticles and/or potentially bioactive agents as the second mixture of nanoparticles and/or microparticles and cells to vary the compositions and properties of the first self-assembled cell aggregates and the second self-assembled cell aggregates.

The first self-assembled cell aggregates and the second self-assembled cell aggregates can be transferred from the wells onto a support such that portions of the self-assembled cell-aggregates abut one another on the support. In some embodiments, one or more first self-assembled cell aggregates can be alternated with one more second self-assembled cell aggregates on the support such that different self-assembled aggregates are in contact with each other. The first and second self-assembled cell aggregate(s) positioned on the support can then be provided in a cell culture medium in a cell culture vessel and cultured under conditions designed to fuse the separate aggregates and form a modular engineered tissue construct.

It will be appreciated that the heterogenous modular engineered tissue construct can be formed by fusing more than two different types of self-assembled cell aggregates. Each of the different self-assembled cell aggregates can include differing mixtures of cells with or without nanopaticles and/or microparticles and be fused together in any combination, e.g., alternating in series, etc. Additionally, each of the different self-assembled cell aggregates can have different shapes so that engineered tissue constructs formed by fusing the different self-assembled cell aggregates can be provided with complex shapes and geometries.

In one example, as shown in FIG. 3, first ring-shaped cell aggregates formed form a mixture of human mesenchymal stem cells and TGF-β1 loaded microparticles and/or nanoparticles and second ring-shaped cell aggregates formed from smooth muscle cells can be stacked on a support to provide alternating rings of the first ring-shaped cells aggregates and the second ring-shaped aggregates. The first and second ring-shaped cell aggregate(s) positioned on the support can then be provided in a cell culture medium in a cell culture vessel and cultured under conditions designed to fuse the rings and form multi-tissue type hMSC and smooth muscle cell tubes with both cartilaginous and non-cartilaginous portions.

In other examples, first ring-shaped cell aggregates formed form a mixture of human mesenchymal stem cells and TGF-β1 and/or BMP-2 loaded microparticles and/or nanoparticles and second ring-shaped cell aggregates formed from a mixture of human mesenchymal stem cells and human umbilical vein endothelial cells (e.g., a 1:1 mixture of MSCs to hUVEC) can be stacked on a support to provide alternating rings of the first ring-shaped cells aggregates and the second ring-shaped aggregates. The first and second ring-shaped cell aggregate(s) positioned on the support can then be provided in a cell culture medium in a cell culture vessel and cultured under conditions designed to fuse the rings and form multi-tissue type hMSC and hUVEC tubes with both cartilaginous and prevascular portions.

Optionally, a homogenous or heterogeneous modular engineered tissue construct formed by the method described herein can be further modified by seeding cells onto or within the homogenous or heterogeneous modular engineered tissue construct. In one example, where the homogenous or heterogeneous modular engineered tissue construct is in the form of a ring or tube used for a trachea implant, respiratory epithelial cells can be seeded on an inner surface of a lumen of the ring or tube to form a bilayer cell tube or ring. It will be appreciated that other cells or cell types can be seeded onto or within the homogenous or heterogeneous modular engineered tissue construct to modulate the properties of the homogenous or heterogeneous modular engineered tissue construct and form a heterogenous or multi-layer structure.

The homogenous or heterogeneous modular engineered tissue construct produced by the method described herein can find use in a variety of applications. One example of such an application can include forming a whole or partial portion of a trachea implant to treat a tracheal defect in a subject. In some embodiments, the tracheal implant can include a heterogeneous cartilage tube with alternating fused cartilaginous and noncartilaginous portions and an inner lumen in which is seeded epithelial cells to provide an epithelial lined implant. Depending upon the clinical needs of the subject, homogenous or heterogeneous cartilage ring or tube produced by the methods described herein may be used to form a whole trachea or only a portion of a whole trachea. For example, a tracheal implant may be formed by first obtaining a homogenous or heterogeneous modular engineered tissue ring or tube that include cartilage rings and/or vascular rings and/or prevascular rings, with or without epithelial cell lining. The tracheal implant may be optimally sized to suit the needs of the subject. The implant may be used to repair a tracheal cartilage defect as described in greater detail below.

Repair of a tracheal cartilage defect may begin by first identifying the defect. Tracheal cartilage defects may be readily identifiable by visually identifying the defects during open surgery of the trachea or, alternatively, by using computer aided tomography, X-ray examination, magnetic resonance imaging, analysis of serum markers, or by any other procedures known in the art.

Once the tracheal cartilage defect has been identified, an appropriately-sized tracheal implant may be selected. For example, the tracheal implant may have a size and shape so that when the tracheal implant is implanted, the edges of the tracheal implant directly contact the edges of native cartilage tissue. The tracheal implant may be fixed in place by, for example, surgically fixing the implant with bioresorbable sutures. Additionally or optionally, the tracheal implant may be fixed in place by applying a bioadhesive to the region interfacing the tracheal implant and the tracheal cartilage defect. Examples of suitable bioadhesives include fibrin-thrombin glues and synthetic bioadhesives similar to those disclosed in U.S. Pat. No. 5,197,973.

The cartilage tissue defect may comprise a stenotic portion of the trachea, such as two of the cartilages comprising the trachea, caused by prolonged placement of a tracheal T-tube. To repair the tracheal cartilage defect, the stenotic portion may first be surgically excised. Next, a tracheal implant may be formed having a size and shape complementary to the size and shape of the excised stenotic portion. The tracheal implant may then be surgically fixed in place of the excised stenotic portion by an end-to-end anastomosis. After the tracheal implant has been suitably fixed in place, the surgical procedure may be completed and the tracheal implant permitted to integrate into the native cartilage tissue.

In an alternative example, the tracheal cartilage defect may comprise a congenital defect, such as a missing trachea, in a pediatric subject. A tracheal implant comprising a whole trachea may be prepared and then surgically implanted into the subject by an end-to-end anastomosis. After the tracheal implant has been suitably fixed in place, the surgical procedure may be completed and the tracheal implant permitted to integrate into the native tissue. By providing the subject with a whole tracheal implant, the tracheal implant may integrate into the native tissue and grow along with the subject, thus removing the need to perform additional surgeries as the subject ages.

It will be appreciated that the homogenous or heterogeneous modular engineered tissue construct produced by the methods described herein can also be used to form tissue constructs other than engineered trachea. Such tissue constructs can include, for example, vasculature implants for vasculature repair, bone implants that potentially include multiple layers or modular structures, tubular tissues or organs, such as the esophagus, small intestines, urethra, vagina, and muscular tubes (e.g., cardiac and skeletal muscle), other organs or tissue, or other implants used to repair tissue or cartilage defects. Tissue defects in the context of the present invention should also be understood to comprise those conditions where surgical repair of tissue is required, such as cosmetic surgery (e.g., nose, ear). Thus, tissue defects can occur anywhere in the body where tissue formation is disrupted, where tissue is damaged or non-existent due to a genetic defect, where tissue is important for the structure or functioning of an organ (e.g., structures such as menisci, the ear, the nose, the larynx, the trachea, the bronchi, structures of the heart valves, part of the costae, synchondroses, enthuses, etc.), and/or where tissue is removed due to cancer, for example. For such applications, the homogenous or heterogenous modular engineered tissue construct can be shaped, molded, or configured into a variety of configurations.

In still other embodiments, the homogenous or heterogeneous modular engineered tissue construct produced by the methods described herein can be combined with or adhered to other tissue constructs to form a heterogeneous tissue constructs. For example, a modular engineered tissue ring or tube produced by the methods described herein can be provided on, combined with or adhered to demineralized bone matrix to provide and osteochondral tissue construct. The tissue construct can be readily implanted and integrated osteochondral defect.

In other embodiments, the DNA or cells in the homogenous or heterogeneous modular engineered tissue construct produced by the methods described herein can be removed or lysed to provide an acellular tissue construct that includes the extracellular matrix so formed and, potentially, the partially or completely degraded nanoparticles and/or microparticles. Removal may be achieved by, for example, detergent treatment, (e.g., SDS treatment) treatment with DNase and RNase, and/or freeze/thaw cycles. The acellular tissue construct can then be used alone for tissue engineering application or in combination with other cell types or growth factors for the promotion of tissue repair. The acellular tissue construct can be used as an acellular biomaterial for tissue engineering application similar to the above after decellularization. When used alone, the acellular tissue can be used to prevent or repair tissue defects, enhance host cell attachment, infiltration, differentiation, extension, and proliferation. The acellular tissue construct as a decellularized product can be used together with other known bioactive agents and cell types for the promotion of tissue repair.

The following examples are for the purpose of illustration only and are not intended to limit the scope of the claims, which are appended hereto.

Example 1

In this Example a tracheal tissue replacement strategy is demonstrated using a bottom-up approach for production of human MSC (hMSC)-derived cartilaginous rings and tubes through employment of custom designed culture wells and an assembly system. This technology is then used to test the hypothesis that incorporation of chondrogenic growth factor-delivering microspheres into the ring and tube-shaped high-cell density constructs enhances chondrogenesis with regard to mechanical properties and matrix production and distribution to provide functional tracheal patency in future clinical applications.

Methods

Experimental Design

The work described here investigated the formation of engineered cartilaginous rings and tubes in custom designed molds. hMSCs alone ("hMSC") or with bioactive factor-releasing biopolymer microspheres ("hMSC+MS") were seeded in annular agarose wells to form scaffold-free self-assembled three-dimensional tissue rings. Subsequently, tissue rings were stacked in 3-ring or 6-ring conformations to fuse into tissue tubes. Chondrogenesis was induced in rings and tubes during 22 days of in vitro culture after which constructs were harvested for analysis. A schematic of the ring and tube formation procedure is shown in FIG. 4.

hMSC Isolation and Culture hMSCs were isolated from bone marrow aspirates obtained from the Case Comprehensive Cancer Center Hematopoietic Biorepository and Cellular Therapy Core under University Hospitals of Cleveland Institutional Review Board approval, as previously described. Briefly, bone marrow aspirates were washed with expansion media (Dulbecco's Modified Eagle's Mediumelow glucose (DMEM-LG; Sigma-Aldrich, St. Louis, Mo.)) containing 10% pre-screened bovine serum (Gibco Qualified FBS; Life Technologies, Carlsbad, Calif.). Mononuclear cells were separated using a Percoll gradient (Sigma-Aldrich), plated in expansion media and cultured in a 37° C. humidified incubator with 5% $CO_2$. Non-adherent cells were washed away during the first media change. Adherent cells received fresh expansion media supplemented with 10 ng/ml fibroblast growth factor-2 (FGF-2, R&D Systems, Minneapolis, Minn.) every 2-3 days. The hMSCs were subcultured at ~90% confluence, and passage 3 cells were used in this study.

Microsphere Synthesis and Characterization

Gelatin microspheres (11.1 w/v % Type A; Sigma-Aldrich) were synthesized in a water-in-oil emulsion, as previously described, with slight modifications. Microspheres were crosslinked with 1 w/v % genipin for 3 h (Wako Chemicals USA Inc., Richmond, Va.), washed with deionized $H_2O$, lyophilized and rehydrated with Dulbecco's Phosphate Buffered Saline (PBS; HyClone Laboratories, Logan, Utah) containing 400 ng TGF-b1 (PeproTech, Rocky Hill, N.J.) per mg microspheres. Light microscopy images of hydrated, crosslinked microspheres (N=268) were acquired on a TMS microscope (Nikon, Tokyo, Japan) with a Coolpix 995 camera (Nikon) to determine microsphere diameters, which weremeasured using NIH Image J analysis software. The degree of microsphere crosslinking was quantified via a ninhydrin assay, based on a previously described protocol. Here, the ninhydrin solution was added to dry microspheres and incubated for 2.5 min.

Cell Culture Well Preparation

Agarose molds for cell culture were prepared as follows. Briefly, a polycarbonate sheet (Small Parts Inc., Miramar, Fla.) was machined to contain annular wells with concentric 2 mm diameter posts surrounded by a 3.75 mm wide trough. A polydimethylsiloxane (PDMS; Sylgard 184, Dow Corning, Midland, Mich.) negative mold of the polycarbonate template was cured and steam autoclaved for sterilization. Two percent w/v agarose (Denville Scientific Inc., Metuchen, N.J.) in DMEM-LG was autoclaved and used to fill the PDMS mold. After cooling, the ring-shaped culture wells were removed from the PDMS mold, moved into 6-well plates (BD, Franklin Lakes, N.J.) and incubated overnight in basal pellet medium (BPM) comprised of Dulbecco's Modified Eagle's Medium, high glucose (DMEM-HG; Sigma Aldrich), 1% ITS p Premix (Corning Inc, Corning, N.Y.), $10^{-7}$ M dexamethasone (MP Biomedicals, Solon, Ohio), 1 mM sodium pyruvate (HyClone Laboratories), 100 µM non-essential amino acids (Lonza Group, Basel, Switzerland), 37.5 µg/ml ascorbic acid-2-phosphate (Wako Chemicals USA Inc.) and 100 µ/ml penicillin-streptomycin (Corning Inc.).

Assembly of Microsphere-Containing Tissue Rings and Tubes

Trypsinized hMSCs (400,000 cells) with or without 0.3 mg TGF-β1 laden microspheres in 50 µL media were seeded in a circular fashion in each custom designed annular well. Microsphere-containing tissues ("hMSC+MS") were seeded and cultured in BPM. hMSC-only groups ("hMSC") did not contain microspheres and were seeded and cultured in BPM supplemented with 10 ng/ml TGF-β1. After 24 h, 3 ml of experimental condition-specific media were added to the agarose wells. On day 2, some of the self-assembled rings were transferred from the annular wells onto 2 mm silicone tubes (Specialty Manufacturing Inc., Saginaw, Mich.) to form 3- and 6-ring tissue tubes. Silicone tubes were sandwiched between custom engineered polycarbonate holders and the developing tissue tubes were cultured horizontally in 60 mm petri dishes (BD) containing 4.8e6 million cells and 9 ml of condition specific media. A schematic of the tissue ring and tube assembly processes is shown in FIG. 5. A Galaxy S4 phone camera (Samsung, Seoul, Korea) was used to capture images of the custom culture set-up right after tissue tube assembly. Tissue rings and tubes with and without microspheres were grown in a humidified cell culture incubator at 37° C. and 5% $CO_2$ for 22 days with media changes every 2 and 3 days, respectively.

Gross Morphological Assessment

On day 22 of total culture, rings (22 days of culture as rings) and tubes (2 days of culture as rings followed by 20 days of culture as tubes) were harvested and photographs of all tissues were taken with a Galaxy S4 phone camera. Healthy, native rat tracheas (male NIH Nude rats 14e15 weeks old (N=4); Taconic, Hudson, N.Y.), freshly harvested from rats sacrificed for another study in accordance to a protocol approved by the Institutional Animal Care and Usage Committee at Case Western Reserve University, were used for comparison.

Biochemical Analysis

Tissue rings (N=4) and 3-ring tubes (N=3) were digested in papain solution (Sigma Aldrich) at 65° C. GAG and DNA contents were measured using dimethylmethylene blue (DMMB; Sigma-Aldrich) and PicoGreen (Invitrogen, Carlsbad, Calif.) assays, respectively.

Histology and Immunohistochemistry

Tissue rings and 3-ring tubes (N=2) were fixed in 10% neutral buffered formalin overnight, embedded in paraffin and sectioned at 5 microns. Rings were sectioned in either axial or vertical planes. Tubes were sectioned first in the axial plane and then reembedded in paraffin and sectioned in the vertical plane. Mounted tissue sections were deparaffinized and rehydrated. Safranin O (Acros Organics) was used to stain for sulfated GAG content with a Fast Green counterstain (Fisher Chemical). For immunohistochemical staining, the presence of type II collagen was detected using anticollagen type II primary antibody (abcam ab34712, Cambridge, UK) with a Fast Green counterstain. A section of the human knee articular cartilage and underlying subchondral bone served as a positive and negative control, respectively. Samples stained with isotype-matched IgG instead of primary antibody also served as negative controls. Histostain-Plus Bulk kit (Invitrogen) with aminoethyl carbazole (AEC; Invitrogen) was used to visualize the primary antibody. Images of stained tissues were acquired using an Olympus BX61VS microscope (Olympus, Center Valley, Pa.) with a Pike F-505 camera (Allied Vision Technologies, Stadtroda, Germany).

Tissue Dimension Measurements and Biomechanical Analysis

Rings

Day 21 tissue engineered rings and rat tracheal sections were sent in chondrogenic media from Case Western Reserve University to Worcester Polytechnic Institute (transit time was 3 nights and 1 night, respectively). Rings were then allowed to equilibrate for approximately 2 h in a 37° C. incubator prior to mechanical testing. Tissue ring wall thickness was measured in PBS using a machine vision system (DVT Model 630; DVT Corporation, Atlanta, Ga.). Measurements were taken in four locations around each ring using edge detection software (Framework 2.4.6; DVT), and the average thickness was used to calculate the average cross-sectional area. Each rat trachea was also measured in four locations, but using calipers due to its more uneven shape. Tissue engineered rings with and without microspheres and rat trachea sections were tested in uniaxial tension (ElectroPuls E1000 with a 50 N load cell; Instron, Norwood, Mass.) using a modified version of a system described previously. Briefly, small stainless steel pins were bent into an "L" shape and served as grips for individual rings (FIG. 11A inset). After applying a 5 mN tare load, engineered rings were pulled in tension to failure at a rate of 10 mm/min. PBS was dripped on tissues during testing to prevent drying. From this test, the maximum load the rings could withstand was calculated. The ultimate tensile stress (UTS) was calculated by dividing the failure load by the cross-sectional area. Each engineered ring was approximated as a torus and each native trachea section was approximated as a hollow cylinder.

Tubes

Tissue engineered 6-ring tubes and 8 mm sections of rat trachea were equilibrated in PBS with 0.1% protease inhibitor (Sigma-Aldrich), and their outer diameters were measured by applying a pre-load of 3 mN with an R Series Controller mechanical testing device (Test Resources Inc., Shakopee, Minn.). Individual tubes and tracheas were tested in luminal collapse as previously described with modifications. Each tube and trachea was compressed by 2 mm (luminal diameter) at a rate of 0.5 mm/min. The load was held for 6 min and then was removed at a rate of 60 mm/min. The load to collapse the lumen by 80% (1.6 mm) was used for comparison between the engineered tubes and rat tracheas. This was done to ensure that only the load required to collapse the lumen without compressing the walls of the tube was analyzed. Tube outside diameter was measured again after a 5 min no-load period. Percent luminal recoil was calculated as the ratio of the final outer diameter/initial outer diameter*100. Video recordings (Galaxy S4 phone camera) were taken of a representative hMSC tube, hMSC p MS tube and a section of rat trachea (after 1 freeze/thaw) compressed by a hand-held pipet to show repetitive luminal collapse and recoil of the tubes.

Statistical Analysis

One-way ANOVA with Tukey's post hoc tests were used to statistically analyze tissue engineered constructs and native tracheas via InStat 3.06 software (GraphPad Software Inc., La Jolla, Calif.). All values are reported as mean±standard deviation. Post tests were performed when p<0.05.

Results

Microsphere Characterization

Gelatin microspheres appeared blue as a result of the crosslinking reaction with genipin. They were 26.6±8.0% crosslinked, and their average diameter was 67.8±55.1 mm (N=268). A representative light microscopy image shows microspheres size variability (FIG. 5). Several hours after seeding, hMSC and hMSC+MS rings had self-assembled around the posts. After 2 days of culture, hMSC microsphere-containing rings appeared thicker and darker due to presence of microspheres compared to hMSC-only tissues, which were opaque off-white (FIGS. 6A and C). The surface of hMSC+MS rings was less smooth compared to that of hMSC-only rings. Both hMSC-only and hMSC+MS rings could be handled with tweezers for tissue tube assembly into 3-ring or 6-ring tubes (FIGS. 6B and D), but microsphere-containing rings held their toroid shape better during transfer from the agarose posts to the silicone tubes.

Gross Morphological Assessment

Tissues harvested after 22 days of total culture were firm and could be easily handled. The thickness of hMSC-only rings was more irregular compared to microsphere-containing rings, which were visually thicker and slightly blue due to residual microspheres that were not fully degraded (FIGS. 7A and D). Stacked rings formed fused 3-ring or 6-ring tissue tubes on the 2 mm silicone tubing (FIG. 7B-F). Rings and 3-ring tissue tubes were pink due to residual media in the tissue, while 6-ring tissue tubes and rat tracheas were rinsed in PBS before being photographed. Similar to the microsphere-containing rings, tubes with microspheres were visually thicker than hMSC-only tubes. hMSC+MS tubes were also longer than the hMSC-only tubes. Incorporation of microspheres contributed to formation of ridged surfaces on tubes compared to smooth surfaces on hMSC-only tubes. Rat tracheas had visibly thinner walls compared to tissue engineered tubes (FIG. 7G).

Biochemical Analysis

Individual rings and 3-ring tubes were analyzed biochemically. As expected, DNA (FIG. 8A), an indirect measure of cell number, and GAG (FIG. 8B) content were significantly greater in tubes compared to individual rings because 3 rings were used for each tube. There was no significant increase in GAG production per DNA (FIG. 8C) in tissues grown in ring compared to tube geometries. Addition of growth factor-delivering microspheres did not significantly affect the cell number at the time of harvest as measured by amount of DNA. However, microspheres significantly increased total GAG and GAG production per cell. GAG/DNA was greater in hMSC+MS tissues than those without MS by factors of 2.2 and 1.7 in rings and tubes, respectively.

Histology and Immunohistochemistry

Safranin O with a Fast Green counterstain was used to visualize the presence and distribution of GAG in tissue engineered rings (FIGS. 9A and C), 3-ring tubes (FIGS. 9B and D) and rat trachea (FIG. 9E). Rings and tubes with microspheres (FIGS. 9C and D) stained more intensely for GAG compared to cell-only constructs (FIGS. 9A and B), corroborating the biochemical analysis. hMSC+MS rings and tubes were also visually thicker and had a more uniform GAG distribution with a smaller fibrous capsule (stained blue/green by Fast Green) on the tissue periphery compared to the hMSC-only tissues. The remaining gelatin microspheres that were not fully degraded by cell-secreted enzymes were visible in the hMSC+MS groups (black arrows in FIGS. 9C and D). Cartilaginous portions of the rat trachea had the most intense GAG staining. Vertical cross sections of tissue engineered tubes of both compositions showed seamless ring fusion. hMSC-only tubes appeared to have lower GAG density in the middle of the constructs. Microsphere-containing tubes maintained ridges from the individual rings that were fused together. Cartilage rings in the rat trachea were separated by noncartilaginous fibrous tissue, which stained blue/green.

The presence and distribution of collagen type II were visualized via immunohistochemical staining (FIG. 10). hMSC and hMSC+MS rings and tubes both showed strong staining for type II collagen, which was more prevalent on the interior of the constructs. However, staining was better distributed in microsphere-containing tissues. Human knee tissue control showed appropriate collagen type II staining of articular cartilage while not staining the subchondral bone.

Tissue Dimension Measurements and Biomechanical Analysis

Rings

The walls of engineered hMSC-only and hMSC+MS cartilaginous rings were significantly thicker than those of native rat tracheas (FIG. 11A). Incorporation of microspheres resulted in rings that were significantly thicker than their cell-only counterparts. Uniaxial tension mechanical testing (FIG. 12A inset) revealed that the maximum force at failure (FIG. 12A) was similar in the engineered rings, but rat tracheal rings required a significantly smaller load to rupture. However, when force at failure was normalized to loaded area (ultimate tensile stress; FIG. 11B), microsphere-containing rings (2.44±0.22 $mm^2$ cross-sectional area) behaved similarly to the rat trachea (1.22±0.16 mmlong; 1.11±0.19 mm2 cross-sectional area), while hMSC-only rings (1.26±0.24 mm2 cross-sectional area) exhibited significantly greater stress at failure than the other two groups.

Tubes

Tissue engineered tubes had a significantly greater outer diameter than the rat tracheas (FIG. 11B). In addition, microspheres containing tubes had a significantly greater outer diameter than hMSC tubes. In a gross biomechanical assessment of the tissue tubes, the qualitative force required to collapse the tubes with a hand-held pipet was the largest for the hMSC+MS tube (FIG. 13). Quantitative mechanical analysis corroborated the qualitative findings. A force was applied to collapse the tubes by 2 mm, the engineered tissues' inner diameter (FIG. 12C inset). The force required to collapse 80% of the lumen of engineered hMSC+MS tubes were about 2.1-2.3 times greater than the force required to collapse hMSC-only tubes and similarly-sized, 8 mm length sections of rat tracheas (FIG. 12C). Cell-only tubes required approximately the same load to achieve luminal collapse compared to the hMSC+MS tubes. After the load was removed, the outer diameters of the tubes were measured again and it was found that all tubes recoiled to nearly 100% of their original diameters (FIG. 12D).

This Example demonstrates the ability to form cartilaginous rings from human bone marrow-derived MSCs in custom culture wells and stack the rings to generate fused tissue tubes. Secondly, this work shows that incorporation of microspheres delivering chondrogenic growth factor (e.g., TGF-β1) into the self-assembled ring- and tube-shaped constructs would enhance neocartilage formation by increasing matrix production, tissue dimensions and mechanical properties. Custom annular culture wells comprised of agarose were used to successfully engineer hMSC-only and microsphere containing rings. On day 2 of culture, rings could be manipulated and stacked onto a silicone tube to fuse into tissue tubes. The two days of culture needed in this study is a much shorter time than the previously reported 3-4 week culture period necessary for high-cell density chondrocyte sheets to achieve mechanical integrity required for manual manipulation. After approximately 3 weeks of culture, tubes were easily removed from the silicone support and exhibited seamless fusion between rings as observed via gross morphological and histological evaluation (FIGS. 7, 9 and 10). The presence of GAG (FIGS. 8 and 9) and collagen II (FIG. 10) indicated cartilaginous tissue formation after 22 days of total culture. These findings confirmed that custom agarose molds can be used to engineer cartilaginous rings and that these rings can be fused into tissue tubes.

While there are reports describing fabrication of rabbit auricular chondrocyte-derived cartilage sheets that were rolled to fuse into a tube in vitro or in vivo, our approach has advantages over these systems. First of all, human bone marrow MSCs used here as the cell source for autologous cartilage tissue formation avoids the need for invasive and potentially detrimental harvest of mature cartilage tissues and provides the capacity for cell expansion to achieve necessary numbers of cells capable of undergoing chondrogenesis. In addition, the use of human cells in our system is potentially a more translatable strategy, as approaches utilizing cells from different species may result in different chondrogenic outcomes compared to those with human cells, delaying or inhibiting transfer of technology to the clinical setting. Secondly, the hMSC-based cartilaginous rings were significantly thicker than previously reported chondrocyte-based approaches. In just 3 weeks of culture, hMSC derived cartilage rings were 0.89 mm (hMSC-only) and 1.25 mm (hMSC+MS) thick compared to rabbit articular chondrocyte-derived cartilage, which was 235 mm thick after 8 weeks of culture, and rabbit auricular chondrocyte-derived cartilage, which was about 500 mm thick after 6 weeks of culture and 553 mm thick after 8 weeks of culture. To achieve wall thicknesses similar to those found in our hMSC-based rings, multiple cartilage sheets would need to be stacked or folded. Thirdly, in terms of cartilage tube fabrication, the ring assembly system does not require the binding of tissue sheets with sutures or ties to form a tubular construct. More importantly, our ring-based approach is a modular system which could prove advantageous when generating multi-tissue type constructs because each ring could serve as a tissue building block. Finally, the ring-to-tube technology may be more favorable in resisting compression in the axial plane, thereby maintaining tracheal patency in future in vivo applications, compared to sheet-to-tube technologies which may have heterogeneous mechanical properties around the circumference of the tube. While rat hepatocyte cell line rings and 2-ring tubes, normal human fibroblast rings and smooth muscle cell rings and tubes have been reported, the fabrication of scaffold-free, stem cell based cartilage-like rings and tubes using a custom ring and tube assembly system has not yet been demonstrated.

The degree of chondrogenesis was also compared between tissues developed from high-density hMSC ring and tube cultures containing proteolytically-degradable TGF-β1-loaded gelatin microspheres and hMSC-only tissues grown in the same geometries with exogenously delivered growth factor. This high-cell density culture system with bioactive microspheres has previously been shown to enhance chondrogenesis, mechanical properties and/or tissue thickness in hMSC-derived aggregate and sheet constructs. In the present work, tissues with bioactive microsphere were visually thicker (both rings and tubes) and longer (tubes) than hMSC-only constructs. Tubes created from microsphere containing rings maintained outer ridge morphology reminiscent of the rings used for fusion (FIGS. 7E, F and 9D). It is possible that even after only 2 days of culture, incorporation of TGF-β1-loaded microspheres encouraged greater and/or more mature matrix deposition in tissue rings, making the remodeling of ECM more challenging during the fusion process. Another possible reason for the presence of ridges in the hMSC+MS tubes is that incorporation of microspheres led to a more uniform cartilaginous matrix distribution and a reduced fibrous capsule, which has been reported to encourage cartilage tissue fusion. This GAG-poor capsule, sometimes seen on the periphery of high-cell density cultures, was more prevalent in hMSC-only tissues and may be the reason for smoother surfaces found in hMSC-only tubes (FIGS. 9A and B) compared to the GAG-rich, ribbed hMSC+MS tubes (FIGS. 9C and D).

Incorporation of growth factor-loaded microspheres enhanced chondrogenesis as detected by biochemical and histological assays and measurement of tissue dimensions. This finding is corroborated by previous reports of improved cartilage formation in high-density hMSC systems with incorporated TGF-b1-loaded gelatin microspheres. Compared to hMSC-only rings and tubes, hMSC+MS rings and tubes produced more GAG per DNA (FIG. 8C) and stained more intensely for GAG (FIG. 9) and collagen type II (FIG. 10), which are all indicative of neocartilage formation. Not only was the ECM more cartilaginous, addition of growth factor loaded microspheres led to increased tissue ring thickness and tube outer diameter (FIG. 11). Taken all together, the biochemical, histological and tissue dimension data supported our hypothesis that incorporation of growth-factor-loaded microspheres into the hMSC high-cell density rings and tubes improved chondrogenesis in the constructs.

Upon mechanical evaluation of tissue engineered rings and tubes, incorporation of microspheres decreased ring tensile strength and did not affect tubular luminal elasticity. Uniaxial UTS values showed that incorporation of microspheres resulted in a lower stress at failure (FIG. 12B). Even though the load at failure was only slightly lower in hMSC+MS rings than hMSC-only rings, the hMSC+MS rings had a significantly greater cross-sectional area (FIG. 11A) resulting in a significantly smaller UTS. Still, reduced UTS values were an unexpected finding since incorporation of growth factor-laden microspheres has been shown to increase the equilibrium compressive moduli of hMSC-derived engineered cartilage sheets. However, the residual gelatin microspheres that were not fully degraded could have been acting as inclusions, thereby weakening the tissues' tensile strength. Another potential explanation for decreased UTS is the differences in biochemical make-up of the ECM in the hMSC+MS compared to hMSC-only rings. The GAG content is a dominant contributor to increased tissue stiffness in compression and collagen content is predominantly responsible for tensile properties in cartilage tissues. While the addition of microspheres significantly increased GAG biochemical content as well as GAG and type II collagen staining, it is possible that microspheres led to a greater relative increase in GAG compared to collagen resulting in lower tensile properties in the hMSC+MS rings than the hMSC-only rings. Mechanical evaluation of tissue tubes showed that all tissue tubes recoiled to almost the original outer diameter, but microsphere-containing tissues required greater force to collapse the tubes. However, microsphere containing tubes were also qualitatively longer than their cell-only counterparts so it is difficult to examine the role that microspheres played on the luminal elasticity mechanics of the tissue tubes.

Tissue generation was influenced by culture in the custom wells and assembly system in the ring and tube geometries. Three-ring tubes had significantly greater DNA and GAG content than individual rings, although these increases were slightly less than the 3-fold proportional increases that would be expected. However, GAG production per cell was not significantly different between ring and tube geometries. Unexpectedly, with and without microspheres, both geometries led to approximately two-fold greater GAG/DNA production compared to high-cell density sheets grown on cell culture inserts using same passage hMSCs from the same donor as used. It is possible that the agarose culture wells limited the diffusion of ECM molecules produced by cells into the bulk medium, thereby increasing their effective concentration in the constructs and the probability of macromolecule assembly and matrix maturation. For example, aggrecan, a cartilage-specific proteoglycan which plays an important role in resisting cartilage compression during loading, is noncovalently bound to hyaluronic acid and stabilized by link protein to form large aggrecan aggregates outside the cell. Collagen fiber bundles are also assembled extracellularly. Additionally, proteoglycane collagen interaction is essential for cartilaginous ECM function. A potentially similar biophysical approach called macromolecular crowding, which incorporates large molecules as a means of increasing medium density and limiting diffusion, has been shown to drastically increase deposition of type I collagen by fibroblasts in tissue culture. Another possibility for improved chondrogenesis is the increased surface area to volume ratio of the toroid compared to sheet culture for the same number of cells, which could result in greater availability of oxygen and nutrients and better removal of waste via diffusion.

The custom well and assembly system in this Example was used to engineer a tracheal replacement which can be initially tested in a small animal model for tracheal defects in a rat. With regard to tissue dimensions, rat tracheas have a similar lumen diameter but the walls of engineered rings were significantly thicker (FIG. 11A) and tubes had significantly greater outer diameters (FIG. 11B) compared to rat tracheas. Mechanical evaluation by uniaxial UTS on the rings and luminal collapse and recoil on the tubes showed that scaffold-free cartilaginous rings and tubes perform at least as well as native rat trachea, suggesting that these engineered tissues may be able to provide the mechanical rigidity necessary to maintain airway patency in the rat. The tissue engineered microsphere-containing neocartilaginous tubes required significantly greater loads to collapse the lumen compared to the similarly-sized rat tracheal segments. While tissue engineered cartilage rings and tubes appeared thicker than rat tracheal cartilage, they are very similar to the thickness of human tracheal cartilage rings. Unlike the tissue engineered torus rings with a circular cross-section presented here, human tracheal cartilage rings are toroid-like with a more rectangular-shaped cross-sectional area which is typically about 1 mm radially and about 4 mm vertically. Control over the vertical dimension of engineered tubes can be achieved by fusing multiple rings together, as shown in this Example. A longer engineered trachea would simply require more cells, microspheres, growth factor and media, but tissue generation should not be inhibited by the length of the construct. Adult human trachea also has a much larger lumen, measuring at least 12 mm in diameter, but using this approach it will be possible to engineer larger diameter rings and tubes by modifying the size of the cell culture annular wells for ring self-assembly and the support strut for tube culture. Additionally, the geometry of the culture-wells and the tissue assembly approach can be easily altered to produce self-assembled tissues of specific shapes (e.g., oval tissues with defined wall thickness, cone like structures, or even figure-eight, honeycomb and dog bone shaped constructs) for applications necessitating geometrical control over anatomical features and/or tissue-level morphology.

A functional tracheal replacement may require much more complexity in tissue organization and function. While the cartilaginous portion of the native trachea provides support to the airway, intervening vascularized fibrous tissue is necessary to supply the cartilaginous rings and mucosal and submucosal layers lining the tracheal lumen with nutrients and oxygen. Our customizable tissue assembly system permits the integration of these vital tissue components to replicate actual tracheal architecture and ultimately function. Firstly, donor-specific needs with regard to tissue anatomy may be addressed by employing annular wells and support struts with custom geometry to engineer the organ. Next, different cell sources and/or differentiation conditions for the tissue units can be used to engineer tissues with requisite properties, such as rings with neovasculogenic capabilities or tubes of tracheal epithelium. Thirdly, incorporation of bioactive microspheres with different compositions into each type of tissue ring may allow for spatial as well as temporal control of cell differentiation and neotissue formation even after multi-tissue fusion. It is also possible that incorporation of growth factor-loaded microspheres can decrease in vitro culture time by releasing bioactive factors after implantation, and in doing so stimulate in vivo tissue maturation and physiological healing. The use of bioactive microspheres in the modular custom culture system described here is a promising approach for tracheal tissue regeneration.

Example 2

This Example shows the generation of osteognic rings and tubes from hMSC that include TGF-β1 and BMP-2 loaded nanoparticles.

hMSC Isolation and Expansion

Human mesenchymal stem cells (hMSCs) were isolated from the posterior iliac crest of 3 healthy male donors (43±5 years) using a protocol approved by the University Hospitals of Cleveland Institutional Review Board and cultured as previously described. Briefly, the aspirates were rinsed with low-glucose Dulbecco's modified Eagle's medium (DMEM-LG; Sigma-Aldrich, St. Louis, Mo.) with 10% prescreened fetal bovine serum (Sigma-Aldrich). Mononucleated cells were isolated using a Percoll (Sigma-Aldrich) density gradient then plated on tissue culture plastic at a density of $1.8 \times 10^5$ cells per $cm^2$ in medium containing 10 ng/ml fibroblast growth factor-2 (FGF-2; R&D Systems, Minneapolis, Minn.) and cultured at 37° C. with 5% $CO_2$. Nonadherent cells were removed after 4 days. The adherent cells, primary hMSCs, were cultured for another 10-14 days with media changes every 3 days. They were then reseeded at $4 \times 10^3$ cells/$cm^2$ and expanded until passage 2, when they were stored in liquid nitrogen in DMEM-LG with 10% dimethyl sulfoxide (DMSO) until use.

Gelatin Microsphere (GM) Synthesis and TGF-β1 Loading

Gelatin microspheres (GM) were synthesized using a water-in-oil single emulsion technique and crosslinked with genipin for 2 hours as previously described. Briefly, 11.1% w/v acidic gelatin (Sigma-Aldrich) was dissolved in deionized water (diH$_2$O), added drop-wise into 250 ml preheated (45° C.) olive oil (GiaRussa, Coitsville, Ohio) and magnetically stirred at 500 RPM. After 10 minutes, stirring ensued at 4° C. for 30 minutes. 100 ml acetone chilled at 4° C. was added to the emulsion and again an hour later. Stirring rate increased to 1000 RPM for 5 minutes after which the solution was filtered and the resulting microspheres were washed with acetone and dried overnight. Microspheres were then crosslinked with 1% w/v genipin (Wako USA, Richmond, Va.) on a magnetic stir plate at RT. After 2 hours, the crosslinked microspheres were rinsed 3 times with diH$_2$O and lyophilized. Characterization of GM can be found in Solorio et al. 2012. Prior to adding the microparticles to the hMSC suspension, empty GM were incubated with PBS for 2 hours at 37° C. For exogenous growth factor supplementation, TGF-β1 (Peprotech, Rocky Hill, N.J.) was added to the medium at 10 ng/ml.

Mineral-Coated Hydroxyapatite Microparticle (MCM) Synthesis and BMP-2 Loading

Hydroxyapatite (HA) microparticles ranging from 3-5 μm in diameter from Plasma Biotal LTD (Derbyshire, UK) were mineral-coated in modified simulated body fluid (mSBF) and loaded with BMP-2. Briefly, HA microparticles were added at 2 mg/ml to mSBF (pH 6.8) containing 141 mM NaCl, 4.0 mM KCl, 0.5 mM MgSO$_4$, 1.0 mM MgCl$_2$, 20.0 mM HEPES, 5.0 mM CaCl$_2$, 2.0 mM KH$_2$PO$_4$ and 4.2 mM NaHCO$_3$ (all from Fisher Scientific) The solution was stirred continuously at 37° C. for 7 days with the mSBF refreshed daily. At the end of the coating process, the MCMs were rinsed with diH$_2$O and lyophilized. Prior to adding the microparticles to the hMSC suspension, empty MCM were incubated with PBS for 4 hours at 37° C. For exogenous growth factor supplementation, BMP-2 was added to the medium at 100 ng/ml.

Cell Culture Well Preparation

Agarose molds for cell culture were prepared as previously described. Briefly, a polycarbonate sheet (Small Parts Inc., Miramar, Fla.) was machined to contain annular wells with concentric 2 mm diameter posts surrounded by a 3.75 mm wide trough. A polydimethylsiloxane (PDMS; Sylgard 184, Dow Corning) negative mold of the polycarbonate template was cured and sterilized. Two percent w/v agarose (Denville Scientific Inc., Metuchen, N.J.) in DMEM-LG (Sigma-Aldrich) was autoclaved and used to fill the PDMS mold. After cooling, the ring-shaped culture wells were removed from the PDMS mold, moved into 6-well plates (BD Falcon), and incubated overnight in a serum-free, chemically-defined basal pellet medium (BPM) containing DMEM-HG (Sigma-Aldrich) with 10% ITS+ Premix (Corning), 1 mM sodium pyruvate (HyClone), 100 μM non-essential amino acids (Lonza), 100 nM dexamethasone (MP Biomedicals, Solon, Ohio), and 0.05 mM L-ascorbic acid-2-phosphate (Wako).

Assembly of Microsphere-Containing Tissue Rings and Tubes

Trypsinized hMSCs (400,000 cells) with or without 0.3 mg GM and 0.08 mg MCM in 50 μL media were seeded in a circular fashion in each custom designed annular well and cultured in BPM+10 ng/ml TGF-β1. After 24 hours, agarose wells were flooded with media. On day 2, the self-assembled rings were transferred from the annular wells onto 2-mm glass tubes (Adams & Chittenden Scientific Glass, Berkeley, Calif.) as individual 2-mm rings, or to form 3×2-mm and 8×2-mm tubes. Glass tubes were placed on top of custom engineered polycarbonate holders and tissue rings/tubes were cultured horizontally in 60 mm petri dishes (BD Falcon) in a humidified cell culture incubator at 37° C. and 5% CO$_2$ for 2 weeks in chondrogenic induction medium (BPM+10 ng/ml TGF-β1) followed by 3 weeks in osteogenic induction medium comprised of DMEM-HG (Sigma-Aldrich) with 10% ITS+Premix (Corning), 1 mM sodium pyruvate (HyClone), 100 μM non-essential amino acids (Lonza), 100 nM dexamethasone (MP Biomedicals, Solon, Ohio), 0.173 mM L-ascorbic acid-2-phosphate (Wako), and 5 mM (3-glycerophosphate (Sigma-Aldrich)+100 ng/ml BMP-2. The induction media were changed every 3 days.

Gross Morphological Assessment

After 5 weeks, rings and tubes were harvested and gross images of all tissues were taken. Thickness and length measurements were performed using micro calipers (Fowler). Four measurements were obtained per specimen at the 12, 3, 6, and 9 o'clock positions.

Statistical Analysis

All data are expressed as mean±SD. The unpaired Student's t test was used to test for significant effects with $p<0.05$ considered significant. Data were analyzed using GraphPad Prism 6.0 software (GraphPad Software Inc., La Jolla, Calif.).

Results

Morphological Assessment

The gross morphology of the rings and tubes was visually assessed after 5 weeks of chondrogenic and osteogenic induction in presence of TGF-β1 (2 weeks) and BMP-2 (3 weeks). Tissue rings and tubes comprised of hMSCs only were noticeably thinner compared to hMSC+GM+MCM specimens. In contrast, the overall length of the hMSC+GM+MCM rings and 3×2-mm tubes appeared reduced, while the 8×2-mm tubes had comparable lengths across groups (FIG. 14).

Quantitative thickness and length analyses of the rings and tubes were in agreement with the qualitative assessment. Rings containing GM+MCM were significantly thicker than hMSC rings alone (FIG. 15A; $p<0.05$). Both tissue tubes (3×2-mm and 8×2-mm) revealed similar trends (FIGS. 15C, E; $p<0.001$). In contrast, measurements of the hMSC+GM+MCM rings showed a significant length reduction (FIG. 15B; $p<0.05$) compared to the hMSC rings alone, which was confirmed by the 3×2-mm tubes (FIG. 15D; $p<0.001$). No differences were observed in the length of 8×2-mm tubes across groups (FIG. 15F).

Example 3

In this Example, we demonstrate that engineered tissues can be formed in clinically relevant specific geometries and sizes that match human tissue dimensions by modulating the thickness and diameter of the engineered cartilage rings and tubes. We use a human bronchial epithelial cell line (hBECs) to engineer an epithelial—cartilaginous bilayer to demonstrate that the engineered cartilage tissue can support an epithelial lining. Epithelialized cartilage bilayers were cultured either submerged in medium or at an air-liquid interface (ALI), which has been shown to be beneficial for respiratory epithelial maturation. Next, vascularization is essential for the success of any tissue engineered construct and is currently a major limitation in the field of tissue engineering. The diffusional limitation of oxygen requires all metabolically active cells within the body to reside within ~150-200 μm of a capillary, thus necessitating the micro-vascularization of thick tissue engineered constructs such as a trachea. Guiding the tissue engineered construct through the initial phases of vasculogenesis might accelerate neovascularization and anastomosis with host vasculature upon implantation. Human umbilical vein endothelial cells (HUVECs) have been co-cultured with various stromal supporting cells for vasculogenic purposes. Here, HUVECs were co-cultured with hMSCs in vasculogenic media to generate prevascular tissue rings, where the cells self-assembled into early microvascular structures. These were then fused with cartilage rings to form prevascular—cartilage composite tissue tubes. Finally, these composite tissues were 1) seeded with human tracheal epithelial cells to engineer a tri-tissue construct with spatial control of tissue composition and phenotype and 2) implanted subcutaneously in mice to demonstrate the ability of the tissues to anastomose with host vasculature.

The system presented herein has the potential to allow for the fabrication of many different complex, vascularized tubular tissues and organs. By adjusting the composition of the individual tissue rings, structures such as blood vessels, gastrointestinal tract, and ureters may be developed. This Example describes the application of this base technology to respiratory airway engineering for functional tracheal replacement. A schematic depicting fabrication of each of these tissues is presented in FIG. 16.

Methods

Experimental Design

Four research objectives were examined in this body of work (FIG. 16). The goal of Part Ia was to tune the thickness of engineered cartilage rings. Part Ib aimed to develop cartilage rings and tubes with custom-defined lumen diameters. In Part II, a respiratory epithelium was engineered on the cartilaginous surface of cartilage tissues. Lastly, Part III focused on developing multi-tissue type tubular constructs comprised of prevascular rings fused with cartilaginous rings, which were ultimately seeded with epithelial cells.

Cell Culture

Bone marrow-derived hMSCs from a single donor were isolated using a Percoll gradient (Sigma-Aldrich, St. Louis, Mo.) and the differential adhesion method, and then expanded in Dulbecco's Modified Eagle's Medium—low glucose (DMEM-LG; Sigma-Aldrich) containing 10% pre-screened fetal bovine serum (Gibco Qualified FBS; Life Technologies, Carlsbad, Calif. or Sigma Premium FBS; Sigma-Aldrich) and 10 ng ml$^{-1}$ fibroblast growth factor-2 (FGF-2, R&D Systems, Minneapolis, Minn.) as previously described. Passage 2-3 hMSCs were used in this study. BEAS-2B human bronchial epithelial cells (hBECs) (ATCC; Manassas, Va.) were cultured in bronchial epithelial cell growth medium (BEGM; Lonza, Walkersville, Md.). Prior to use, culture flasks were coated overnight with 0.01 mg ml$^{-1}$ fibronectin (Sigma-Aldrich), 0.03 mg ml$^{-1}$ type I collagen (Advanced BioMatrix, San Diego, Calif.), and 0.01 mg ml$^{-1}$ bovine serum albumin (Thermo Fisher Scientific, Waltham, Mass.) at 37° C. The next day, flasks were washed with PBS and hBECs were plated at $3.3 \times 10^3$ cells cm$^{-2}$ for expansion. Primary human umbilical vein endothelial cells (HUVECs) (ATCC) were cultured in endothelial growth medium-2 (EGM-2) (Lonza; Basel, Switzerland) and used at passage 3-4. Human tracheal segments obtained at necropsy were stored at 4° C. in 50% Dulbecco's Modified Eagle's Medium—high glucose (DMEM-HG, Hyclone; South Logan, Utah):50% Ham's F-12 (Hyclone) supplemented with 2.5 mM L-glutamine (Sigma-Aldrich), 5 µg ml$^{-1}$ insulin (Sigma-Aldrich), 5 µg ml$^{-1}$ transferrin (Sigma-Aldrich), 5 µM hydrocortisone (Sigma-Aldrich), and 2.5 µg ml$^{-1}$ amphotericin (Sigma-Aldrich). The tracheal segments were trimmed of excess connective and fatty tissue and treated with 0.1% protease XIV (Sigma-Aldrich) at 4° C. for 16 hr. The epithelial cells were isolated by gentle scraping of the luminal surface with a plastic coverslip. Isolated cell clumps were treated 5-7 min with Accutase (Sigma-Aldrich) to dissociate. Cells were washed, resuspended in epithelial proliferation media (75% Ham's F-12:25% DMEM, supplemented with 5% FBS (Sigma-Aldrich), 24 µg ml$^{-1}$ adenine (Sigma-Aldrich), 8.4 ng ml$^{-1}$ cholera toxin (Sigma-Aldrich), 10 ng ml$^{-1}$ epidermal growth factor (Sigma-Aldrich), 0.4 µg ml$^{-1}$ hydrocortisone (Sigma-Aldrich), 10 µM Y-27632 (Selleck Chemicals; Houston, Tex.), and 5 µg ml$^{-1}$ insulin), and seeded onto a lawn of irradiated 3T3 fibroblasts. Media was changed daily and cultures were passaged 2-3 times (1:5) to produce $20$-$50 \times 10^6$ epithelial cells. Epithelial cells were harvested for use by differential trypsination to first remove irradiated 3T3 fibroblasts and then to collect the primary human tracheal epithelial cells.

Microsphere Synthesis and Characterization

Gelatin microspheres (11.1 w/v % Type A; Sigma-Aldrich) were engineered as previously described. In this work, microspheres were crosslinked with 1 w/v % genipin (Wako Chemicals USA Inc., Richmond, Va.) for 2.25-2.5 hours. The percentage of crosslinked amine groups in the polymer was assessed by incubating microspheres for 1.75-2.75 minutes in ninhydrin solution. Experiments in this study used two batches of microspheres which contained similar amounts of crosslinked amine groups in the polymer: 23.6±4.7% and 25.7±2.2%. The diameters of gelatin microspheres used in Parts I and III were 54.4±40.4 µm (N=354) and 43.3±30.0 µm (N=353) in Part II. For growth factor delivery, microspheres were loaded with 400 ng TGF-β1 (PeproTech, Rocky Hill, N.J.) per mg microspheres.

Preparation of Custom Geometry Culture Wells

Annular wells were machined as previously described or 3D printed (Objet 260 Connex, Stratasys) in 3 sizes: 2 mm, 6 mm or 12 mm diameter posts surrounded by a 3.75 mm wide trough. Polydimethylsiloxane (PDMS; Sylgard 184, Dow Corning, Midland, Mich.) was cured in the molds and served as negative molds for casting 2% w/v agarose (Denville Scientific Inc., Metuchen, N.J.) culture wells based on previously described methods. Prior to cell seeding, culture wells that were used to engineer cartilage rings were incubated overnight in chondrogenic basal pellet medium (BPM) comprised of Dulbecco's Modified Eagle's Medium—high glucose (DMEM-HG; Sigma-Aldrich), 1% ITS+Premix (Corning Inc, Corning, N.Y.), 10$^{-7}$ M dexamethasone (MP Biomedicals, Solon, Ohio), 1 mM sodium pyruvate (HyClone Laboratories), 100 µM non-essential amino acids (Lonza Group, Basel, Switzerland), 37.5 µg ml$^{-1}$ ascorbic acid-2-phosphate (Wako Chemicals USA Inc.) and 100 U ml$^{-1}$ penicillin-streptomycin (Corning Inc.). Culture wells that were used to engineer prevascular rings were incubated in endothelial basal medium (EBM; Lonza Group).

Assembly of Cartilage Rings and Tubes (Part I)

In Part Ia, hMSCs ($0.1 \times 10^6$-$0.4 \times 10^6$ cells) with or without 0.75 mg TGF-β1 laden microspheres/$1 \times 10^6$ cells in 50 µL media were seeded and cultured in 2 mm culture wells based on previously described methods. Rings with microspheres ("hMSC+MS") were cultured in BPM and hMSC-only groups ("hMSC"), which did not contain microspheres, were cultured in BPM supplemented with 10 ng ml$^{-1}$ TGF-β1. Tissue rings were grown in a humidified cell culture incubator at 37° C. and 5% CO$_2$ for 21 days with media changes every 2 days.

In Part Ib, $0.5 \times 10^6$ hMSCs, $1.5 \times 10^6$ hMSCs and $3 \times 10^6$ hMSCs with 0.75 mg TGF-β1-loaded microspheres/$1 \times 10^6$ cells were seeded and cultured in 2 mm, 6 mm and 12 mm culture wells in BPM, respectively. On day 2-3, cartilage rings were removed from the annular wells and stacked onto 2 mm, 6 mm or 12 mm outer diameter borosilicate glass tubes (Adams & Chittenden Scientific Glass, Berkeley, Calif.) resulting in 2- and 5-ring tissue tubes in each diameter. Tissue tubes were cultured horizontally on custom engineered polycarbonate holders in deep reservoirs (Axygen Scientific, Union City, Calif.) containing 100 ml BPM. Tissue tubes were grown in a humidified cell culture incubator at 37° C. and 5% $CO_2$ for 21 days with media changes every 3 days.

Assembly of Epithelial-Cartilage Bilayers

Cartilaginous sheets were formed by seeding $0.6 \times 10^6$ cells with 0.75 mg TGF-β1 laden microspheres/$1 \times 10^6$ cells onto cell culture inserts (6.5 mm diameter, 3 μm pore size; Corning). These were grown for 2 weeks with media changes (1 ml, BPM) every 2 days. Epithelial-cartilage bilayers were formed by seeding $8.3 \times 10^4$ hBECs/sheet in 100 μl of BEGM on top of the hMSC+MS sheets at 2 weeks ("EC bilayer sheets"). Cartilage only sheets without an epithelial layer ("C sheets") and epithelial only sheets without a cartilage layer ("Control E sheets") served as controls. Control hBEC sheets were seeded on cell culture inserts (6.5 mm diameter, 0.4 μm pore size; Corning) previously coated overnight with 0.01 mg ml$^{-1}$ fibronectin, 0.03 mg ml$^{-1}$ type I collagen, and 0.01 mg ml$^{-1}$ bovine serum albumin at 37° C. and rinsed with PBS. In all groups, seeded hBECs were allowed to settle and adhere for 3 days, after which the insert medium was removed in some of the groups to expose the constructs to an air-liquid-interface (ALI) for 4 or 7 days ("ALI 4d" and "ALI 7d"). Some of the sheets remained submerged for 7 days ("Submerged 7d"). Starting on Day 3 after hBEC seeding, all tissues were cultured in a 50:50 mixture of BPM and BEGM ("50% BPM 50% BEGM") except cartilage control sheets which continued to be cultured in 100% BPM ("Control C sheets"). In summary, the experimental groups included: (1) Control C sheets (submerged; BPM; 7 d), (2) Control E sheets (ALI; 50% BPM 50% BEGM; 7 d), (3) C sheets (submerged; 50% BPM 50% BEGM; 7 d), (4) C sheets (ALI; 50% BPM 50% BEGM; 4 d and 7 d), (5) EC bilayer sheets (submerged; 50% BPM 50% BEGM; 7 d), and (6) EC bilayer sheets (ALI; 50% BPM 50% BEGM; 4 d and 7 d). Sheets were grown in a humidified cell culture incubator at 37° C. and 5% $CO_2$ with media changes every 2 days.

Assembly of Prevascular-Cartilage Composite Tubes and Tri-tissue Trachea Formation 2 mm cartilage rings were assembled as in Part Ia using $0.4 \times 10^6$ hMSCs and 0.3 mg TGF-β1 laden microspheres. Prevascular rings were made from HUVECs ($0.4 \times 10^6$ cells) and hMSCs ($0.4 \times 10^6$ cells) suspended in 50 μL EGM-2 and seeded in 2 mm ring-shaped culture wells. On day 2, some cartilage and vascular rings were transferred onto 2 mm outer diameter glass tubes suspended in media. All cartilage rings and most prevascular rings that were transferred to glass tubes were used to make tubes on day 2 ("D2") or day 4 ("D4") after ring formation. Prevascular-cartilage tubes were formed by stacking 3 cartilage and 2 prevascular rings in an alternating sequence on day 2 or day 4 to make 5-ring tissue engineered tracheal tubes ("CVCVC D2" and "CVCVC D4") and cultured in a 50:50 mixture of BPM and EGM-2. As controls, at each stacking time point, 3 cartilage rings were stacked without intervening prevascular rings and cultured in BPM ("CCC D2" and "CCC D4") or 50:50 BPM-EGM-2 mixed media ("CCC-MM D2" and "CCC-MM D4"). Some prevascular rings were cultured individually on glass tubes in EGM-2 until the end of the experiment ("V").

Alternatively, some prevascular rings composed of $0.2 \times 10^6$ HUVECs and $0.2 \times 10^6$ hMSCs were maintained in agarose molds for 14 days without being transferred to glass tubes on day 2 ("V—agarose"). In an additional experiment, prevascular-cartilage tubes included 2 cartilage rings and 1 prevascular ring stacked at day 2 ("CVC D2"). These were cultured in a 50:50 mix of BPM and EGM-2 media. All tissue rings and tubes were grown in a humidified cell culture incubator at 37° C. and 5% $CO_2$ for 15 days following ring formation with media changes every 2 days.

For tri-tissue trachea formation, CVC tubes were formed as described earlier for CVCVC tubes, only with two cartilage rings and one vascular ring. These constructs were then placed in closed, perforated 1.5 mL microcentrifuge tubes containing a 0.5 mL suspension of $0.5 \times 10^6$ HTE cells in epithelial proliferation medium and cultured on a rotisserie shaker (Barnstead Thermolyne, Dubuque, Iowa) for 24 hours. Medium was replaced every 6 hours.

Tissue Harvest

Cartilage rings and 2, 6 and 12 mm tubes were harvested 3 weeks after ring formation. Epithelial-cartilage bilayers and their cartilage-only controls were harvested 7 and 10 days after bilayer creation, and epithelial-only controls were harvested after 7 days of culture. Epithelial control sheets (no cartilage) were maintained on the cell culture insert membrane during tissue harvest and sectioning to limit damage to the thin sheets. Prevascular-cartilage tubes and their controls were harvested 15 days post cell seeding in ring molds, and tissue tubes to be seeded with epithelial cells were switched to an epithelial cell suspension for the final 24 hours, 14 days post cell seeding in ring molds. All macroscopic images of tissues were taken with a Galaxy S4 phone camera (Samsung, Seoul, Korea). Tracheas from healthy rabbits (male New Zealand white rabbits, 9 months old (N=6); Covance) and rats (male NIH Nude rats, 14-15 weeks old (N=4); Taconic, Hudson, N.Y.) were used for comparison. Use of harvested tissues from animals sacrificed for unrelated studies was approved by the Institutional Animal Care and Usage Committee (IACUC) at Case Western Reserve University (CWRU).

Biochemical Analysis

Tissue rings (N=3-4 from Part Ia) and tubes (N=4-5 2-ring tissue tubes from Part Ib, N=3-4 tubes from Part III and N=4 rat tracheal segments) were digested in papain solution (Sigma-Aldrich) at 65° C. GAG and DNA contents were measured using dimethylmethylene blue (DMMB; Sigma-Aldrich) and PicoGreen (Invitrogen, Carlsbad, Calif.) assays, respectively.

Histology and Immunohistochemistry

Cartilaginous components of tissues from each Part (N>2) were evaluated for GAG via Safranin O (Acros Organics, Thermo Fisher Scientific) staining with a Fast Green (Fisher Chemical) counterstain and type II collagen deposition (ab34712 at 1:200 dilution; Abcam, Cambridge, UK) with a Fast Green counterstain as previously described. Sections of epithelial-cartilage bilayer sheets and their controls were stained with hematoxylin & eosin (H&E) (N=3). Cytokeratin was detected using an anti-pan-cytokeratin antibody (sc-81714 at 1:100 dilution; Santa Cruz Biotechnology, Santa Cruz, Calif.) with a Fast Green counterstain (N=3). Type I collagen was visualized in prevascular-cartilage tissues using an anti-type I collagen antibody (ab21287 at 1:250 dilution; Abcam) with a Fast Green counterstain (N=2). In vitro—cultured engineered prevascular-cartilage tubes and controls were stained for CD31, an endothelial cell marker, to evaluate prevascular structure formation (N=2). Cryosectioned samples were stained using a ClNtec Histology Staining Kit (Roche, Mannheim, Germany) and anti-human CD31 primary antibody (M0823 at 1:100 dilution; Dako, Carpinteria, Calif.) and counterstained with Mayer's Hematoxylin (Thermo Fisher Scientific). The tri-tissue tube (N=1) was stained with Safranin O for cartilage, pan-cytokeratin antibody for epithelial cells and CD31 antibody for endothelial cells. Stained tissue sections were imaged using an Olympus BX61VS microscope (Olympus, Center Valley, Pa.) with a Pike F-505 camera (Allied Vision Technologies, Stadtroda, Germany).

Cartilage and Epithelial Layer Thickness Analysis in Epithelial-Cartilage Bilayers Cartilage sheets, epithelial sheets and epithelial-cartilage bilayers (N=3/group) stained with H&E were used to assess thickness. For quantification of the thickness of the cartilage portion in each cartilage sheet and epithelial-cartilage bilayer, a 10× magnified image of the center of each construct was acquired. The thickness of the cartilage portion was measured in 3 regions of interest (left, central and right) within this image. For quantification of the thickness of the epithelial portion within each epithelial control sheet and CE bilayer, 3 40× magnified images were acquired. The thickness of the epithelial portion was measured in 3 regions of interest (left, central and right) within each image. The measurements were performed using ImageJ software (NIH, Washington, D.C., USA).

Tissue Dimension Measurements and Biomechanical Analysis

Tissue engineered rings composed of different cell numbers (N=3) and rat tracheas (N=4) were analyzed using uniaxial tension to failure testing and the ring wall thicknesses were measured as previously described. Tissue engineered tubes (N=3) and rabbit tracheas (N=6) (Part Ib and III) were evaluated via luminal collapse and recoil as before with slight modifications. Freshly harvested 5-ring cartilaginous tubes of 2, 6 and 12 mm inner diameters and prevascular-cartilage 2 mm inner diameter tubes and their cartilage-only controls were compressed by their respective luminal size at a rate of 0.5 mm minute$^{-1}$. Rabbit tracheas were evaluated in a similar manner by collapsing the lumen by each respective lumen diameter (5.17±0.35 mm). Maximum load at 80% luminal collapse and the outer diameter after recoil were used for comparison. Engineered (2, 6 and 12 mm diameter) and native tracheal tube wall thicknesses were measured with calipers.

Subcutaneous Implantation of Tracheal Constructs

The surgical procedures used in this study were conducted according to a protocol approved by the IACUC of CWRU which adhered to the NIH Guide for the Care and Use of Laboratory Animals. Nine week-old athymic mice (NCR nu/nu) from the CWRU Athymic Animal Facility were anesthetized using ketamine (160 mg kg$^{-1}$)/xylazine (16 mg kg$^{-1}$), and tracheal constructs were implanted subcutaneously on the dorsa of mice (3 or 4 constructs/mouse). The incisions were closed and the mice were administered 0.1 mg kg$^{-1}$ buprenorphine at 0 and 12 hours post-surgery.

Three different constructs were implanted: 1) tubes consisting of 3 cartilage rings prepared as above and cultured in BPM (CCC), 2) tubes consisting of 3 cartilage rings alternating with 2 prevascular rings prepared as above but with only hMSCs in the prevascular rings (without HUVECs) and cultured in 50:50 BPM:EGM-2: (CVCVC-noH), and 3) tubes consisting of 3 cartilage rings separated by 2 prevascular rings prepared as above and cultured in 50:50 BPM: EGM-2 (CVCVC). All tubes were made by stacking rings at day 4 and culturing for a further 15 days prior to implantation. Tubes were collected on the day of implantation (N=1/group) and harvested on days 15 (N=2 for CCC and N=3 for CVCVC-noH and CVCVC/group) and 42 (N=1/group) post-implantation. Prior to the 42 day harvest FITC-UEA-1 (Vector Labs, 100 µg in 100 µL of PBS) was perfused via tail vein injection to label human endothelial cells that were incorporated into perfused vasculature. Half of each tube was processed via paraffin sections which were stained with H&E, Safranin 0, and alizarin red S (Sigma Aldrich). The other half of each tube was cryosectioned and sections were stained with DAPI (Thermo Fisher Scientific) to evaluate for fluorescent lectin staining. Bright-field images were acquired as described earlier. Fluorescent images were taken on an Eclipse TE300 (Nikon, Tokyo, Japan) equipped with a Retiga-SRV digital camera (Qimaging, Burnaby, BC, Canada).

Statistical Analysis

Statistical analysis of tissue engineered constructs and rat and rabbit tracheas was conducted using 1-way ANOVA with Tukey's post hoc tests performed when $p<0.05$ (InStat 3.06 software; GraphPad Software Inc., La Jolla, Calif.). Means of all values are reported with errors signifying standard deviation.

Results Cartilage Rings with Defined Wall Thickness
Macroscopic and Histological Assessment With the goal of controlling the thickness of cartilage rings, the number of hMSCs used to form the rings was varied from 0.1 to 0.4 million cells per ring, and TGF-β1 was presented either in the media or from incorporated microspheres (MS). Rings assembled from a greater number of hMSCs had a higher frequency of ring formation, were grossly (FIG. 17A) and quantitatively thicker (FIG. 17B) and were heavier (FIG. 17C). Ring thickness could be modulated by 25-35% by increasing cell number. Samples that did not form rings resulted in C-shaped constructs or 1-3 individual aggregates. Microsphere-containing rings were significantly thicker than hMSC-only constructs and all engineered rings were thicker than cartilage ring segments from rat tracheas. Glycosaminoglycan (GAG; a prevalent polysaccharide in hyaline cartilage) staining was strong in all engineered tissues and appeared similar to staining in rat tracheal sections (FIG. 17A). Type II collagen, the main collagenous component of hyaline cartilage ECM, was also apparent in both types of engineered cartilage (FIG. 17A). Compared to hMSC-only constructs, hMSC+MS rings appeared to have less of a fibrous capsule on the outer edge of the tissue.

Biochemical Analysis

By measuring the amount of GAG and DNA in the variable thickness cartilage rings, quantitative differences in tissue composition as a function of the number of cells used during fabrication were elucidated (FIGS. 17C-H). Rings composed of more cells contained more GAG (FIG. 17D) and DNA (FIG. 17E). Chondrogenesis was not affected by cell number as the GAG/DNA (FIG. 17F) and GAG/wet weight (FIG. 17G) values were the same in rings made with varying cell numbers. As expected, hMSC+MS rings weighed more (FIG. 17C) and contained significantly more GAG (FIG. 17D, except 0.1 million cells/ring) and GAG/DNA (FIG. 17G) than hMSC-only rings. Compared to rat tracheal segments, engineered tissues had significantly more GAG/DNA (FIG. 17F), more GAG/wet weight (FIG. 17G), and less DNA/wet weight (FIG. 17H). This was anticipated because the tracheal segments are composed of other tissues in addition to cartilage.

Mechanical Analysis

All engineered rings required a significantly greater load to rupture under uniaxial tension compared to rat tracheal rings (1.21±0.16 mm vertically) (FIG. 17I), demonstrating biomechanical functionality and potential ability to maintain tracheal luminal patency. In addition, the ultimate tensile stress (UTS, failure load normalized by loaded area) was at least as high as that of the rat trachea in all groups (FIG. 17J) signifying that the engineered cartilage tissue is at least as strong as the native rat tracheal tissue. Similar failure loads and UTS values across the different thickness rings (except the UTS of 0.2 million cells/ring without microspheres) indicate that geometry does not affect the mechanical properties of the engineered cartilage for the range of wall thickness examined.

Cartilage Tubes with Defined Lumen Diameters

Macroscopic and Histological Assessment

To demonstrate the scalability of this system, cartilaginous rings comprised of hMSCs and TGF-β1-microspheres were fabricated with 3 different inner diameters and then fused into cartilage tubes with defined lumen dimensions. Rings assembled in larger diameter wells had a lower frequency of ring formation even though the cell and microsphere numbers were linearly scaled with the diameter of the wells (FIG. 18A). Cartilage rings of each diameter successfully fused into firm cartilage tubes. The lumen of the tubes was smooth while the outer wall was ribbed. Rabbit tracheal sections resembled the dimensions and gross morphology of 6 mm engineered cartilage tubes. The wall thickness of the 2 mm, 6 mm and 12 mm diameter engineered cartilage tubes was not affected by the lumen size (FIG. 18B). Additionally, 6 mm cartilage tube walls were only 16% thicker than rabbit tracheal walls, which had similar lumen diameters. GAG staining was strong in all engineered tubes but appeared weaker than staining in rabbit tracheal sections (FIG. 18A). Type II collagen stained uniformly with strong intensity in the engineered cartilage tubes (FIG. 18A).

Biochemical Analysis

Biochemical evaluation of cartilage tubes (FIGS. 18C-H) revealed that larger diameter tubes were heavier (FIG. 18C) and contained more GAG (FIG. 18D) and DNA (FIG. 18E). Interestingly, tubes with larger lumen diameter (6 and 12 mm) had decreased GAG/DNA (FIG. 18F) and GAG/wet weight (FIG. 18G) compared to 2 mm lumen diameter tubes while maintaining similar amounts of DNA normalized to wet weight (FIG. 18H) indicating somewhat decreased chondrogenesis in the larger tubes.

Mechanical Analysis

To evaluate the biomechanical properties of engineered cartilage tubes and compare their behavior to native rabbit tracheas, the lumen of each tube or trachea was compressed by applying a perpendicular load. All engineered tubes required a significantly smaller load to collapse 80% of the lumen diameter compared to rabbit tracheal segments of similar length (FIG. 18I). The load at 80% collapse was significantly larger for 2 mm diameter tubes compared to 6 and 12 mm tubes. Subsequently, the compressive load was removed and the outer diameter of each tube before and after collapse was compared to calculate the recoil of engineered tubes and rabbit tracheas. All luminally collapsed tubes recoiled to nearly 100% of the original outer diameter with no significant differences between the groups (FIG. 18J).

Epithelialized Cartilage Bilayers

Histological Assessment and Immunohistochemistry

As a proof-of-principle of establishing an epithelial lining on the tissue engineered tracheas, epithelized cartilage (EC) bilayers were engineered by seeding hBECs on the surface of 2-week-old microsphere-containing hMSC sheets. Bilayer tissues cultured at ALI, which is typically employed for respiratory epithelial culture, were compared to bilayers cultured submerged in media for 4 d and 7 d. Hematoxylin and eosin (H&E) staining showed uniformly distributed chondrocytes within a homogenous ECM that stained positive for GAG in the microsphere-containing hMSC layer of all single and bilayer tissues (FIG. 19A). However, GAG staining appeared less intense in the cartilage layer of the EC bilayer sheets compared to cartilage only sheets (C sheets) alone in 50:50 basal pellet medium (BPM):bronchial epithelial growth medium (BEGM) and C control sheets in 100% BPM. Additionally, the cartilage layer of the epithelial-cartilage bilayers cultured at ALI showed a time-dependent decrease in GAG staining from 4 d to 7 d (FIG. 19A).

Immunostaining for type II collagen was strong in all cartilage layers further confirming cartilaginous ECM synthesis (FIG. 19B). Unlike GAG deposition, however, there were differences in the distribution of type II collagen between the experimental groups and the control C sheets in BPM. Control C sheets in BPM had more uniform type II collagen deposition throughout their thickness compared to C sheets in 50:50 BPM:BEGM and EC bilayer sheets, which had decreased type II collagen on the upper surface of the hMSC layers. Cartilage layers were negative for epithelium-specific cytokeratin across groups. In contrast, localized cytokeratin staining was observed in all epithelial layers of EC bilayer sheets comparable to control E sheets.

Thickness Quantification of Cartilage and Epithelial Components

To evaluate the quality of the epithelial and cartilage layers by another metric, the thickness of each tissue portion was quantified as a measure of spatial control over cell phenotype and tissue development. The cartilage layers of all C sheets and EC bilayer sheets cultured in the 50:50 mixture of BPM and BEGM were thinner compared to controls submerged in normal BPM, but differences were significant only for the C sheets ALI 4 d, EC bilayer ALI 7 d, and submerged 7 d groups (FIG. 19C). Neither the ALI culture conditions nor duration significantly affected the thicknesses of hMSC layers in C sheets cultured in mixed media (FIG. 19C). The cartilage layer of the EC bilayers showed a slight but not significant time-dependent decrease in thickness from 4 d to 7 d at ALI (FIG. 19C). Moreover, all epithelial layers of EC bilayer sheets were significantly thinner compared to control E sheets cultured on cell culture inserts at ALI for 7 d (FIG. 19D). Epithelial layers at ALI showed a significant time-dependent increase in thickness from 4 d to 7 d (FIG. 19D). Compared to ALI 7 d, E sheets submerged for 7 d were significantly thinner (FIG. 19D).

Prevascular—Cartilage Composite Tubes and Tri-tissue Tracheas

Macroscopic and Histological Assessment

While localized tissue differentiation and maturation are critical for the complex spatial organization of a trachea, coherent tissue fusion between the incorporated tissue types is also important for organ functionality. Timing may play a critical role in the success of tissue fusion as well as development of tissue-specific phenotypes. As a result, cartilage and prevascular rings were cultured individually for varying time periods prior to stacking them for fusion into a composite tube to determine the impact of timing of fusion on resultant tissue structure and differentiation. With the goal to establish custom-patterned, localized cartilage and prevascular soft tissue segments within the engineered tracheas, 2 prevascular rings (V) comprised of hMSCs and HUVECs were fused with 3 cartilaginous microsphere-containing hMSC rings (C) in an alternating fashion to create prevascular soft tissue-cartilage composite tubes (CVCVC). Control cartilage-only tubes were composed of 3 cartilage rings (CCC).

Figure 20:
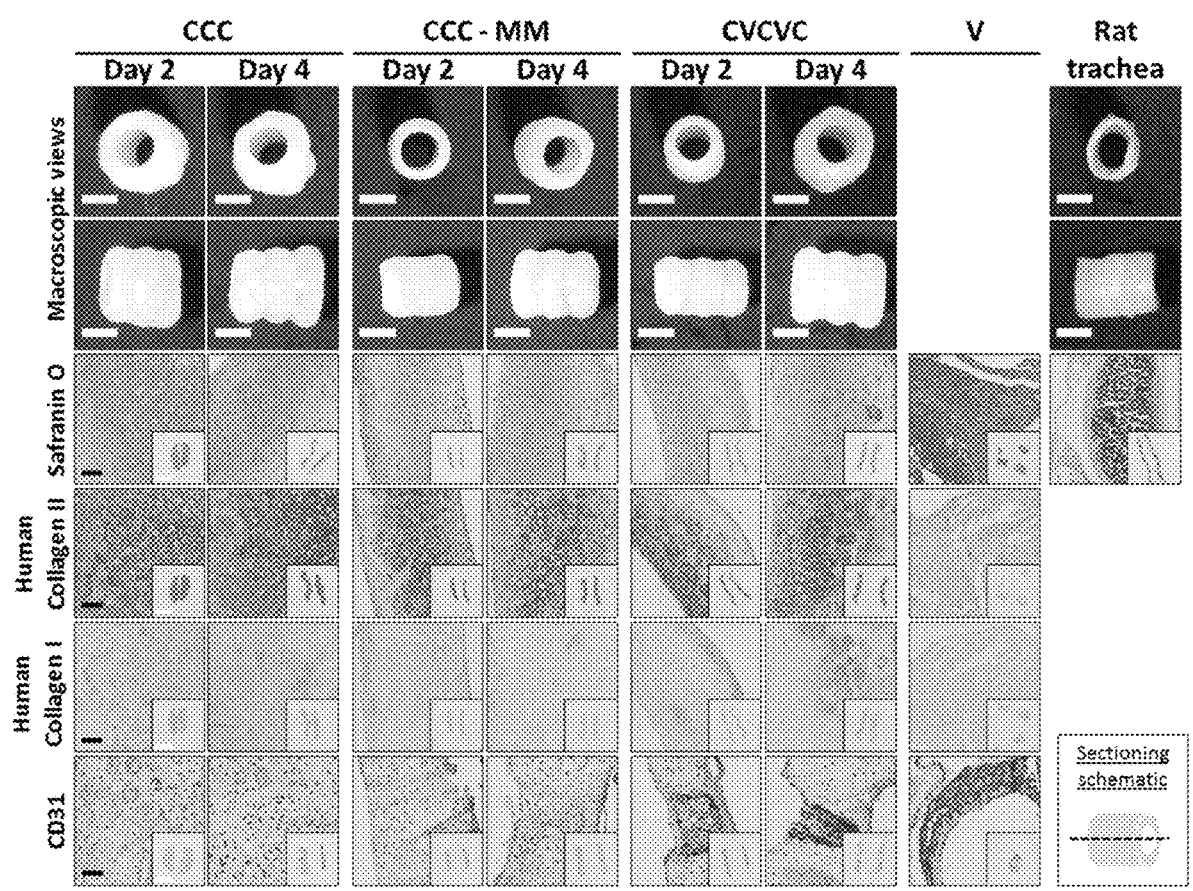
FIG. 20 illustrates macroscopic images and photomicrographs of Safranin O staining for GAG, and human type II collagen, human type I collagen and CD31 immunohistochemistry of prevascular-cartilage tissue engineered tubes and controls. Images and longitudinal sections of cartilage tubes in chondrogenic media (CCC), cartilage tubes in mixed chondrogenic and endothelial media (CCC-MM) and prevascular-cartilage tubes in mixed media (CVCVC) stacked on day 2 and day 4 after ring formation, and axial sections of prevascular rings (V) in endothelial media are depicted. Black scale bars are 200 µm; white scale bars are 2 mm. Images without scale bars in a single row are the same magnification.

Individual rings cultured for 2 or 4 d in their respective media were successfully fused into continuous tissue tubes. Tubes were harvested 2 weeks after cell seeding (FIG. 20). Rings that were cultured individually for 6 d or longer did not fuse into tissue tubes.

All cartilage containing tubes had a pearly white surface and maintained an open lumen upon harvest. In the control cartilage-only tubes that were cultured in mixed media (CCC-MM; 50:50 BPM:endothelial growth medium-2 (EGM-2)) and the CVCVC groups but not in the cartilage-only tubes cultured in 100% BPM (CCC), rings fused at day 4 resulted in qualitatively thicker-walled constructs compared to rings fused at day 2. The walls of all constructs were grossly thicker than walls of rat tracheas. Cartilaginous components of all the tubes stained positively for GAG and type II collagen content with minimal type I collagen staining. Rat tracheal cartilage exhibited the strongest Safranin O staining. Remaining gelatin microspheres stained with anti-type I collagen antibody, as expected. GAG and type II collagen staining in cartilage-only tubes grown in BPM was the best distributed from the lumens to the outer tube edges whereas CCC-MM and CVCVC tubes had non-cartilaginous fibrous capsules on the outer surfaces.

CD31 staining (FIG. 20) showed that endothelial cells remained localized to the prevascular ring portions and some regions exhibited endothelial cell organization into prevascular structures. However, these structures were not as extensive as those in prevascular rings (V) grown for the duration of the experiment on glass tubes in EGM-2, in which more of the endothelial cells were incorporated into prevascular structures. The majority of endothelial cells in prevascular rings grown in EGM-2 were incorporated into complex prevascular plexuses. All cartilage only tubes, whether grown in BPM or mixed media, were negative for CD31 expression. Interestingly, more advanced plexus formation in the prevascular ring portion was noted in prevascular-cartilage composite tubes in another experiment. Additionally, prevascular rings cultured in agarose wells for the duration of the experiment showed even more robust prevascular plexus formation compared to prevascular rings cultured on glass tubes (FIG. 20).

Biochemical Analysis

Figure 21:
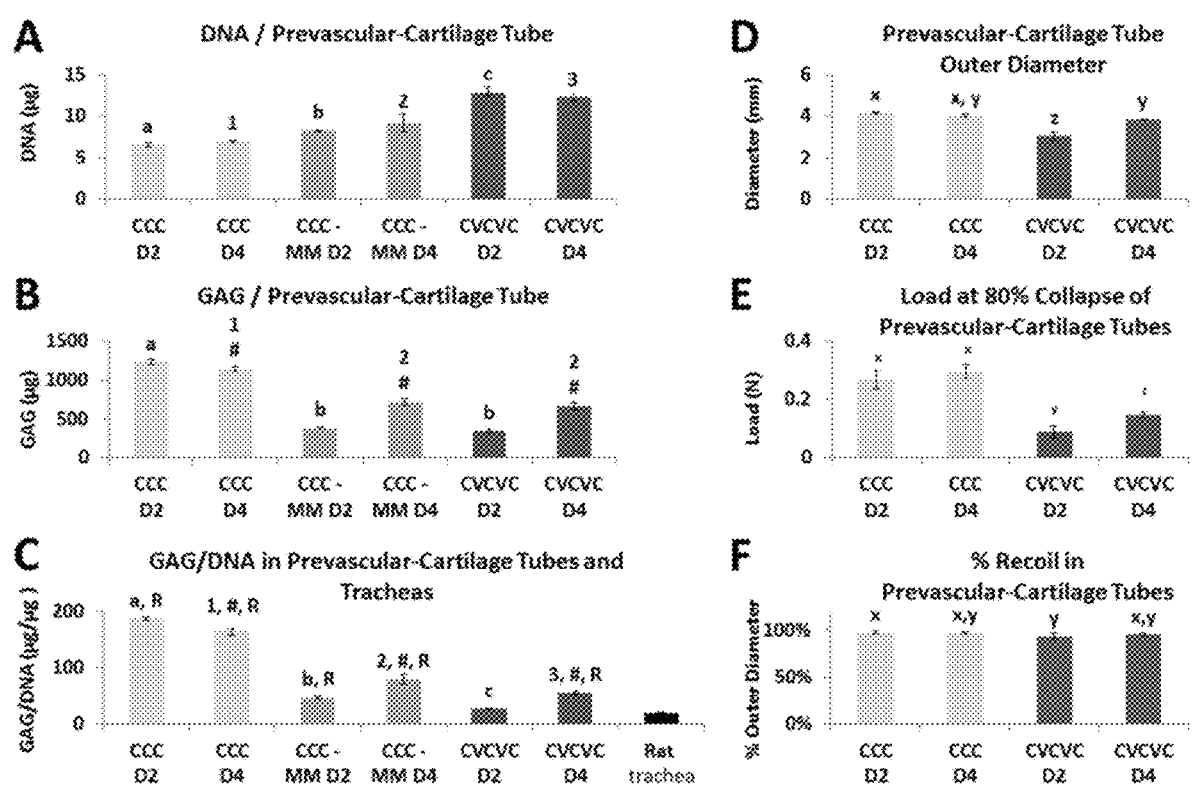
FIGS. 21(A-F) illustrate biochemical and mechanical analysis of prevascular-cartilage tubes and controls. (A) DNA, (B) GAG and (C) GAG normalized to DNA were acquired from tissue engineered cartilage only tubes in chondrogenic media (CCC, light gray, N=3-4), cartilage tubes in mixed endothelial and chondrogenic media (CCC-MM, medium gray, N=4) and prevascular-cartilage tubes in mixed media (CVCVC, dark gray, N=4). (C) Rat tracheal GAG/DNA was used for comparison (black, N=4). (D) Tube outer diameter, (E) load required to collapse 80% of lumen diameter and (F) tube recoil after luminal compression were measured in engineered tubes (N=3). D2: Rings fused after 2 days of individual culture, D4: Rings fused after 4 days of individual culture. (A-C) a,b,c: Day 2 groups without common letter differ ($p<0.05$); 1, 2, 3: Day 4 groups without common number differ ($p<0.05$); #: significantly different than Day 2 group ($p<0.05$); R: significantly different than rat trachea. (D-F) x,y,z: groups without common letter differ ($p<0.05$). Data shown as mean±SD.

The quality of the cartilage tissue in the composite tubes was also analyzed biochemically. CVCVC constructs, which were comprised of more cells, had significantly more DNA than cartilage-only constructs (FIG. 21A). Surprisingly, CCC-MM groups also had significantly more DNA than CCC tubes despite having the same number of incorporated cells. The GAG and GAG/DNA contents (FIG. 21B, C) of constructs grown in BPM:EGM-2 mixed media (CCC-MM and CVCVC) was significantly less than those of CCC tubes grown in BPM, which corroborates histological findings (FIG. 20). Additionally, cartilage-only and CVCVC day 4 constructs in mixed media had significantly more GAG and GAG/DNA compared to day 2 constructs cultured in the same media. All engineered tubes except for CVCVC day 2 had significantly more GAG/DNA than native rat tracheas (FIG. 21C).

Mechanical Analysis

CCC and CVCVC tubes were mechanically characterized for luminal rigidity (FIGS. 21D-F). CVCVC day 2 tubes had the smallest outer diameter out of all the tubes analyzed (FIG. 21D). CCC day 2, CCC day 4 and CVCVC day 4 tubes had outer diameters of approximately 4 mm. When evaluated in luminal collapse, the CVCVC tubes bore significantly less load at 80% luminal collapse compared to CCC tubes (FIG. 21E). Additionally, CVCVC day 4 tubes bore significantly more load at 80% luminal collapse than CVCVC day 2 tubes. All engineered tubes recoiled to nearly 100% of the original diameter (FIG. 21F).

Tri-tissue trachea formation

Figure 22:
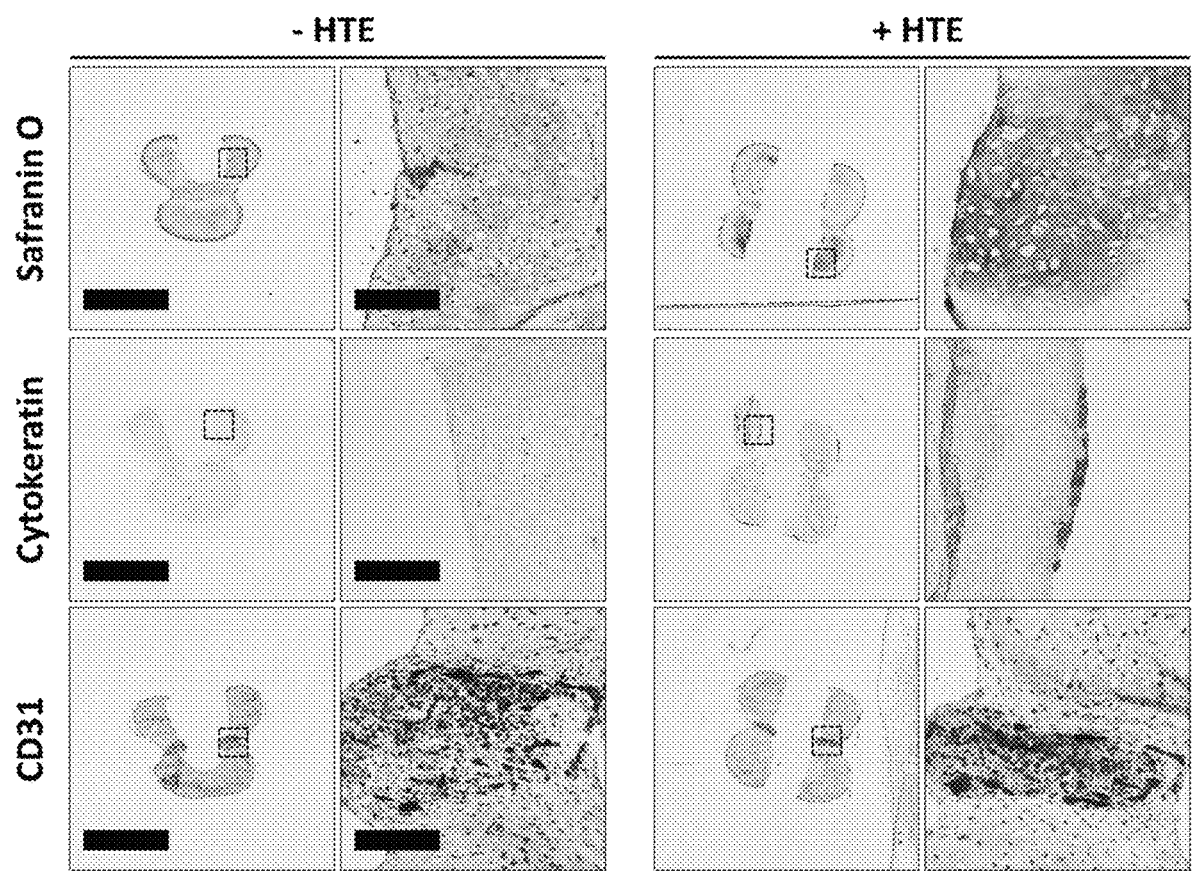
FIG. 22 illustrates histologic staining of tri-tissue tracheas. CVC tubes were suspended in epithelial cell media in the absence (−HTE) or presence (+HTE) of primary human tracheal epithelial (HTE) cells. Samples were harvested at 24 hours, sectioned and stained with Safranin O with a Fast Green (blue/green) counterstain as an indication of cartilage extracellular matrix. To determine epithelial attachment, sections were stained for cytokeratin. Finally, sections were stained for CD31 and counterstained with Mayer's hematoxylin to identify endothelial cells. The left column scale bar for −HTE images is 2 mm and for the right column, it is 200 µm. Images in +HTE group are at same magnification as corresponding −HTE images. Dotted black box regions are shown in high magnification.

After fusing two cartilage rings and one vascular ring as before, CVC tubes were cultured in a suspension of human tracheal epithelial (HTE) cells for 24 hours. Staining for GAG and CD31 demonstrated that cartilage matrix and endothelial prevascular structures, respectively, were still present after the additional culture in epithelial media (FIG. 22). Importantly, cytokeratin staining demonstrated the presence of adhered epithelial cells (FIG. 22) to the surface of the CVC tubes.

Subcutaneous Implantation in Athymic Mice

After 19 days of in vitro culture, prevascular—cartilage composite tubes were implanted subcutaneously in athymic mice to assess vascularization of the engineered tissues. In addition to the CCC and CVCVC tubes described above, one additional group was included in this study. This new, third group consisted of 3 cartilage rings initially cultured in BPM separated by 2 vascular rings, composed only of MSCs, initially cultured in vasculogenic media. The vascular rings were seeded into the agarose molds and cultured like the vascular rings previously described but without the HUVECs. Upon fusing, these tubes were termed CVCVC-noH and cultured in mixed media. Tissue engineered constructs that were fixed at day 0 before implantation and those harvested from the mice 15 and 42 days after implantation were processed for histology and immunohistochemistry (FIG. 23). The tubular structure was well maintained, and connective tissue had grown into the lumens of all samples. Although mechanical testing was not possible due to low sample numbers, explants were very firm to the touch and qualitatively stiffer than all in vitro-cultured CVCVC or cartilage-only tubes described previously when bisected with a razor blade for histological processing. Composite neotracheas with intervening prevascular rings (with HUVECs) and control prevascular rings (without HUVECs) showed slightly more deformation from their original shape than tubes comprised solely of cartilage rings. The cartilage rings in composite tubes were slightly displaced with respect to each other along the longitudinal axis resulting in an offset tube. All samples showed the presence of GAG by Safranin O staining at day 0 and day 15 harvest, with CCC tubes exhibiting the strongest staining (FIG. 23A). However, the staining for GAG was reduced in all samples at 42 days (N=1). Alizarin red S staining demonstrated progressive calcium deposition within the samples over the course of the in vivo culture (FIG. 23A). No calcium staining was seen at time 0. Frozen sections of day 42 explants were stained with DAPI and fluorescently imaged for perfused lectin staining of human endothelial cells to show human cell-derived vasculature (FIG. 23B) that anastomosed with the host. No lectin staining was seen in CCC and CVCVC-noH samples. However, staining was seen in the CVCVC tube, and some HUVECs appeared to form structures with lumens.

Cartilage Rings and Tubes with Defined Dimensions

Tracheal cartilage provides mechanical support to the airway, which is imperative for proper airway function. Our group has demonstrated that scaffold-free, hMSCs with localized chondrogenic growth factor (TGF-β1)-delivering bioactive microspheres can be employed to engineer cartilaginous 2 mm inner diameter rings and tubes which behave like the similarly-sized native rat tracheas. In the present work, we hypothesized that the number of hMSCs and hMSCs with TGF-β1-laden microspheres used to fabricate 2 mm inner diameter rings can be varied to engineer rings with different wall thicknesses. At the same time, constructs with diameters >2 mm are required for testing in a larger animal model, like the rabbit (~6 mm inner diameter), and eventually translating for human use (>12 mm inner diameter). The size of the custom culture wells and tube holders were modified to alter the diameter of resultant rings and tubes.

By changing the cell and microsphere numbers, cartilage ring (hMSC or hMSC+MS) thickness could be altered by 25-35%. However, even the thinnest rings were still not as thin as the rat trachea (FIG. 17B). It is unclear if a thicker-walled tracheal replacement will impede tracheal function in a rat airway defect model. Furthermore, the incorporation of additional tissue types and altered culture conditions, which will be necessary to functionalize the cartilage tube, will likely reduce the thickness of the cartilage. Finally, the customizable annular culture wells can easily be altered to obtain narrower troughs or modified trough geometry (e.g., U-bottom vs V-bottom) to produce thinner rings or even other geometrical shapes if desired. In addition, the ultimate tensile stress (UTS, failure load normalized by loaded area) of all rings, except the 0.2 million cells per ring without microspheres condition, were similar among the groups as well as compared to the rat trachea, which means that geometry of the tissue does not influence the mechanical properties of the cartilage and that engineered rings may fulfill the mechanical support requirement when used in rat airway repair.

Next, cartilaginous rings and tubes of larger diameters were engineered by modifying the cell culture wells and tube holders to produce 6 and 12 mm inner diameter constructs in addition to 2 mm constructs. Surprisingly, the number of hMSCs with microspheres required to reliably form complete tissue rings did not scale linearly with the circumference of the post. In fact, seeding 2.4 million hMSCs in 12 mm wells (6×0.4 million cells/ring) resulted in only 25% ring formation frequency. As a result, the cell number was increased by 25% in all sizes of rings (0.5 million/2 mm ring, 1.5 million/6 mm ring and 3 million/12 mm ring) while keeping the microsphere-to-cell ratio constant. Still, the frequency of ring formation decreased with increasing diameter (FIG. 3A). It is possible that the smaller curvature (1/radius; 1 $mm^{-1}$ for 2 mm, 0.33 $mm^{-1}$ for 6 mm, 0.17 $mm^{-1}$ for 12 mm) affected the ability of the hMSCs and microspheres to self-assemble into continuous rings and ultimately elaborate chondrogenic matrix resulting in lower GAG/DNA and GAG/WW (FIGS. 18F, G). In fact, previous reports have shown that geometrical shape cues, like curvature, can direct hMSC differentiation. Nevertheless, chondrogenesis was not severely affected as GAG/DNA content only decreased by 23% and 25% for 6 mm and 12 mm tubes, respectively, compared to 2 mm tubes, while type II collagen staining remained strong. Tube wall thickness data indicate that 6 mm tubes (1.16 mm average thickness) may be of suitable size for the rabbit airway (0.97 mm average thickness) repair and 12 mm tubes (1.26 mm average thickness) may be adequately sized for use in humans whose tracheal cartilage is ~1 mm thick. However, the 6 mm engineered cartilage tubes required only 8% of the rabbit tracheal load to collapse 80% of their respective lumen diameters and 12 mm cartilage tubes are likely substantially weaker than human tracheas (FIG. 18I). As expected, the tube structural stiffness is proportional to the ratio of the radius to the wall thickness with greater ratios leading to more compliant tubes. Mechanical properties of engineered tracheal tubes containing multiple cell types were further weakened (FIG. 21E). However, it is important to note that both the cartilage-only tubes and the prevascular-cartilage tubes are immature constructs that were only grown for 3 and 2 weeks, respectively. So, it is not surprising that the neotracheas are weaker than their native counterparts, which had developed for much longer. In addition, it is unclear whether the weaker luminal collapse properties of the tracheal replacement would hinder airway function because healthy infant tracheas can safely collapse up to 50%, mostly by invagination of the posterior smooth muscle wall, during the first milliseconds of deep inspiration, while normal breathing results in minimal deformation. Importantly, all engineered tubes recoiled to nearly 100% of original diameter after luminal collapse just like the native rabbit trachea (FIG. 18J). If necessary, mechanical properties of the tubes may be improved by increasing the wall thickness by using more hMSCs and microspheres or lengthening the culture time to elaborate more mature cartilaginous matrix. Taken together, these findings demonstrate the flexibility of the customizable culture system and show that cartilage tissue rings and tube with specific dimensions can be successfully engineered.

Epithelialized Cartilage Bilayers

Tracheal epithelium performs a crucial role in the innate host defense by (1) providing a protective physical barrier and (2) producing mucus to allow the body to clear infectious agents and environmental toxins. These functions can be temporarily or permanently compromised in patients with airway stenosis and malignant tumors or after tracheal resection. Hence, one of the main challenges for the translational application of tissue-engineered tracheas is the ability to efficiently restore a functional epithelial cell layer. Isolated epithelial cells are typically cultured on protein coated cell culture inserts. Upon reaching confluence, the medium from inside the cell culture insert is removed, thereby exposing the epithelial sheet to air. This ALI culture model mimics the in vivo distribution of the airway lining; the apical side of epithelial cells faces the airway lumen and the basal side of the cells is attached to the basement membrane. We hypothesized that our established scaffold-free, high-cell density cartilaginous sheets may support epithelialization.

In this Example, we were able to successfully engineer cohesive epithelial-cartilaginous bilayers. Qualitative histological analysis showed that while the 50:50 mixture of BPM and BEGM required for the maintenance of the two distinct cell types slightly reduced GAG content and altered type II collagen distribution in the underlying cartilaginous sheets relative to positive controls, the thickness of the epithelial layer seeded on top increased over time when exposed to air. Differences in GAG deposition in the C sheets compared to EC groups cultured in mixed media may be a result of hBEC-hMSC cell-cell communication, nutrient availability or diffusion limitations. Similarly, the E sheet positive control was thicker than the epithelial layers on the EC constructs suggesting that nutrient availability, nutrient and oxygen diffusion or the presence of hMSCs altered epithelial layer development. Furthermore, expression of cytokeratins, an epithelial cell marker indicating structural cell integrity, was robust in the epithelial portion of the EC bilayer sheets and similar to that of the E control sheets cultured on standard cell culture inserts. The successful epithelial cell growth and differentiation at ALI and submerged in media achieved here is promising for engineering tubular tracheal replacements with a luminal epithelial coating.

Incorporation of Prevascular Rings into Tubes and Tri-tissue Tracheas

Similar to nearly all tissues in the body, native trachea has a vascular supply to facilitate oxygen and nutrient delivery and metabolic waste removal, critical for the survival of the investing soft tissue and epithelium lining the lumen. To develop a tissue engineered construct of clinically relevant size, the construct must be able to quickly develop a microvascular supply to survive after implantation. Neovascularization in replacement tracheas has been explored in only a few studies whose constructs contained vascular progenitor or endothelial cells obtained from adipose, bone marrow or skin tissue. In vitro approaches to support vascularization of replacement tracheas have mostly relied on scaffold materials with potential angiogenic properties (e.g., decellularized allogeneic trachea) or delivery of growth factors to drive angiogenesis. However, relying solely on host blood vessel infiltration may be insufficient in an orthotopic tracheal replacement because transplanted cells in the interior of the construct may die before becoming adequately microvascularized. Therefore, in this work, a prevascularization approach was developed to provide the framework for a microvasculature. By seeding endothelial cells with stromal supporting hMSCs in a ring mold and culturing for 2 weeks in EGM-2, the endothelial cells were able to self-assemble into prevascular structures (FIG. 20) reminiscent of the prevascular cords and plexuses formed from blood islands in the mesenchymal condensations during embryonic vasculogenesis. Furthermore, with such a high cell number, the interior of these constructs may have been at low oxygen tension, a known pro-vasculogenic stimulus, that may have enhanced prevascular structure formation.

The prevascular soft tissue rings were successfully stacked with cartilage rings resulting in ring fusion into tubes with similar architecture to native trachea (FIG. 20). The presence of a prevascular network in the composite tubes will allow for the support of a luminal epithelium, a clear advance beyond cartilage only tubes. Unlike previous endothelialization approaches for tracheal tissue engineering, this strategy is advantageous because it avoids extensive material processing required for the use of decellularized materials, the need to reseed endothelial cells into the decellularized tissues, the need for ectopic implantation prior to orthotopic use and the use of angiogenesis-inducing drugs and it allows for precise spatial control over prevascular tissue generation.

Stacked prevascular and cartilaginous rings fused together to form continuous multi-tissue constructs. While the essential features of each tissue type were maintained throughout the co-culture period, the resultant phenotype of each tissue type was diminished somewhat compared to that resulting from individual culture in medium for each respective tissue type. Prevascular rings cultured for the duration of the experiment in EGM-2 showed a high degree of endothelial organization into prevascular plexus-like structures (FIG. 20). However, in composite tubes, there was a lower degree of endothelial cell incorporation into such structures, likely due to the decreased concentration of angiogenic growth factors in the mixed media. The GAG and GAG/DNA content in the prevascularized tubes cultured in mixed media was less than in tracheal tubes cultured in 100% BPM as demonstrated quantitatively by biochemical analysis (FIGS. 21A-C) and qualitatively by Safranin O staining (FIG. 20). This decrease in GAG content was demonstrated to be, at least partially, due to the media and not the presence of prevascular rings because a similar decrease in GAG content was seen in cartilage-only tubes cultured in the same 50:50 mixed media used with the prevascularized tubes. The weakened load bearing properties of prevascular tubes (FIG. 21E) may be a result of the decreased GAG content from the culture in mixed media, which would decrease the mechanical properties of the engineered cartilage component. Nevertheless, tube recoil after luminal collapse mechanical testing was minimally affected (FIG. 21F). To demonstrate the capability this system to simultaneously support a further, third, physiologically relevant tracheal tissue type, CVC tubes were cultured in a suspension of epithelial cells to form tri-tissue tracheal constructs. Importantly, the cartilage and prevascular phenotypes were maintained (FIG. 22) through this additional period of culture while allowing for the attachment of epithelial cells on the surface of the CVC constructs (FIG. 22). The epithelial cell coverage was not complete, but rather discontinuous. However, in areas of coverage, many cells were seen in juxtaposition with each other as opposed to individually attached cells, which may allow for the establishment of a continuous epithelium to provide an immunologic barrier function. These results demonstrate the feasibility of tri-tissue tissue engineering in the current system.

The composite prevascular—cartilage tracheal constructs were then implanted subcutaneously in mice (FIG. 22). Critical to their function of supporting an open airway, the engineered tracheas maintained their tubular architecture and their mechanical integrity was enhanced throughout in vivo culture. Substantial GAG staining was observed at the time of implantation and after 15 days in all groups. However, at the last time points, less GAG staining was evident. Progressive calcification of the constructs was noted (FIG. 22A) with the staining appearing principally in the peripheral regions of the cartilage segments of the tubes. It may be that the chondrogenically driven hMSCs are contributing directly to tissue calcification themselves or by recruitment of host osteoprogenitor cells. It has been shown that control of hMSC fate is challenging as chondrogenically driven hMSCs can eventually lead to calcified tissue. It should be noted, however, that a degree of calcification is seen in about half of native tracheas in the elderly without deleterious effects.

The intravenous injection of FITC-UEA-1 allowed for the identification of human endothelial cells that were incorporated into perfused vasculature within the engineered neotracheas (FIG. 22B). Predictably, no such staining was found in samples that lacked HUVECs. However, in the tracheal constructs with prevascular segments containing HUVECs, lectin-labeled cells were seen in the explanted tissue. These positively staining cells were only seen in the prevascular segments of the tracheas indicating that there was no vascular invasion into the cartilage segments from the prevascular rings. The labeled endothelial cells were variably seen in circular or short cord-like structures. The circular assemblies of stained HUVECs likely indicate patent lumens that were perfused with lectin containing host blood. While vascular lumen formation was not observed in vitro, the development of such mature, stable structures may have required the perfusion present in vivo. The spread HUVECs that do not enclose a lumen may be sections through the walls of vessels not oriented perpendicular to the plane of the section. Alternatively, as these stained, spread cells were often in the vicinity of lumen forming HUVECs, the vasculature formed by the transplanted cells may be leaky and as there are no lymphatics to drain the vascular filtrate, the lectin may simply be staining unincorporated HUVECs in the vicinity of the new HUVEC-derived vasculature. To enhance vascularization in the future it may be valuable to vary chondrogenic to vasculogenic media ratios during in vitro culture. In addition, microparticles presenting vasculogenic growth factors may be incorporated into prevascular rings, which may allow for a more uniformly distributed delivery of these factors than is possible by exogenous delivery alone to thicker constructs.

In this example, a modular, scaffold-free approach for engineering complex tubular hollow organs was presented via the formation of a tri-tissue engineered trachea. The three distinct tissues (i.e., cartilage, epithelial and vascular) with defined spatial placement provide for luminal rigidity, a respiratory epithelium and prevascular structures to facilitate perfusion after implantation and anastomosis with host vasculature. Moving forward, prevascular-cartilaginous tubes may be epithelialized on the lumen with the aid of a tubular organ bioreactor. This modular, tubular tissue and organ engineering approach may also find great utility for regenerating other tissues such as large blood vessels and segments of the gastrointestinal (i.e., esophagus, intestines) and urinary (i.e., ureters) tract.

Example 4

In this Example we tested the feasibility of incorporating microspheres into self-assembled human SMC rings, and evaluate the effects on ring structure and mechanical properties. We first tested microsphere incorporation in rings cultured in a commercially available SMC growth medium, which supports SMC proliferation and self assembly into tissue rings. However, the growth medium contains epidermal growth factor and fibroblast growth factor (FGF), which have been shown to interfere with TGF-β1-mediated differentiation to a healthy "contractile" SMC phenotype. Thus, we also tested incorporation in a differentiation medium, which does not contain growth factors and supports SMC differentiation to a healthy "contractile" phenotype. The second goal of this work was to evaluate the feasibility of utilizing gelatin microspheres to deliver TGF-β1 to three-dimensional self-assembled SMC constructs to improve ring structure and function. TGF-β1 is important in vascular tissue engineering because it stimulates ECM synthesis (e.g., collagen and elastin), induces contractile protein expression in SMCs (e.g., smooth muscle alpha actin and calponin), and enhances vascular graft contractility. These studies may be essential for future work aimed at modeling focal changes in the vascular wall characteristic of disease.

Materials and Methods

Gelatin Microsphere Preparation

Microspheres were formed and characterized using methods described previously. Briefly, a water-in-oil emulsion was created with 11.1 w/v % type A gelatin (Sigma-Aldrich) and olive oil (GiaRussa). Gelatin microspheres were crosslinked with 1% w/v genipin (Wako) for 3 h at room temperature. Ninhydrin assay was used to quantify the degree of polymer crosslinking. Images of microspheres were taken on a TMS microscope (Nikon) with Coolpix 995 camera (Nikon). Microsphere diameters were measured using ImageJ software.

Human SMC culture

Human coronary artery SMCs (Lifeline) were cultured in Lifeline complete growth medium (Lifeline VascuLife Growth Medium) supplemented with 0.2% penicillin—streptomycin (Mediatech) and 1% amphotericin B (Corning Cellgro). The differentiation medium (adapted from Lavender et al. 30) consisted of a 1:1 ratio of Dulbecco's Modified Eagle's Medium (DMEM; Mediatech) and Ham's F-12 (Mediatech) with 1% insulin-transferrin-selenium, 1% fetal bovine serum (PAA Laboratories), 1% 1-glutamine (Mediatech; glutagro supplement), 1% penicillin-streptomycin (Mediatech), 1% amphotericin B (Mediatech), and 50 mg/mL ascorbic acid (Wako).

SMC Ring Self-Assembly and Unloaded Microsphere Incorporation

Agarose molds were prepared using methods described previously with some modifications to the mold design. Briefly, a solution of 2% agarose in DMEM (w/v) was autoclaved, pipetted into molds made from cured polydimethylsiloxane (SYLGARD 184; Dow Corning), and cooled to room temperature to solidify. Agarose wells were transferred into a six-well plate and equilibrated overnight in growth medium. Each mold consisted of five wells, each with a 2-mm-diameter center post (FIG. 24D).

Before ring seeding, microspheres were UV sterilized for 10 min. The unloaded (growth factor free) microspheres were hydrated in phosphate-buffered saline (PBS) for 2 h at 37° C. Then, microspheres were diluted to twice the desired concentration (9.6 mg microspheres per mL for 0.6 mg/$10^6$ cells, and 3.2 mg microspheres per mL for 0.2 mg/$10^6$ cells) in serum-free growth medium. SMCs were resuspended at a concentration of $16 \times 10^6$ cells/mL and mixed 1:1 with microspheres to achieve final concentrations of 0, 0.2, or 0.6 mg microspheres per million cells. The cell-microsphere suspension was seeded into the agarose wells (shown schematically in FIG. 24) with 400,000 cells per ring. All rings were seeded in growth medium and then cultured in growth medium or switched to differentiation medium after one day. Rings were cultured for a total of 7 or 14 days.

TGF-β1-Loaded Microsphere Preparation and Incorporation within Tissue Rings

UV-sterilized microspheres were incubated in a solution of 80 ng/mL TGF-b1 (Peprotech; 400 ng/mg microspheres; 5 mL/mg microspheres) in PBS for 2 h at 37° C. Rings were seeded with 0.6 mg microspheres per million SMCs (as described above) in growth medium and switched to differentiation medium after 24 h. In the designated control groups, 10 ng/mL exogenous TGF-β1 was added to the differentiation medium on day 1 and continued until day 14.

Histology and Immunohistochemistry

Tissue rings were fixed for 1 h in 10% neutral buffered formalin, embedded in paraffin, sectioned in 5 mm slices, and adhered to charged slides (Superfrost Plus; VWR). Hematoxylin and eosin staining was used to examine ring morphology, and Picrosirius Red/Fast Green (Sigma) was used to visualize collagen.

To examine contractile protein expression, deparaffinized slides were blocked with 1.5% normal rabbit serum (NRS; Vector) in PBS for 45 min at room temperature. Antigen retrieval was performed on samples stained for calponin by incubating slides in 10 mM Tris, 1 mM ethylenediaminetetraacetic acid, and 0.05% Tween-20 (pH 9.0) in a pressure cooker for 5 min. Samples were incubated at 4° C. overnight with the primary antibodies, calponin (Dako; monoclonal mouse anti-human clone CALP) or smooth muscle alpha actin (Dako; monoclonal mouse anti-human clone 1A4), diluted 1:100 in 1.5% NRS. Control slides were incubated with mouse immunoglobulin G (Vector). Samples were incubated in a secondary antibody (Invitrogen; Alexa Fluor 488 rabbit anti-mouse) at a 1:400 dilution in NRS for 1 h at room temperature and stained with Hoechst 33342 (Invitrogen; 1:6000 dilution in DI water for 6 min) to visualize cell nuclei.

SMC Ring Thickness and Diameter Measurements

Rings were removed from the agarose wells and placed in a PBS-filled dish under a machine vision system (model 630; DVT Corporation). Ring thickness was averaged from measurements in four locations around the circumference of each sample using edge detection software as described previously (Framework 2.4.6; DVT10). For microsphere incorporation experiments, these thicknesses were used to calculate cross-sectional area and ultimate tensile stress (UTS).

For the TGF-β1 treatment experiments, rings treated with TGF-β1 contracted on removal from agarose posts, causing changes in thickness. To control for this, thickness was calculated from images taken before removing rings from molds using ImageJ. After removal, additional images of rings were taken using a stereoscope (Leica EZ4D). Final diameter (two measurements per ring) and thickness (four measurements per ring) were measured using ImageJ to determine changes after contraction.

Mechanical Testing

After 14 days, rings were pulled to failure with a uniaxial testing system (ElectroPuls E1000; Instron) as described previously. Ring cross-sectional areas were calculated from thickness measurements, and samples were mounted over two stainless steel wires. After applying a tare load, each ring was subjected to eight precycles and pulled to failure at 10 mm/min. Data were analyzed in a custom MATLAB (The MathWorks, Inc.) program to calculate UTS (failure load/cross-sectional area), maximum load, maximum strain, and maximum tangent modulus (MTM; maximum slope of stress/strain curve) of each ring.

Western Blot Analysis

Western blotting was performed with samples flash frozen in liquid nitrogen following mechanical testing. Samples were lysed for 30 min in lysis buffer (diluted from 5-solution of 200 mM Tris at pH of 7.5, 750 mM NaCl, 40% glycerol, 0.0635% Triton X-100, 0.025% Tween-20, and 0.01% NP-40) containing protease inhibitors (Thermo Fisher), mechanically homogenized, and briefly sonicated. A BCA assay (Thermo Fisher) was then used to determine protein concentration in each sample, to allow equal amounts of protein to be loaded into each lane. Samples were boiled for 5 min in sample buffer (5·solution of 60 mM pH 6.8 Tris-HCl, 25% glycerol, 2% sodium dodecyl sulfate, 14.4 mM b-mercaptoethanol, and 0.1% bromophenol blue) before loading. Fifteen micrograms of protein per sample was loaded into lanes of polyacrylamide gels with a 10% resolving and 5% stacking gel. After transfer, polyvinylidene fluoride membranes were blocked with 5% nonfat dry milk powder (BioRad) in Tris-buffered saline plus Tween 20 (TBST) for 1 h at room temperature. Membranes were incubated in smooth muscle alpha actin (1:1000; Dako; monoclonal mouse anti-human clone 1A4) or calponin (1:500; Dako; monoclonal mouse anti-human clone CALP) antibodies diluted in 1% milk powder in TBST overnight at 4° C. Membranes were incubated for 1 h at room temperature in a secondary antibody (1:3000 goat antimouse; Bio-Rad). Antibodies were detected using an HRP substrate kit (Thermo Fisher) and imaged using a BioRad gel documentation system. After imaging, membranes were incubated overnight at 4° C. with the anti-histone (1:250, H3; Santa Cruz) primary antibody as a loading control, and then, 1 h at room temperature with goat anti-rabbit horseradish peroxidase conjugate (1:5000; BioRad) before imaging. Blots were analyzed using ImageJ. Smooth muscle alpha actin and calponin were both normalized to histone in each blot.

Statistical Analysis

Mechanically tested samples that failed during loading or precycling were omitted from analysis. Statistical analysis was performed using SigmaPlot software (version 12.5; Systat Software, Inc.). One-way analysis of variance (ANOVA) tests with Holm-Sidak post-hoc analysis were used to determine statistical significance ($p<0.05$) of normal data sets. For data sets that failed a normality test, a one-way ANOVA on ranks test was performed with Dunn's multiple comparison test. Data are represented as mean–standard deviation (SD).

Results

Gelatin Microsphere Characterization

Two batches of crosslinked gelatin microspheres were prepared for microsphere incorporation and growth factor delivery studies, with average microsphere diameters of 47.5-42.7 and 48.4-41.9 mm (mean–SD) and crosslink densities of 32.6-6.1% and 35.7-15.4%, respectively. Previous reports have characterized degradation and TGF-β1 release profiles from similarly sized gelatin microspheres prepared using the same protocol and materials as this study.

Effects of Microsphere Incorporation on Self-Assembled SMC Rings Cultured in Growth Medium Microspheres were incorporated during ring selfassembly as shown schematically in FIG. 24. Microspheres appeared incorporated within rings, with better distribution around the rings when seeded with 0.6 mg/$10^6$ cells compared to 0.2 mg/$10^6$ cells (FIGS. 25A-C, G-I). Microspheres were clearly visible within 7-day rings, but were difficult to discern after 14 days (FIGS. 25D-F, J-L), suggesting degradation between 7 and 14 days.

Inclusion of 0.6 mg/$10^6$ cells significantly increased ring thickness at 14 days compared to rings with 0.2 or 0 mg/$10^6$ cells (FIG. 26). Microsphere incorporation caused a significant decrease in ring UTS (FIG. 27A) and MTM (FIG. 27B). Significant changes in failure load (FIG. 27C) and strain (FIG. 27D) were not observed, however, there was a slight decrease in failure load in rings with 0.6 mg/$10^6$ cells.

Effects of Microsphere Incorporation on Self-Assembled SMC Rings Cultured in Differentiation Medium Similarly, histological analysis of rings cultured in differentiation medium showed that microspheres were incorporated on day 7, with clear evidence of degradation by day 14 (FIG. 28). Rings without microspheres were significantly thinner than with 0.6 mg/$10^6$ cells, whereas 0.2 mg/$10^6$ cells did not significantly increase ring thickness (FIG. 29). Overall, rings cultured in differentiation medium were thinner than rings cultured in growth medium (0.25-0.31 mm vs. 0.59-0.72 mm; FIGS. 29 and 26, respectively).

Uniaxial tensile testing of rings cultured in differentiation medium with 0.6 mg/$10^6$ cells showed a significant increase in failure load (FIG. 30C) and failure strain (FIG. 30D). No significant changes in UTS (FIG. 30A) or MTM (FIG. 30B) were observed, although a slight decrease in MTM was observed in the 0.6 mg/$10^6$ cells group and a slight increase in UTS was observed in rings with incorporated microspheres compared to rings without microspheres.

TGF-β1 Delivery from Incorporated Microspheres within Self-Assembled SMC Rings

To assess the effects of microsphere-mediated TGF-β1 delivery within rings, microspheres were loaded with TGFb1 and incorporated into rings. Unloaded gelatin microspheres (0.6 mg/$10^6$ cells) were incorporated into control rings to assess the effects of microspheres alone on rings with or without exogenously added TGF-β1. Control rings without microspheres were prepared with and without TGF-β1 supplementation to assess the effects of exogenous TGF-β1 on SMC contractile protein expression.

Histological analysis at day 14 showed that microspheres are well incorporated and still visible at day 14. They did not appear degraded (FIG. 31C-E, H-J) to the same extent as observed in initial microsphere incorporation experiments (FIG. 28).

Representative images of 14-day rings are shown in FIGS. 32A-E. Samples treated with either exogenous TGF-β1 (FIGS. 32B, D) or TGF-β1-loaded microspheres (FIG. 32E) appeared to spontaneously contract on release from the agarose wells to a greater extent than rings that were not exposed to TGF-β1 (FIG. 32A, C). To quantify contraction, the inner diameter of each ring was measured and the change in diameter was calculated (FIG. 32F). Change in ring thickness was also calculated (FIG. 32G). Rings treated with TGF-β1 exhibited a greater reduction in diameter (FIG. 32F) and a greater increase in thickness (FIG. 32G) compared to rings that were not exposed to TGF-β1. In this experiment, before removal from agarose posts, rings treated with TGF-β1, either exogenously or via microspheres, were significantly thicker compared to unloaded microspheres without TGF-β1. Specifically, rings had average thicknesses (−SD) of 0.14-0.02 mm without microspheres or TGF-β1, 0.12-0.02 mm with exogenous TGF-β1 but no microspheres, 0.25-0.03 mm with microspheres but no TGF-β1, 0.19-0.03 mm with microspheres and exogenous TGF-β1, and 0.21-0.05 mm with TGF-β1-loaded microspheres. A small number of samples failed during culture or removal from molds, resulting in the varying sample sizes in FIG. 32F (eight rings per group were originally seeded). An additional two rings were excluded from FIG. 32G, because there was insufficient contrast between the ring and agarose mold to obtain an initial thickness using the DVT.

Contractile protein expression was visible in rings from all three TGF-β1-treated groups (FIGS. 33B, D, E, G, I, and J). While positive staining could be seen throughout the TGF-β1-treated rings, the strongest signal was observed around ring edges (FIG. 33). Smaller amounts of smooth muscle alpha actin and calponin were also observed around the outer edges of rings cultured without added TGF-β1 (FIGS. 33A, C, F, and H).

These trends were also apparent when contractile protein expression was quantified with western blotting (FIG. 33K). Smooth muscle alpha actin expression was significantly higher in rings with loaded microspheres and rings with unloaded microspheres and exogenous TGF-β1 than in rings without microspheres or TGF-b1 (FIG. 33L). There were also increases in groups with exogenous TGF-β1, although the difference was not significant. A small increase was also seen in the group with microspheres but without TGF-β1. Calponin expression also increased in groups treated with TGF-β1 either exogenously or via microspheres, although this was only significant in the group with microspheres and exogenous TGF-β1 delivery (FIG. 33M).

When uniaxial tensile testing was performed on rings, several rings failed during loading or precycling, resulting in low sample sizes. There were no significant differences between sample groups, except that rings cultured with unloaded microspheres and no exogenous TGF-β1 had a higher failure load than rings without microspheres but with exogenous TGF-β1. A total of seven rings were tested for the group without microspheres or exogenous TGF-β1 and the group with microspheres but without TGF-β1, eight rings for the group with microspheres and exogenous TGF-β1 and the group without microspheres but with exogenous TGF-β1, and six rings were tested for the loaded microsphere group. Rings that failed during precycle or loading were not included in analysis, resulting in the varying sample sizes. Similar observations of ring contraction and contractile protein expression with TGF-β1 treatment were observed when the experiment was repeated with SMCs from a different manufacturer.

This Example shows the feasibility of microsphere incorporation within self-assembled SMC rings for the purpose of growth factor delivery, and evaluate effects on ring mechanical properties and morphology. Microsphere incorporation was tested in two medium types, shown to have different effects on SMC growth and differentiation, respectively. Ring tissue assembly and microsphere incorporation were successfully demonstrated independent of the medium in which the tissue rings were cultured.

The effects of microsphere incorporation on mechanical strength were evaluated, as polymer fragments within tissue engineered constructs can create focal weaknesses. When rings were cultured in growth medium, a decrease in UTS was measured, which may be due to the increase in ring thickness and cross-sectional area (given that stress is calculated as force divided by cross-sectional area). However, the load at failure was not significantly different between groups. Interestingly, when rings were grown in the differentiation medium, significant increases in failure load were observed in rings with microspheres, although UTS only slightly increased. This suggests that microspheres will not adversely affect ring mechanical strength when grown in differentiation medium. Others have reported increases in tissue strength and stiffness with gelatin microsphere incorporation, which may be due to improved oxygen and nutrient diffusion in dense tissues. The decrease in ring MTM was unexpected, as microsphere incorporation has been shown to increase tissue stiffness. However, microspheres in this experiment appear to be degraded by 14 days and may no longer be directly contributing to stiffness.

It is noted in this example that there was a large variation in microsphere size, however, the size distribution between batches is relatively consistent, and there is precedent for the use of similarly sized microspheres with large size variations. A large size variation could potentially result in ring failure due to the presence of some large microspheres, as any remaining fragments may create local stress concentrations. However, SDs in failure load were relatively small, suggesting rings were failing consistently despite the variation in microsphere size. In addition, the majority of microspheres in these studies were degraded before mechanical testing. In the few groups where microsphere fragments were still apparent, ring failure load was not negatively impacted.

A second batch of gelatin microspheres was prepared for the TGF-β1 delivery experiments. It was apparent from histological images that microspheres used for the TGF-β1 studies did not appear completely degraded at day 14 as in the initial microsphere incorporation experiments. This may be due to differences in crosslink density between the two microsphere batches, as increased crosslink density has been shown to slow degradation.

In vivo, SMCs in healthy blood vessels exhibit a "contractile" phenotype and contract or relax to regulate blood flow in response to stimuli. Following vascular injury or disease, SMCs shift to a "synthetic" phenotype characterized by increased proliferation and ECM deposition, and decreased contractile protein expression. SMCs in culture typically adopt this synthetic phenotype, making it necessary to differentiate cells in vascular constructs by switching to a differentiation medium with TGF-β1. TGF-β1 is well known to stimulate differentiation to a contractile phenotype and increase contractile protein expression. Our results are consistent with these observations, as rings supplemented with TGF-β1, either exogenously or through microspheres, displayed visible increases in expression of the contractile proteins, smooth muscle alpha actin and calponin (FIG. 33). These results were confirmed when contractile protein expression was quantified with western blotting. Smooth muscle alpha actin was significantly increased compared to untreated controls without microspheres in the TGF-β1-loaded microsphere group and unloaded microspheres with exogenous TGF-β1 (FIG. 33L). Calponin was significantly increased with unloaded microspheres and TGF-β1 treatment, although trends were visible in all three TGF-β1 groups (FIG. 3M). This suggests that microspheres successfully delivered TGF-β1 within tissue rings, and the bioactivity of TGF-β1 was maintained. Interestingly, there was also a notable, although not significant, increase in smooth muscle alpha actin in rings with unloaded microspheres but without exogenous TGF-β1, suggesting that microspheres alone may stimulate contractile protein expression. This is not entirely surprising, as microsphere incorporation alone has been shown to increase differentiation of other cell types, such as pluripotent stem cells, chondrocytes, and adipose-derived stem cells.

Controlling SMC phenotype and ring contractility is an important step for developing in vitro vascular disease models. In addition to increased contractile protein expression, rings treated with TGF-β1 visibly contracted when removed from agarose posts, resulting in significant decreases in diameter (FIG. 32), which is an expected outcome of the increased contractile protein expression. Others have also reported increases in vascular graft contractility in response to TGF-β1 treatment.

We have demonstrated that degradable gelatin microspheres can be incorporated into self-assembled vascular tissue constructs without adversely affecting ring strength, and can even increase ring failure load. Since gelatin is cell adhesive, it may provide tissue stability at early time points, which will be beneficial when rings are harvested for tube formation.

Example 5

In this Example, we provide an approach for fabricating 3D vascular tissue from human cells with spatially controlled heterogeneities, which may ultimately serve as a platform technology to introduce focal regions of pathological tissue within tissue engineered blood vessels (TEBVs). We demonstrate, in principle, that modular building units comprised of self-assembled human smooth muscle cell rings (with or without incorporated gelatin microspheres) can be fused together into a contiguous, heterogeneous tissue tube with distinct structural regions. To aid in handling and cannulation, electrospun PCL cannulation cuffs can be fused onto tube ends as reinforced extensions. In a proof-of-concept experiment, we showed that after 4 days of fusion culture, tubes with PCL cuffs could be cannulated and cultured on a custom luminal flow bioreactor.

In summary, we disclose a system for creating TEBVs that allows for customization of tissue structure and composition along the vessel length through the use of self-assembled cell ring units, degradable gelatin microspheres, and PCL cannulation cuffs.

Methods

The first goal was to enhance ring fusion and reduce fusion time. We did this by evaluating the effects of ring pre-culture time on ring fusion. Our next goal was to evaluate whether or not rings maintain spatial positioning during fusion, to determine the feasibility of creating focal heterogeneities. The third goal of this study was to demonstrate that we can cannulate and dynamically culture tubes. We incorporated PCL cannulation cuffs on tube ends as reinforced extensions for cannulation, and demonstrated the use of a custom luminal flow bioreactor for dynamic tube culture. Our next goal was to create focal heterogeneities within tubes, which we accomplished by creating localized regions of microsphere incorporation. Finally, we utilized the modular nature of our system to create branched structures.

Cell Culture

Human aortic smooth muscle cells (Lifeline) were cultured in Lifeline VascuLife complete growth medium according to the manufacturer's instructions. Human coronary artery smooth muscle cells (Lonza) were cultured and maintained in complete smooth muscle cell growth medium according to manufacturer instructions (SmGM-2; Lonza). Rat aortic smooth muscle cells (rat SMCs; WKY-3M22 [28]) were cultured in DMEM supplemented with 10% fetal bovine serum, 1% penicillin-streptomycin, 1% Non-essential amino acids, 1% L-glutamine, and 1% sodium pyruvate (Corning).

Tissue Ring Fabrication

Agarose wells (2 mm post diameter) were prepared as described previously (FIG. 34A) [25, 26] from 2% agarose (Lonza) dissolved in DMEM and autoclaved to sterilize. Human SMC rings were seeded into a modified agarose mold designed to fit 5 rings in a well of a 6-well plate, at a density of 400,000 cells/ring. For rat SMC experiments, molten agarose was poured into PDMS negatives, and each agarose well was placed into a well of a 12-well plate. Molds were equilibrated overnight in DMEM before use. Rat SMC rings were seeded at 500,000 cells per well. All seeded rings were incubated overnight to allow cell aggregation, then wells were flooded with fresh culture medium.

Tissue Tube Fusion with Varying Pre-Culture Time

To generate tissue tubes, rings fabricated from human aortic SMCs were removed from agarose molds at 3, 5, or 7 days in culture and threaded onto silicone tubing mandrels (Specialty Manufacturing Inc., O.D. 1.9 mm). Three rings per tube were gently pushed together on the mandrel to ensure rings were in contact (FIG. 34B), and the mandrel was secured in custom polycarbonate holders, which were placed in a 10 cm dish with 45 ml medium. The tubes were then allowed to fuse for an additional 7 days of static culture. The experiment was duplicated once with human aortic SMCs, and again with human coronary artery SMCs.

Fusion Angle, Length, and Thickness Measurements

A Leica inverted microscope (DMIL) with a digital camera (Leica DFC 480) was used to take phase contrast images of tubes daily for one week. Image J software (NIH) was used to measure the angle between rings (fusion angle, e), tube thickness (T), and tube length (L). Four fusion angle measurements, six thickness measurements, and two length measurements were obtained for each tube sample at each time point and averaged to yield a single mean for each parameter per tube per time point. Three independent samples were averaged for each group. After 7 days of culture, tissue samples were fixed for 1 hour in 10% neutral buffered formalin for histology. Data is represented as mean±SD.

CellTracker Labeling

CellTracker red and green (CMTPX and CMFDA, Invitrogen) were reconstituted to 10 mM in DMSO and diluted to a final concentration of 5 µM in DMEM (Corning). Plates of human aortic SMCs were rinsed with PBS and incubated with CellTracker solution at 37° C. for 45 minutes. The plates were rinsed with PBS, and growth medium was added for an additional 30 minutes at 37° C. Cells were then passaged and seeded into ring molds as described in section 2.2. After 3 days of culture, tubes were fabricated with alternating red and green labeled rings and imaged with an inverted fluorescent microscope (Leica DMIL) daily for 7 days. The experiment was duplicated once with human aortic and once with human coronary artery SMCs.

Polycaprolactone (PCL) Cannulation Cuff Fabrication

Electrospun PCL cuffs were prepared. Briefly, PCL was dissolved in 2,2,2 tri-fluoro-ethanol (TFE, T63002, Sigma) to form a 12% solution. The solution was then electrospun onto a 2 mm diameter mandrel using a 5 ml/hour flow rate, 15 cm collector distance, and a voltage of 15-20 kV. Cuffs were cut into segments approximately 3-4 mm in length, sterilized with ethylene oxide, and allowed to de-gas for a minimum of 48 hours before use.

Bioreactor Culture

Rings were fabricated with human aortic SMCs (Lifeline), and threaded onto silicone tubing after 3 days of ring culture, with PCL cuffs adjacent to rings on either end. Tubes were allowed to fuse for 4 days in static culture prior to removal from the silicone tubing mandrel and cannulation onto a custom bioreactor modified from Piola et al. Each bioreactor fits in its own individual 15 ml conical tube, which allows for multiple units to be cultured independently, with minimal culture medium (approximately 18 ml medium to fill each bioreactor unit and its tubing). The inner cannulas are adjustable, to accommodate tubes with lengths ranging from a few millimeters up to 3 cm. Medium flows from a peristaltic pump (Watson Marlow) through the vessel lumen. A syringe with 2 ml of medium and 3 ml of air is positioned between the pump and vessel, to dampen oscillations in medium flow from the pump. The medium then flows back into the chamber, before returning to the pump. Cannulated tubes were cultured with 10 ml/min applied luminal flow for 3 or 9 days. Two control tubes were left in static conditions for a total of 13 days (same total culture time as tube exposed to 9 days of flow).

Fabricating Tubes with Spatially Defined Regions of Microsphere Incorporation

Rings were fabricated from human aortic SMCs (Lifeline), with gelatin microspheres 59.3±28.8 µm in diameter and with a 32.3±15.3% cross-link density incorporated. Briefly, microspheres were hydrated in PBS (25 µl per mg microspheres) for 2 hours at 37° C., resuspended at 9.6 mg/ml and mixed 1:1 with CellTracker Red-labeled human aortic SMCs (16 million cells/ml suspension). Rings were seeded with 50 µl cell-microsphere suspension, resulting in rings with 400,000 cells/ring and 0.6 mg microspheres/million cells. After 3 days of culture, rings were threaded onto silicone tubing mandrels with a central region of microsphere-incorporated rings, and outer regions of rings without microspheres. Cannulation cuffs were placed adjacent to rings on tube ends. Tubes were cultured for 4 days in static conditions prior to fixation and paraffin embedding.

Generating Branched Vessels

Figure 35:
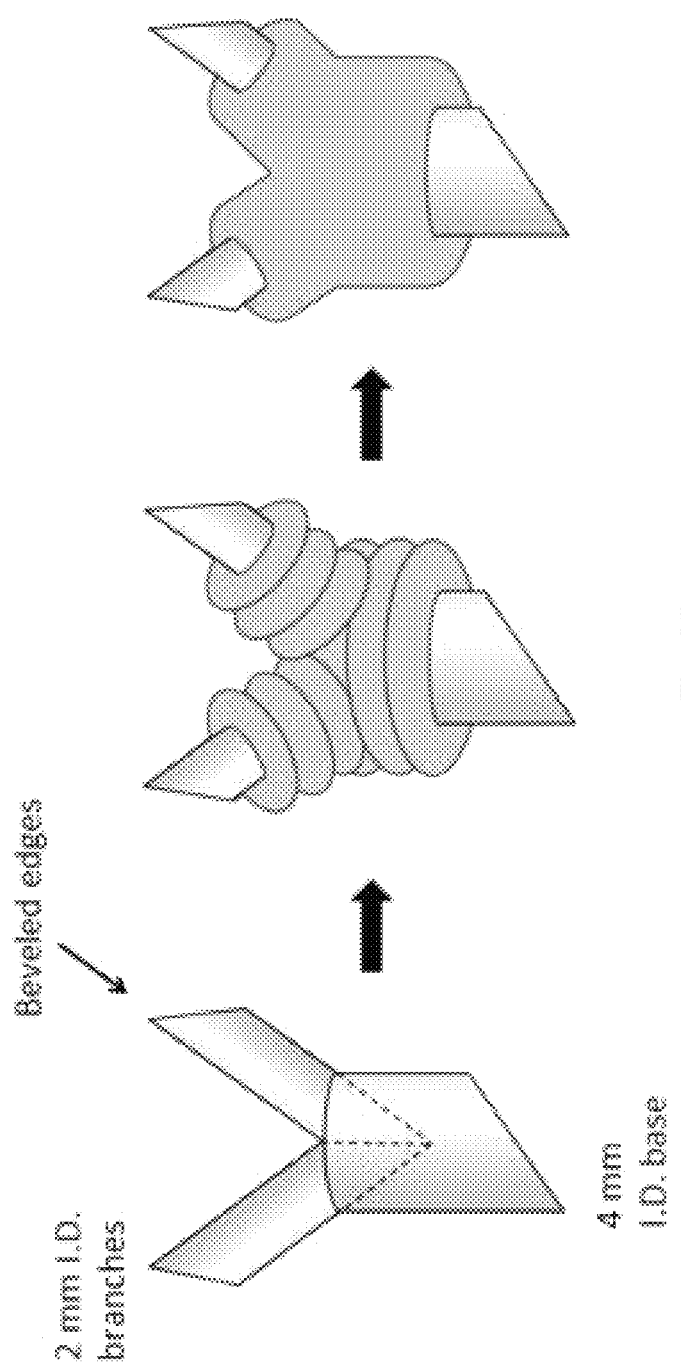
FIG. 35 is a schematic of branched tube formation method. Silicone tubing with a 2 mm I.D. and beveled edges was inserted into silicone tubing with a 4 mm I.D. SMC rings with a 2 mm I.D. were then threaded over the two branches, and rings with a 4 mm I.D. were threaded over the larger base. Rings were cultured to allow fusion into a branched vessel.

To generate branched vessels, custom Y-shaped mandrels were made from three pieces of silicone tubing (Specialty Manufacturing, Inc.), as shown in FIG. 35. The base portion was 4 mm OD (beveled on one end), and the two branches were 2 mm OD (beveled on both ends). One beveled end of each 2 mm OD piece of silicone tubing was placed facing each other and inserted into the flat end of the 4 mm OD tube. To create the branched vessels, 2 mm diameter rat aortic SMC rings were transferred onto each of the small branches of the mandrel and 4 mm diameter rings were then transferred onto the large branch of the y-shaped mandrel (4-8 rings per branch). Rings were fused in static culture for 7 days prior to removal of the silicone tubing mandrels. Low magnification images of the branched tubes were obtained with a Leica EZ4D stereoscope.

Histology

After fixing for 1 hour in 10% neutral buffered formalin, samples were processed, embedded in paraffin, and 5 µm longitudinal sections were adhered to positively charged slides. Hematoxylin and Eosin was used to examine tube morphology. Samples with CellTracker labeling were stained with Hoescht dye to visualize nuclei (Invitrogen, 1:6000 in DI water for 6 minutes). Images were acquired using an epifluorescent microscope (Leica DMLB2) with a digital camera (Leica DFC 480).

Statistics

Statistical tests were performed using SigmaPlot software (Version 11.0 Systat Software, Inc.). A two-way analysis of variance (ANOVA) with Holm-Sidak post hoc analysis was used to compare fusion angles, thicknesses, and lengths of tissue tubes. A p value of less than 0.05 was considered significant. A sample size of n=3 was used in statistically analyzed ring pre-culture experiments.

Results

Effect of Ring Culture Time on Human SMC Tube Fusion Rate

The first goal was to accelerate production of tissue tubes and enhance ring fusion by examining how ring "pre-culture" time prior to tube fabrication affects fusion. In previous studies, we observed cohesive tubes after fusion, but ring boundaries remained visible after a total 14 day culture period (7 days as rings, 7 as tubes). By decreasing ring culture duration prior to fusion, we aimed to decrease the length of time required to generate tissue tubes, and generate a more seamless ring fusion. Other published studies also suggest that less mature cell aggregates fuse together more rapidly than more mature tissues. Therefore, we hypothesized that decreasing the ring culture duration prior to fusion would decrease the length of time required to generate tissue tubes, and lead to more seamless ring fusion.

Human aortic SMC rings were removed from agarose molds after 3, 5, or 7 days of ring culture and cultured as tubes for 7 days, resulting in groups 3-7, 5-7, and 7-7, respectively (shown schematically in FIG. 35). Fusion was measured daily as the angle between adjacent rings, to determine the time course for tissue fusion (FIG. 36A). When human aortic SMC tubes were fused, there was a significant difference in fusion angle only at day 2 between the 7-7 group vs 5-7 group, and day 3 between the 5-7 group vs 7-7 and 3-7 groups (FIG. 36B). In all groups, the fusion angle appeared to plateau by day 3, suggesting complete ring fusion. Tube length (FIG. 36C) remained relatively constant over time, although tubes in the 3-7 group were significantly longer overall, and the 5-7 group was significantly shorter than the other 2 groups.

Significant differences were not observed in tube thickness (FIG. 36D), although tubes appear to thin slightly over time. These results are consistent with duplicate studies performed both with human aortic SMCs and human coronary artery SMCs.

Structure and Morphology of Fused Human SMC Tubes

To evaluate fusion of SMC ring units, tissue tube sections were stained with Hematoxylin and Eosin to compare morphology of the 3-7, 5-7, and 7-7 tubes. Tubes appeared well fused after a 7 day fusion period, although ring boundaries remained detectable. Ring boundaries are most distinct in the 7-7 group. Nearly seamless fusion was observed in the 3-7 group, although ridges were still slightly visible on the tube exterior (FIG. 37). This suggests that rings cultured for a shorter duration prior to tube fabrication may allow for more complete tissue fusion.

Spatial Positioning of SMCs within Rings During Fusion

To assess the feasibility of creating tubes with distinct tissue regions along the tube length, we next evaluated whether cells within ring units maintain their spatial position within tissue tubes after ring fusion. Three-day-old human aortic SMC rings were created from green or red CellTracker-labeled cells. Alternating red and green fluorescently-labeled rings were fused in culture for 7 days, and images were acquired daily. We did not observe "mixing" of cells at the ring borders over the culture period (FIG. 38A). This observation was confirmed when tubes fused for 7 days were examined histologically and stained with Hoechst (FIG. 38B-D). Similar results were observed when the experiment was repeated with coronary artery SMCs. Although some tissue compaction was visible, Hoechst-stained sections clearly show that cells within rings maintain their original spatial position after tube fusion.

PCL Cannulation Cuffs and Dynamic Tube Culture

The next step in generating an in vitro model is applying luminal flow, which is critical for maintaining a healthy blood vessel. However, self-assembled tissues can be fragile at early time points in culture, and may not withstand handling or suturing forces necessary to load the tissue into a flow bioreactor. Thus, our modular system for vascular tissue fabrication includes electrospun PCL cannulation cuffs incorporated onto each end of the tube via cellular attachment and infiltration from adjacent cell rings. Previously, we incorporated PCL cuffs into tubes made from rat aortic SMCs. In this experiment, we assessed the feasibility of incorporating PCL cannulation cuffs into human aortic SMC tubes to serve as reinforced extensions to aid in cannulation (FIG. 39A). After 4 days of fusion, we removed fused human tissue tubes from silicone tubing and mounted them onto a custom bioreactor. Cannulation cuffs fit snugly over bioreactor cannulas, and did not require additional suturing, as shown in FIG. 39B.

The bioreactor used in these studies was modified from Piola et al. An image of the bioreactor with a cannulated SMC tube inside is shown in FIG. 39C. A schematic of the bioreactor flow loop is shown in FIG. 39D. In this experiment, we attempted to cannulate three human aortic SMC tubes onto bioreactors. One failed during loading, one tube obtained a small hole during loading, and the third remained intact for loading. The tube with the small hole remained otherwise intact and was then fixed after 3 days of luminal flow. The third tube was successfully cultured with luminal flow for 9 days.

Incorporation of Degradable Gelatin Microspheres to Fabricate Focal Heterogeneities in Fused Tissue Tubes An important step towards modeling focal vascular diseases is the ability to create spatially controlled heterogeneities within engineered vessel walls. To do this, we incorporated degradable gelatin microspheres within rings (with CellTracker Red dye), and positioned them in a central region of the tube, between rings without microspheres (FIG. 40A). The region with incorporated microspheres is clearly visible due to CellTracker Red dye and genipin cross-linked microspheres, which both impart a purple hue to the tissue in these regions. Histological analysis demonstrated fully fused tubes with regions of microsphere incorporation within a localized region of the tube (FIGS. 40B, C).

Fabrication of Branched Structures

In addition to focal heterogeneities, we also assessed whether the modular nature of our system is conducive to fabricating complex physiological structures such as branched vasculature, which are challenging to fabricate in vitro. Other studies have demonstrated that bioprinting can be used to generate branched vessel networks, but this requires custom, specialized equipment. Creating branched TEBV constructs may allow us to model disease progression at vessel bifurcations, where intimal lesions are more likely to occur. Atherosclerosis and intimal thickening also occur more frequently at branching points within vessels. Using our unique modular system, we are able to build structures with complicated geometries by assembling the ring subunits into "Y"-shaped tubes.

To create branched structures, 2 mm and 4 mm diameter silicone tubing was used to generate a "Y" shaped mandrel, and rat aortic SMC rings of different diameters were stacked and allowed to fuse. Ring fusion was clearly evident by day 3 in both the 2 mm diameter branches and 4 mm diameter base. While the majority of the structure was fully fused by day 7, one small hole at the bifurcation remained (FIG. 41).

A primary goal of varying pre-culture time was to determine a time course for ring fusion, and develop cohesive tissue tubes in a minimal amount of time. In all experiments, fusion angles plateaued after 3-4 days. Here, we demonstrated that after only 3 days of ring culture and 4 days of ring fusion time (1 week total), tubes are strong enough for dynamic culture, which is a next step for developing a vascular disease model. However, slight increases in culture time, for example to 7 days instead of 4, may be needed to increase ECM deposition and reduce the number of tubes that fail during the loading procedure. Still, engineered vascular tissue is typically matured a minimum of 2 weeks in static culture prior to mounting on bioreactors for dynamic culture. This may be because cell-derived tissues have enhanced ECM production, tissue strength, and biological function compared to tissue fabricated using scaffold materials. We have observed that tissue rings generated from self-assembled cells are stronger than tissue rings made from an equivalent number of cells embedded in collagen and fibrin gels. Additionally, our PCL cannulation cuffs aid in handling and cannulation of tissue tubes at early time points.

To further evaluate fusion, we examined whether or not cells maintain spatial positioning within rings during fusion. We observed that rings with red and green CellTracker dye are still spatially distinct after 7 days of fusion. This result is consistent with previous reports examining fusion of tissue sheets and spheroids, which showed that limited cellular migration or "mixing" is evident between most fusing tissues, despite some tissue remodeling and compaction. Because cells within ring units maintained their spatial positioning within tubes, we can customize individual rings and place them in distinct regions of the tube prior to fusion. This feature will enable us to model focal disease pathologies in future studies, by engineering regions of tissues that contain a diseased cell phenotype in the middle of an otherwise healthy vascular tissue tube.

Shear forces created from fluid flow are important for the progression of many vascular diseases. Thus, it is critical to incorporate luminal flow during early culture of engineered vascular disease models. However, self-assembled tissues may be too fragile at early time points in culture to be sutured onto cannulas for dynamic culture. The modular nature of our system is conducive to adding biomaterial units on either end of the tissue tube to serve as reinforced extensions, without affecting tissue structure. We evaluated the incorporation of PCL cannulation cuffs with tubes fabricated from rat aortic SMCs. We applied this technology to human TEBV constructs, enabling the successful cannulation of vascular tissue tubes in a custom bioreactor for dynamic culture. A human aortic SMC tube remained intact for 9 days of dynamic culture. Additionally, the bioreactor chamber can be easily modified to separate the luminal vessel compartment from the external medium compartment. In future studies, this will allow endothelialization of cannulated tissue tubes, and enable us to flow vasoactive substances through the tube lumen for endothelial and SMC functional testing. For additional future experiments, this bioreactor can also be modified to apply cyclic stretch to tissue tubes.

We reported previously that incorporated gelatin microspheres can be used to locally deliver growth factors within SMC rings, for the purpose of controlling SMC phenotype. The gelatin microspheres degrade within 2 weeks, and do not adversely affect ring mechanical strength. Here, we demonstrated that rings containing degradable, cross-linked gelatin microspheres can be localized to a central region of the tissue tubes and successfully fuse with unmodified rings, to create a focal heterogeneity (FIG. 40). This ability to create focal changes is a unique attribute of our system, as other methods for fabricating self-assembled TEBVs only create homogenous tubes. The incorporation of gelatin microspheres will enable future experiments in which we will deliver growth factors or other molecules directly to the focal heterogeneity, allowing customization of ring-subunit function to better mimic focal vascular diseases.

While vascular disease often occurs at the site of vessel bifurcations, building a tissue engineered branched vessel to model these diseases is challenging. Bioprinting has shown proof-of-concept of generating branched vessel networks, but this approach requires specialized equipment, and spheroidal building blocks may not fuse completely. In our study, we demonstrated the versatility of our modular ring system by generating branched tubular structures from different sized rings. Four millimeter rings were used to build the base of the vessels whereas 2 mm rings were used to form the two branches. The rings fused almost completely at the bifurcation, although a small gap remained. Gaps resulting in incomplete tissue fusion are often a problem in modular tissues fabricated from tissue spheroids. Future work may require optimization of duration and other culture conditions to ensure complete fusion of branched vessels. Our ability to spatially control cell phenotype may allow us to create branched structures with focal disease pathologies; there are currently no published tissue engineering approaches for fabricating branched in vitro vascular disease models.

From the above description of the invention, those skilled in the art will perceive improvements, changes and modifications. Such improvements, changes, and modifications are within the skill of the art and are intended to be covered by the appended claims. All patents and publications identified herein are incorporated by reference in their entirety.

Having described the invention, we claim:

1. A method of forming an epithelial lined engineered tissue construct, the method comprising:
   providing undifferentiated and/or substantially differentiated progenitor cells;
   combining the undifferentiated and/or substantially differentiated progenitor cells with a plurality of nanoparticles and/or microparticles so that the nanoparticles and/or microparticles are dispersed and suspended with the undifferentiated and/or substantially differentiated progenitor cells in a culture medium;
   culturing the suspension of nanoparticles and/or microparticles and undifferentiated and/or substantially differentiated progenitor cells in a well having a defined shape to form a self-assembled cell aggregate, wherein the undifferentiated and/or substantially differentiated progenitor cells aggregate spontaneously or by themselves and without mechanical manipulation while in culture into the self-assembled cell aggregate having the defined shape and wherein the shape of the self-assembled cell aggregate is defined by surfaces of the well; and
   seeding the self-assembled cell aggregate with a layer of epithelial cells and further culturing the self-assembled cell aggregate seeded with the layer of epithelial cells in a culture medium to provide an epithelial lined tissue construct.

2. The method of claim 1, wherein the population of undifferentiated and/or substantially differentiated progenitor cells are autologous, allogeneic, or a combination thereof.

3. The method of claim 1, wherein the population of undifferentiated and/or substantially differentiated progenitor cells comprises at least one of chondrogenic cells, mesenchymal stem cells, and/or smooth muscle cells.

4. The method of claim 1, wherein the step of providing the undifferentiated and/or substantially differentiated progenitor cells includes:
   isolating undifferentiated and/or substantially differentiated progenitor cells; and
   expanding the undifferentiated and/or substantially differentiated progenitor cells.

5. The method of claim 1, wherein the undifferentiated and/or substantially differentiated progenitor cells comprise a population of chondrogenic cells and the chondrogenic cells endogenously produce an extracellular matrix when the population of chondrogenic cells is cultured in the well.

6. The method of claim 1, the nanoparticles and/or microparticles comprising a biocompatible and biodegradable polymer.

7. The method of claim 1, the nanoparticles and/or microparticles including at least one bioactive agent that is differentially and/or controllably released by the nanoparticles and/or microparticles.

8. The method of claim 7, the bioactive agent including at least one of TGF-β1 and/or BMP-2.

9. The method of claim 1, wherein the culture medium includes endothelial growth medium and at least one of a chondrogenic induction medium, osteogenic induction medium, angiogenic medium, or vasculogenic medium.

10. The method of claim 1, further comprising providing a plurality of the self-assembled cell aggregates, wherein the self-assembled cell aggregates are ring shaped; and stacking the plurality of self-assembled cell aggregates and further culturing the stacked plurality of self-assembled cell aggregates to fuse the plurality of self-assembled, scaffold-free, high-density cell aggregates and form a modular engineered tissue construct.

11. The method of claim 10, wherein the plurality of self-assembled cell aggregates include first self-assembled cell aggregates defining cartilaginous portions within the tissue construct and second self-assembled cell aggregates, defining noncartilaginous portions within the tissue construct, wherein the second self-assembled cell aggregates have differing mixtures of cells with or without nanoparticles and/or microparticles than the first self-assembled aggregates.

* * * * *